United States Patent
Timmerman et al.

(10) Patent No.: US 12,415,843 B2
(45) Date of Patent: Sep. 16, 2025

(54) ANTIBODY-INTERFERON FUSION PROTEINS FOR ENHANCING ADOPTIVE T CELL THERAPIES FOR THE TREATMENT OF CANCER

(71) Applicant: The Regents of the University of California, Oakland, CA (US)

(72) Inventors: John Matthew Timmerman, Los Angeles, CA (US); Reiko King, Los Angeles, CA (US); Patricia Young, Los Angeles, CA (US); Alex Vasuthasawat, Los Angeles, CA (US); Kham M. Trinh, Alhambra, CA (US); Sherie Leaver Morrison, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 992 days.

(21) Appl. No.: 15/733,623

(22) PCT Filed: Mar. 18, 2019

(86) PCT No.: PCT/US2019/022813
§ 371 (c)(1),
(2) Date: Sep. 17, 2020

(87) PCT Pub. No.: WO2019/182996
PCT Pub. Date: Sep. 26, 2019

(65) Prior Publication Data
US 2021/0087249 A1    Mar. 25, 2021

Related U.S. Application Data

(60) Provisional application No. 62/645,061, filed on Mar. 19, 2018.

(51) Int. Cl.
*C07K 14/56* (2006.01)
*A61K 38/21* (2006.01)
*A61K 39/395* (2006.01)
*A61K 40/11* (2025.01)
*A61K 40/31* (2025.01)
*A61K 40/42* (2025.01)
*A61P 35/00* (2006.01)
*C07K 16/28* (2006.01)

(52) U.S. Cl.
CPC ............ *C07K 14/56* (2013.01); *A61K 38/212* (2013.01); *A61K 39/3955* (2013.01); *A61K 39/39558* (2013.01); *A61K 40/11* (2025.01); *A61K 40/31* (2025.01); *A61K 40/4211* (2025.01); *A61P 35/00* (2018.01); *C07K 16/2803* (2013.01); *C07K 16/2887* (2013.01); *A61K 2239/48* (2023.05); *C07K 2317/24* (2013.01); *C07K 2317/526* (2013.01); *C07K 2317/73* (2013.01); *C07K 2317/76* (2013.01); *C07K 2319/30* (2013.01)

(58) Field of Classification Search
CPC .... C07K 14/56; C07K 16/2887; C07K 14/57; C07K 14/565; A61K 38/212; A61K 39/4631; A61K 39/464412; A61K 38/21; A61K 38/215; A61K 38/217; A61K 40/11; A61K 40/31; A61K 40/4211; A61K 40/03; A61P 35/00
See application file for complete search history.

(56) References Cited

U.S. PATENT DOCUMENTS

| | | | |
|---|---|---|---|
| 8,258,263 B2 | 9/2012 | Morrison et al. | |
| 8,563,692 B2 | 10/2013 | Morrison et al. | |
| 8,629,246 B2 * | 1/2014 | Humphreys | A61P 37/06 530/387.3 |
| 9,139,634 B2 * | 9/2015 | Morrison | A61K 47/6851 |
| 9,522,958 B2 | 12/2016 | Epstein et al. | |
| 10,182,984 B2 | 1/2019 | Morrison et al. | |
| 2022/0177598 A1 | 6/2022 | Trinh et al. | |

FOREIGN PATENT DOCUMENTS

| | | |
|---|---|---|
| WO | WO-2009039409 A1 | 3/2009 |
| WO | WO-2013167136 A1 | 11/2013 |
| WO | WO-2019051204 A1 | 3/2019 |

OTHER PUBLICATIONS

U.S. Appl. No. 15/789,828, 10.*
Xuan, C. et al., Targeted delivery of interferon-alpha via fusion to anti-CD20 results in potent antitumor activity against B-cell lymphoma, https://doi.org/10.1182/blood-2009-10-250555 (Year: 2010).*
Briggs, B.,New approach aims to restore immune-powering B cells in cancer patients following successful immunotherapy with CAR T cells, Fred Hutch Cancer Centers, from:https://www.fredhutch.org/en/news/center-news/2016/10/depleting-car-t-cells-after-tumor-treatment-reverses-b-cell-deficiency.html (Year: 2016).*

(Continued)

*Primary Examiner* — Gregory S Emch
*Assistant Examiner* — Ashley H. Gao
(74) *Attorney, Agent, or Firm* — Norton Rose Fulbright US LLP

(57) ABSTRACT

In various embodiments methods are provided that involve the use of antibody-interferon (Ab-IFN) fusion proteins to boost the cancer-fighting capacity of adoptive T cell therapies (ACT), including any T cells that are manipulated and grown outside the body, then returned to the patient with the goal of having the infused T cells home to sites of tumor and destroy the cancer in an immunologic attack. Illustrative, but non-limiting, adoptive T cell therapies include chimeric antigen receptor (CAR) T cells, tumor-infiltrating lymphocytes (TILs), virus-specific T cells, and T cell receptor transgenic T cells.

13 Claims, 21 Drawing Sheets
Specification includes a Sequence Listing.

(56) References Cited

OTHER PUBLICATIONS

Wantanabe, K. et al, Target Antigen Density Governs the Efficacy of Anti-CD20-CD28-CD3 ζ Chimeric Antigen Receptor-Modified Effector CD8+ T Cells, https://doi.org/10.4049/jimmunol.1402346 (Year: 2015).*
Huber, JP, Regulation of effector and memory T-cell functions by type I interferon. Immunology. Apr. 2011;132(4):466-74. doi: 10.1111/j.1365-2567.2011.03412.x. (Year: 2011).*
Trinh, KR, Anti-CD20-interferon-β fusion protein therapy of murine B cell lymphomas, doi: 10.1097/CJI.0b013e3182993eb9 (Year: 2014).*
Wood, A.M., Pharmacology and Pharmacokinetics of Rituximab, retrieved from:https://www.medscape.com/viewarticle/406941_8?form=fpf (Year: 2001).*
Armitage (How I treat patients with diffuse large B-cell lymphoma, Blood (2007) 110 (1): 29-36 (2007) (Year: 2007).*
Lawrence (CD19 CAR T-Cell Therapy Effective for Relapsed/Refractory DLBCL, retrieved from: https://www.cancernetwork.com/view/cd19-car-t-cell-therapy-effective-relapsedrefractory-dlbcl (2017) (Year: 2017).*
Allison et al., Heterogeneity and Cancer, retrieved from: https://www.cancernetwork.com/view/heterogeneity-and-cancer (2014) (Year: 2014).*
American Cancer Society (Can Cancer be Cured?, American Cancer Society, retrieved from: https://www.cancer.org/cancer/understanding-cancer/can-cancer-be-cured.html)(2021) (Year: 2021).*
Forsthuber et al (B cell-based therapies in CNS autoimmunity: differentiating CD19 and CD20 therapeutic targets, https://doi.org/10.1177/17562864187616 (2018)) (Year: 2018).*
Hervas-Stubbs et al (CD8 T cell priming in the presence of IFN-α renders CTLs with improved responsiveness to homeostatic cytokines and recall antigens: important traits for adoptive T cell therapy. J Immunol. Oct. 1, 2012;189(7):3299-310. doi: 10.4049/jimmunol.1102495) (Year: 2012).*
Knochenderfer et al (B-cell depletion and remissions of malignancy along with cytokine-associated toxicity in a clinical trial of anti-CD19 chimeric-antigen-receptor-transduced T cells. Blood. Mar. 22, 2012;119(12):2709-20. doi: 10.1182/blood-2011-10-384388) (Year: 2011).*
Borden, E C., et al., "Second-generation Interferons for Cancer," Seminars in Cancer Biology, 2000, vol. 10(2), pp. 125-144.
Brentjens, R., et al., "CD19-Targeted T Cells Rapidly Induce Molecular Remissions in Adults with Chemotherapy-Refractory Acute Lymphoblastic Leukemia," Science Translational Medicine, 2013, vol. 5(177):177ra38, pp. 1-8.
Cooper, L J N., et al.," T-Cell Clones can be Rendered Specific for CD19: Toward the Selective Augmentation of the Graft-versus-B-lineage Leukemia Effect," Blood, 2003, vol. 101(4), pp. 1637-1644.
Crouse, J., et al.,. Type I Interferons Protect T Cells Against NK Cell Attack Mediated by the Activating Receptor NCR1. Immunity, 2014, vol. 40(6), pp. 961-973.
Davila, M L., "Efficacy and Toxicity Management of 19-28z CAR T Cell Therapy in B Cell Acute Lymphoblastic Leukemia," Science Translational Medicine, 2014, vol. 6(224):224ra25, pp. 1-10.
De Oliveira, S N., et al., "Modification of Hematopoietic Stem/Progenitor Cells with CD19-Specific Chimeric Antigen Receptors as a Novel Approach for Cancer Immunotherapy," Human Gene Therapy, 2013, vol. 24(10), pp. 824-839.
Escobar, G., et al. "Genetic Engineering of Hematopoiesis for Targeted IFN-o Delivery Inhibits Breast Cancer Progression," Science Translational Medicine, Jan. 1, 2014, vol. 6(217), pp. 1-14.
Escobar, G., et al., "Interferon Gene Therapy Reprograms the Leukemia Microenvironment Inducing Protective Immunity to Multiple Tumor Antigens," Nature Communications, Jul. 24, 2018, vol. 9(1):2896, pp. 1-16.
International Preliminary Report on Patentability and Written Opinion dated Oct. 1, 2020 in PCT Application No. PCT/US2019/022813.
International Search Report and Written Opinion dated May 14, 2019 in PCT Application No. PCT/US2019/022813.
Kershaw, M H., et al., "Gene-engineered T Cells for Cancer Therapy," Nature Reviews. Cancer, 2013, vol. 13(8), pp. 525-541.
Kochenderfer, J N., et al.,. "Chemotherapy-Refractory Diffuse Large B-Cell Lymphoma and Indolent B-Cell Malignancies can be Effectively Treated with Autologous T Cells Expressing an Anti-CD19 Chimeric Antigen Receptor,", Journal of Clinical Oncology, 2015, vol. 33(6), pp. 540-549.
Lavoie, T B., et al., "Binding and Activity of all Human Alpha Interferon Subtypes," Cytokine, 2011, vol. 56(2), pp. 282-289.
Lee, D W., et al.,. "Current Concepts in the Diagnosis and Management of Cytokine Release Syndrome," Blood, 2014, vol. 124(2), pp. 188-195.
Papewalis, C., et al., "IFN-Alpha Skews Monocytes into CD56+-Expressing Dendritic Cells with Potent Functional Activities in Vitro and In vivo," Journal of Immunology, 2008, vol. 180(3), pp. 1462-1470.
Parker, B S., et al., "Antitumour Actions of Interferons: Implications for Cancer Therapy," Nature Reviews. Cancer, 2016, vol. 16(3), pp. 131-144.
Porter, D L., et al., "Chimeric Antigen Receptor T Cells Persist and Induce Sustained Remissions in Relapsed Refractory Chronic Lymphocytic Leukemia," Science Translational Medicine, 2015, vol. 7(303):303ra139, pp. 1-13.
Slaney, C Y., et al., "Trafficking of T cells into tumors," Cancer Research, 2014, vol. 74(24), pp. 7168-7174.
Xu, H C., et al., "Type I Interferon Protects Antiviral CD8+ T Cells from NK Cell Cytotoxicity," Immunity, 2014, vol. 40(6), pp. 949-960.
Xu, X J., et al., "Cytokine Release Syndrome In Cancer Immunotherapy with Chimeric Antigen Receptor Engineered T Cells," Cancer Letters, 2014, vol. 343(2), pp. 172-178.
Yoo, E M., et al., "Anti-CD138-Targeted Interferon is a Potent Therapeutic Against Multiple Myeloma," Journal of Interferon and Cytokine Research, 2015, vol. 35(4), pp. 281-291.
Young, P A., et al., "Antibody-Cytokine Fusion Proteins for Treatment of Cancer: Engineering Cytokines for Improved Efficacy and Safety," Seminars in Oncology, 2014, vol. 41(5), pp. 623-636.
Young, P A., et al., "Antibody-Interferon-Alpha Fusion Protein (IGN002) for the Treatment of B-Cell Non-Hodgkin Lymphomas: A Phase 1, First-in-Human, Dose-Escalation Trial," Journal of Clinical Oncology, 2016, vol. 34(15), 2 Pages. (suppl; abstr TPS3109).
Zitvogel, L., et al., "Type I Interferons in Anticancer Immunity," Nature Reviews. Immunology, 2015, vol. 15(7), pp. 405-414.

* cited by examiner (A)

(B)

(C)
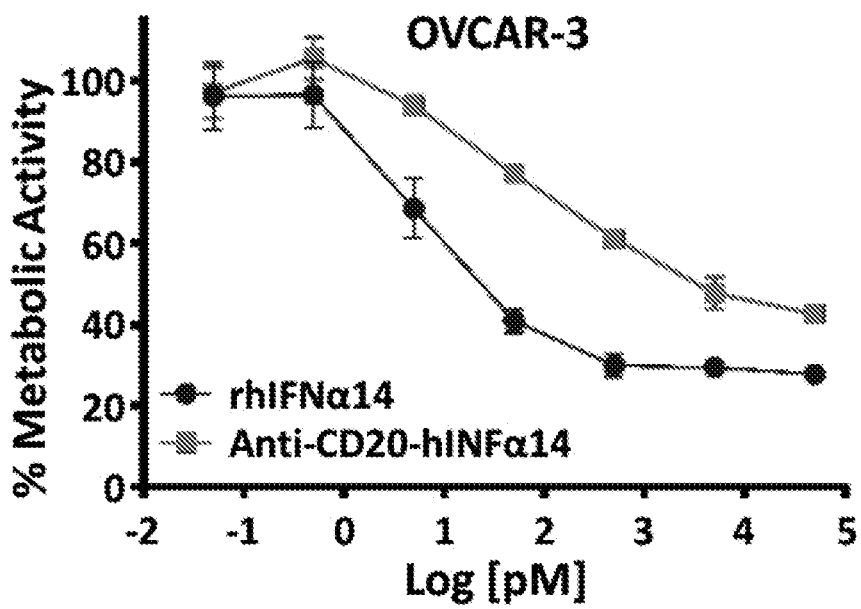
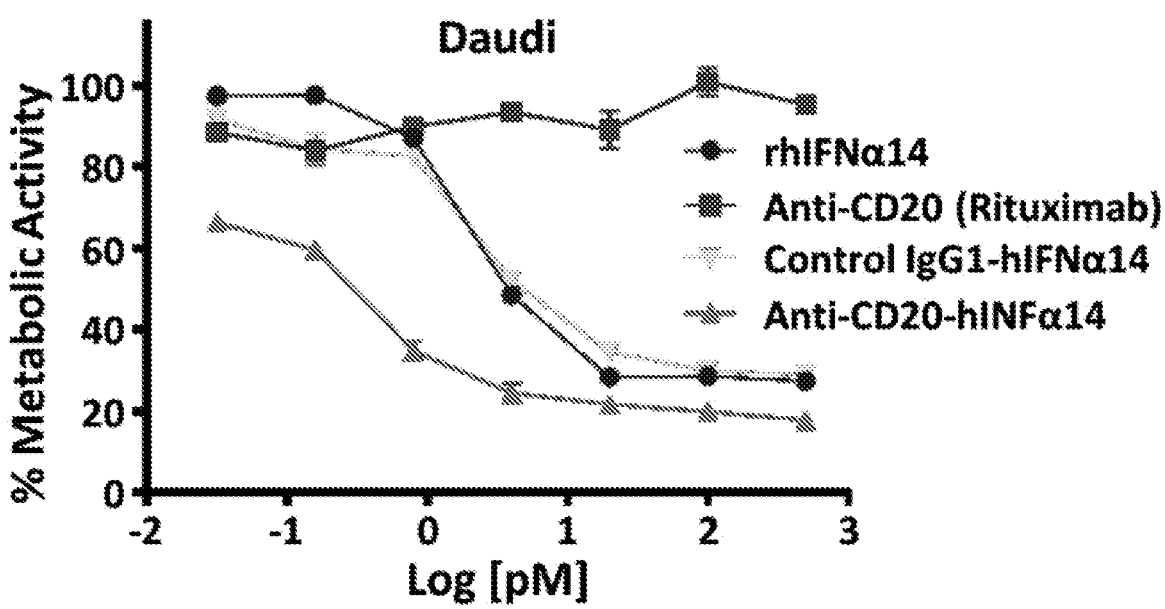
*Fig. 2, cont'd.*

(D)
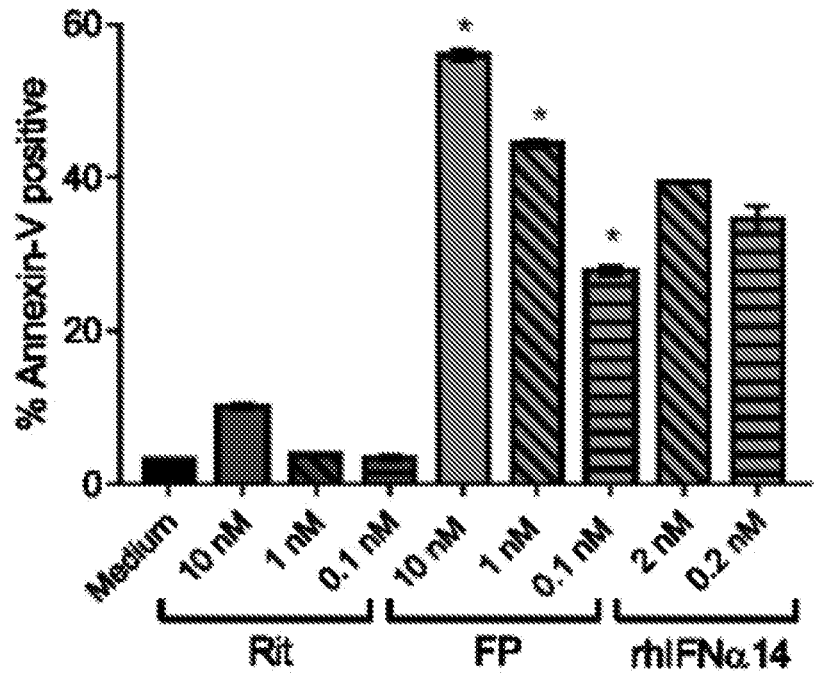
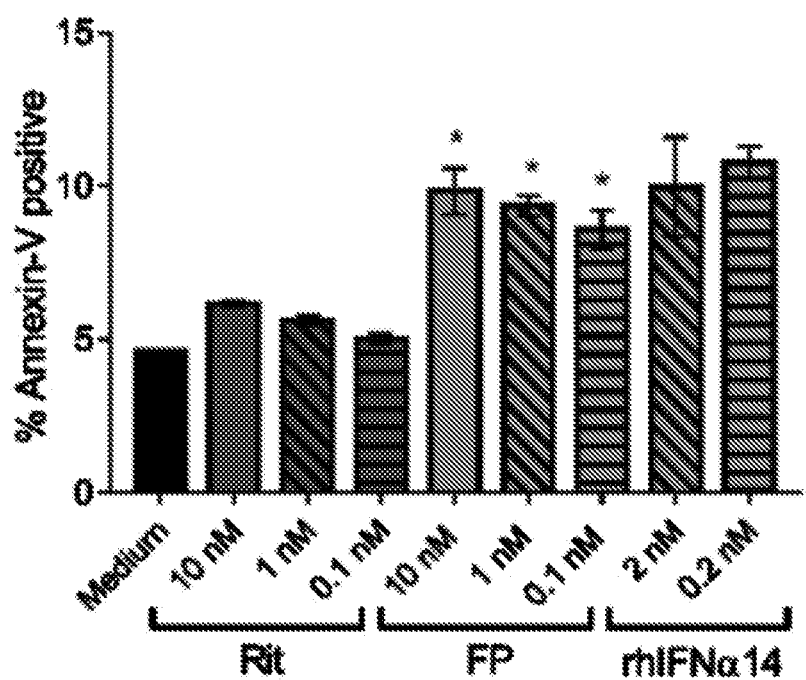
Fig. 2, cont'd.

(D, cont'd.)
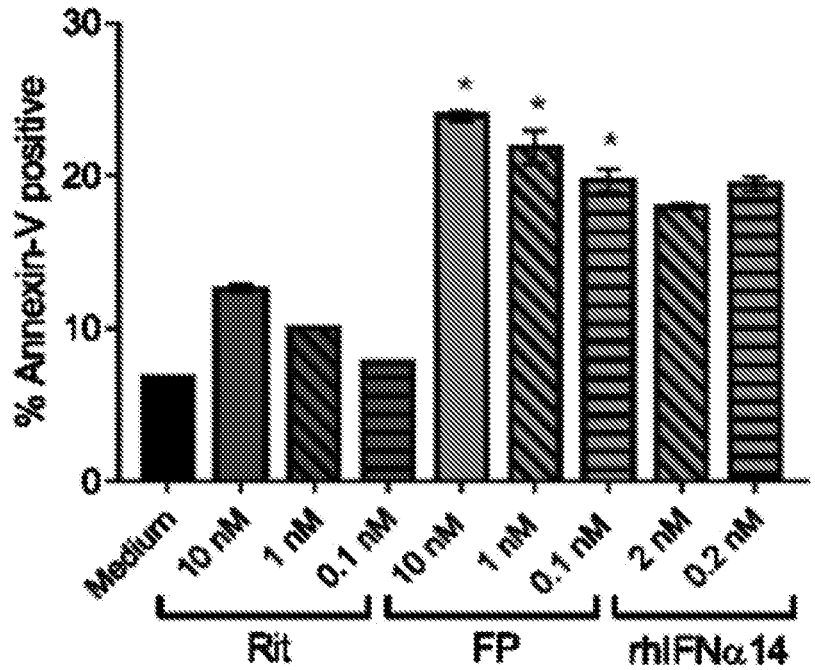
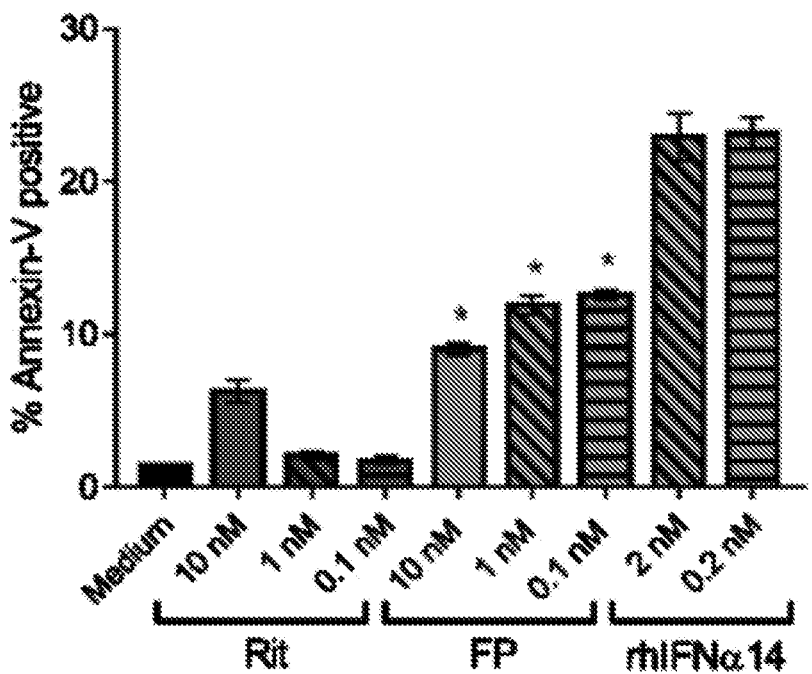
*Fig. 2, cont'd.*

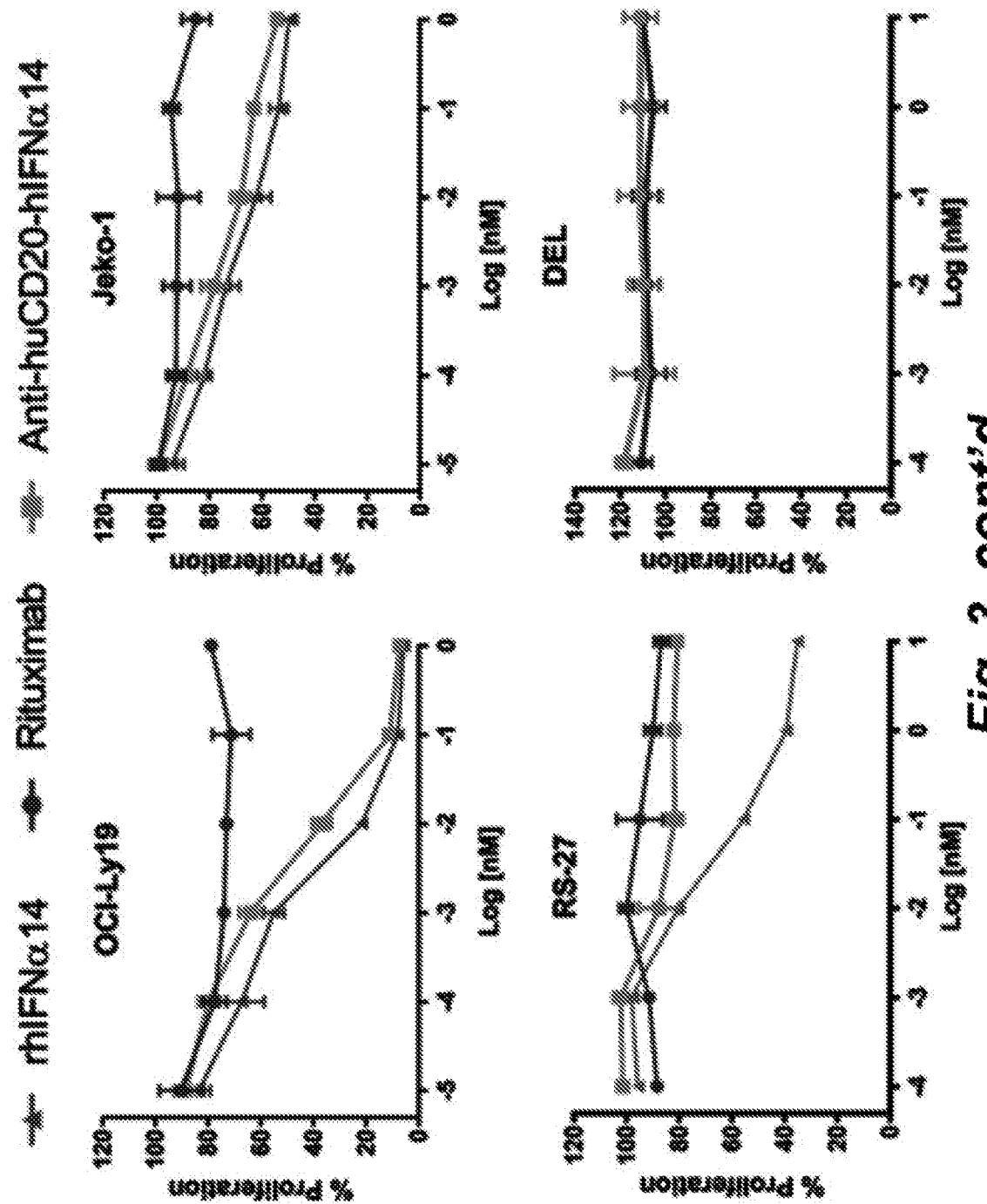
Fig. 3, cont'd.

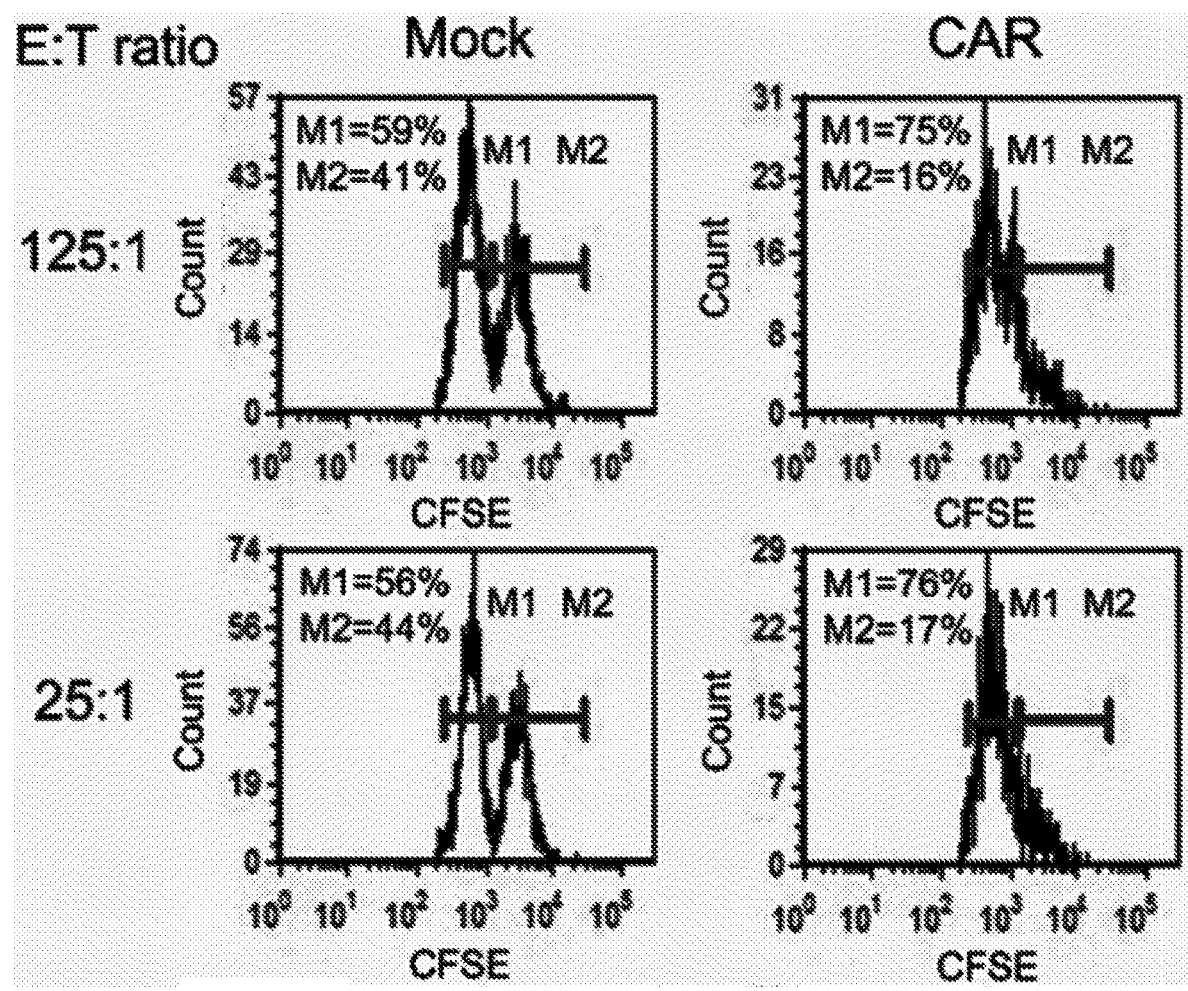
Fig. 4, cont'd.

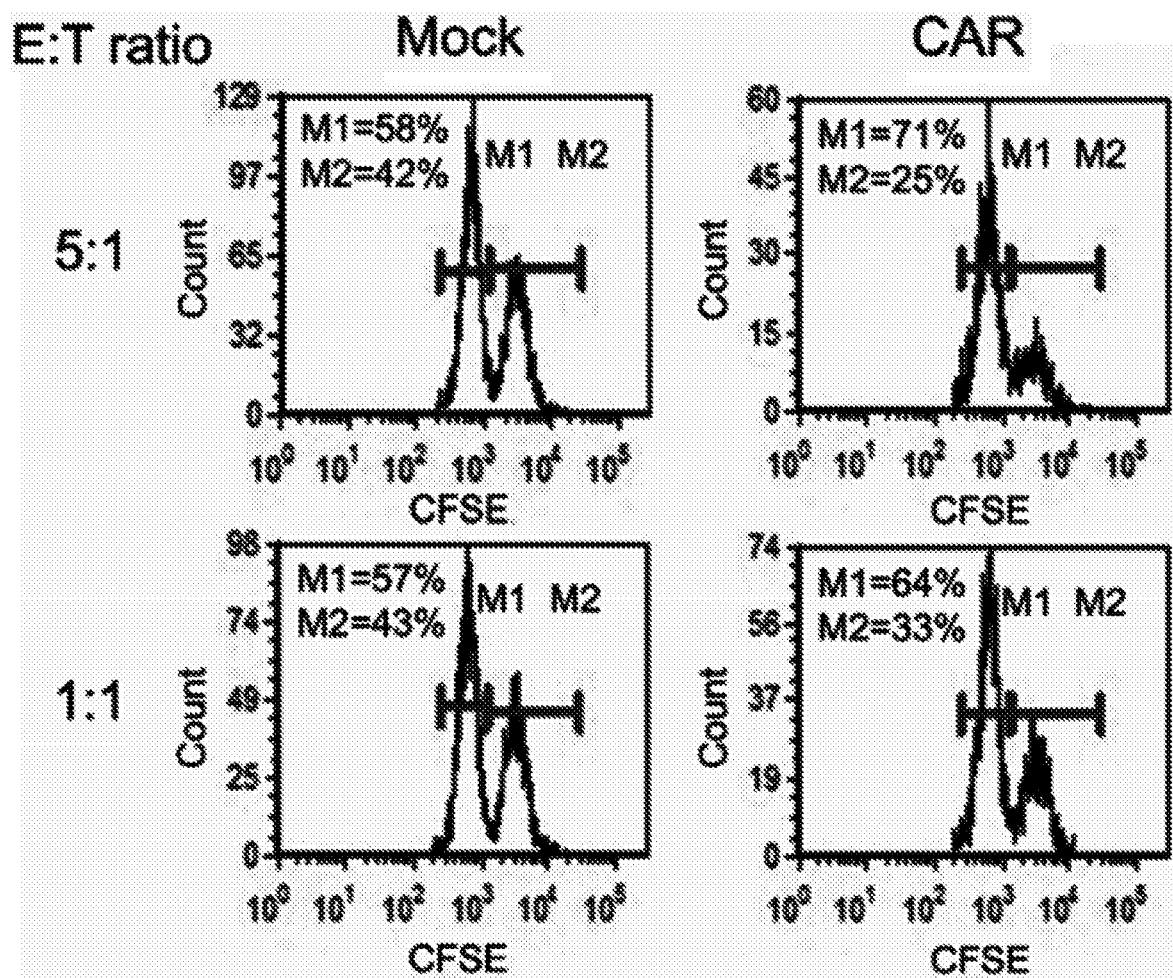
Fig. 4, cont'd

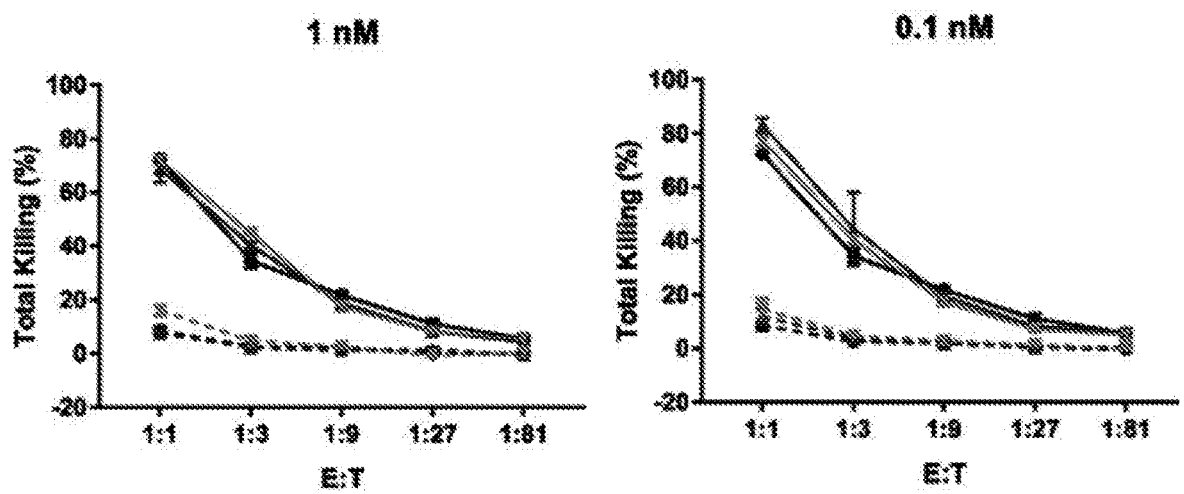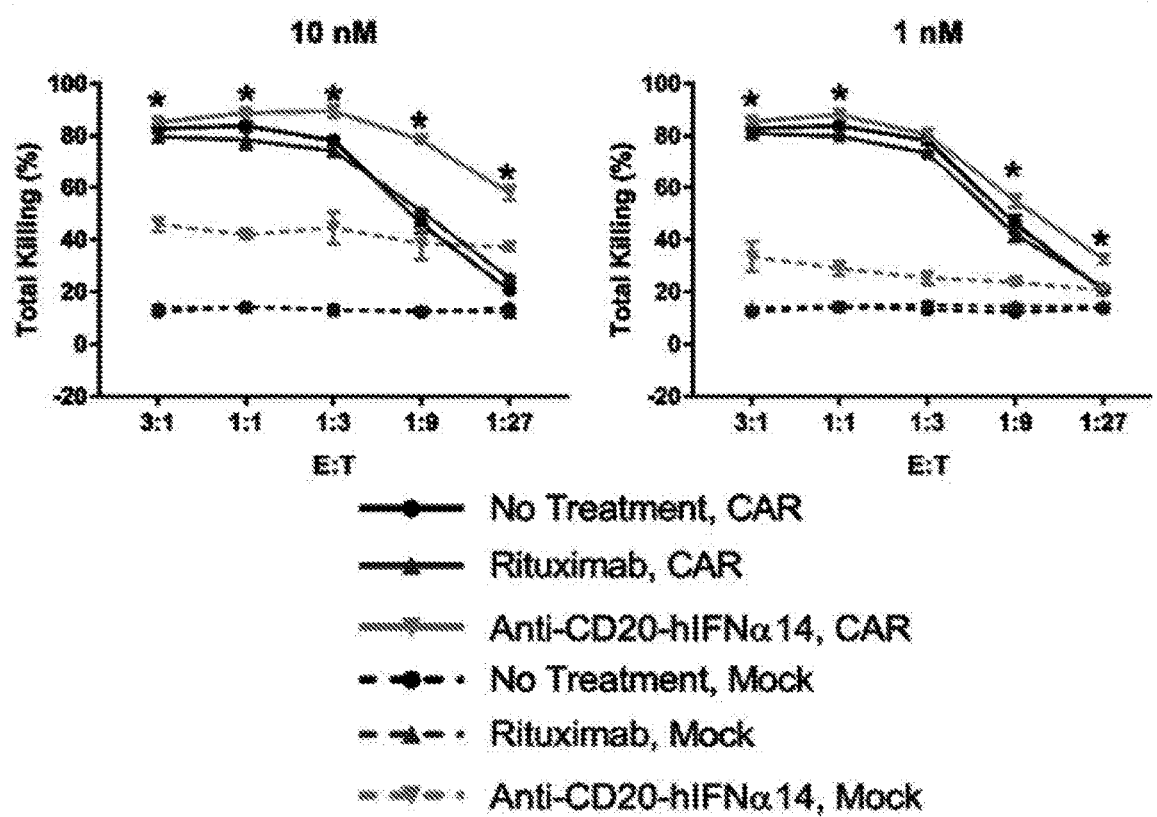
Fig. 5, cont'd.

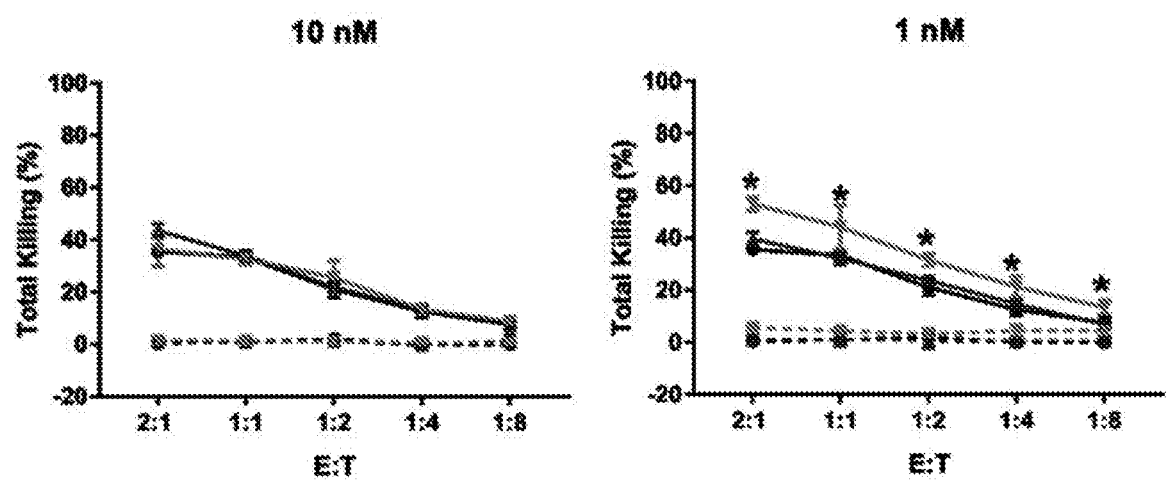
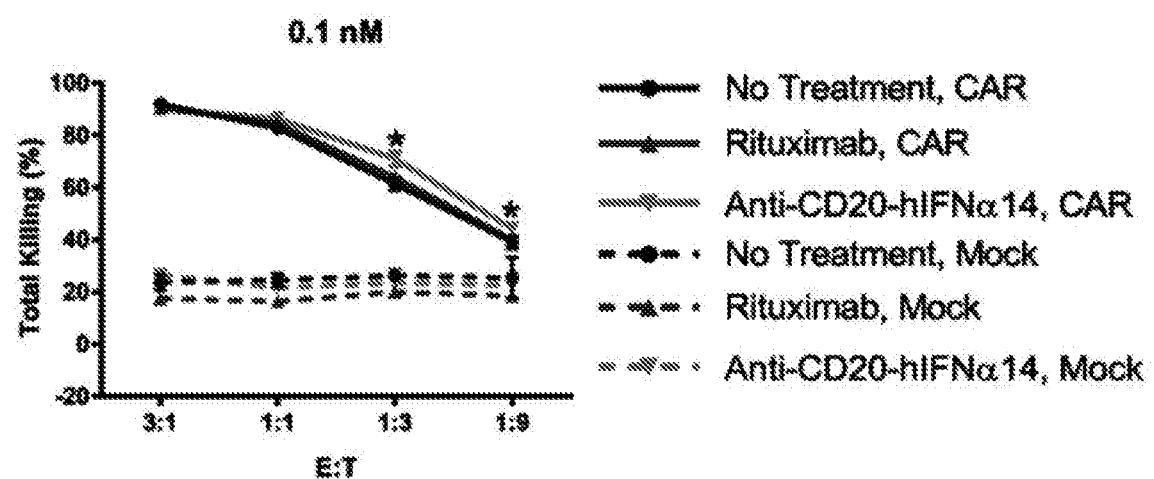
Fig. 5, cont'd.

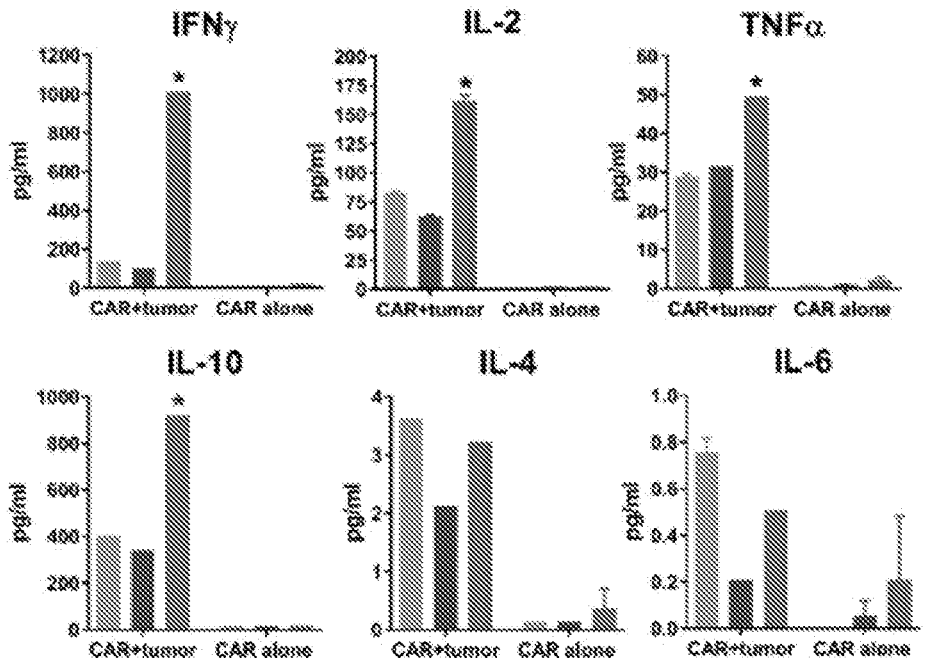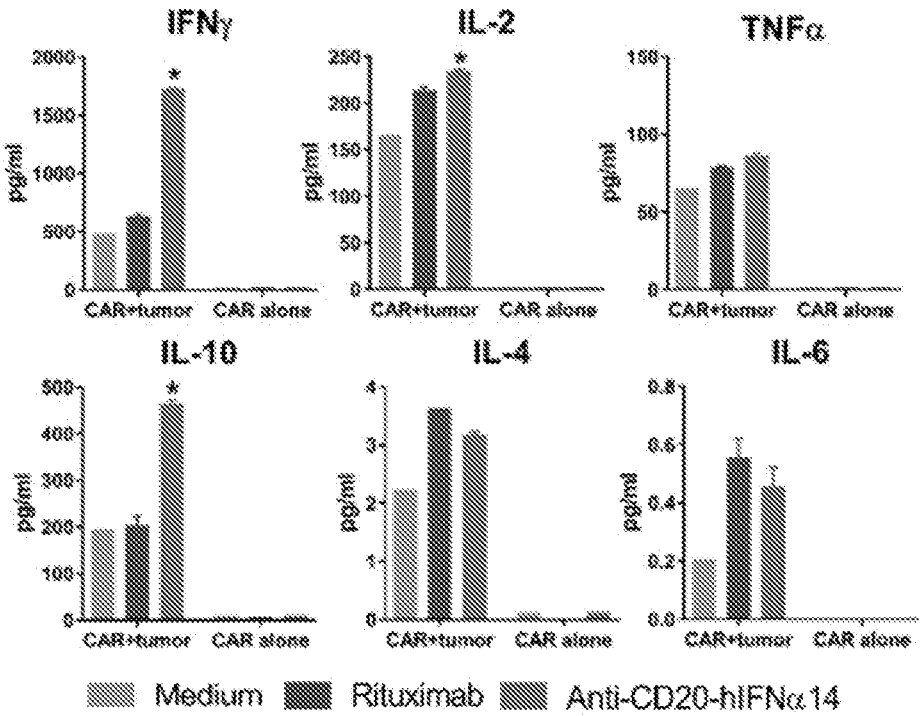
*Fig. 7, cont'd.*

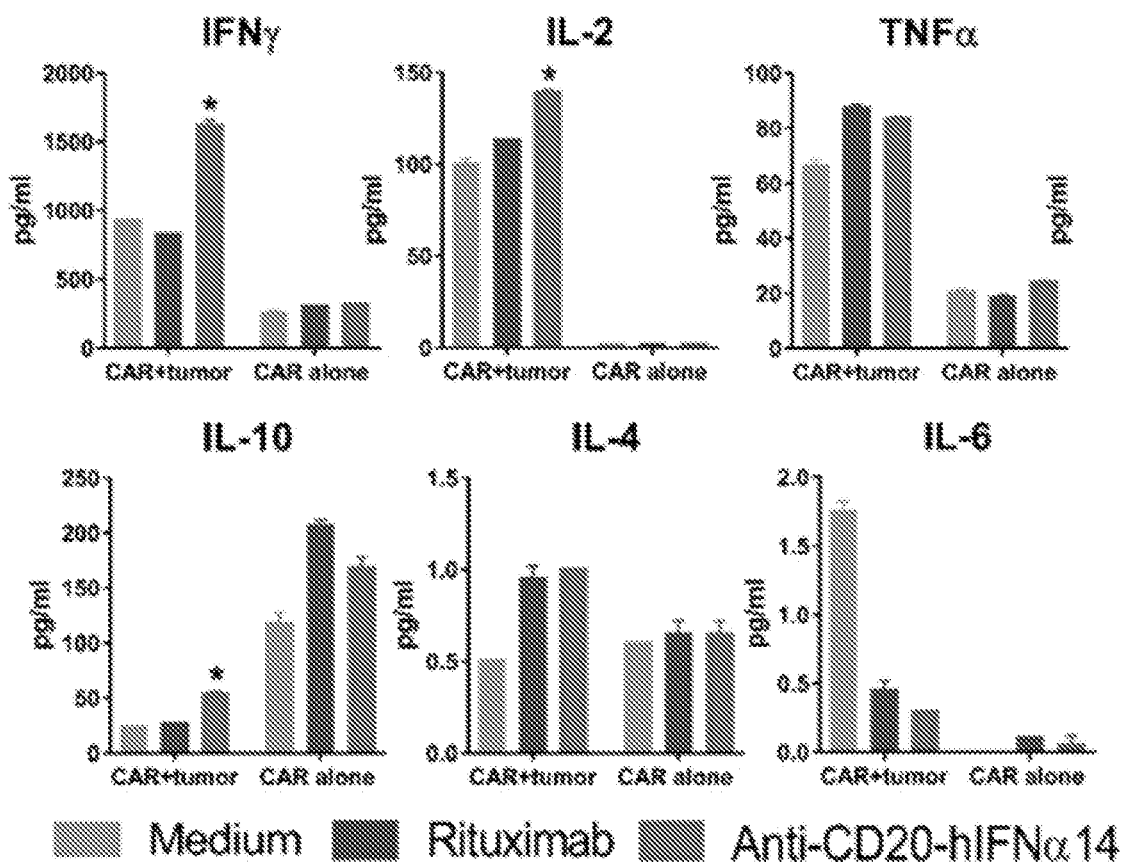
Fig. 7, cont'd.

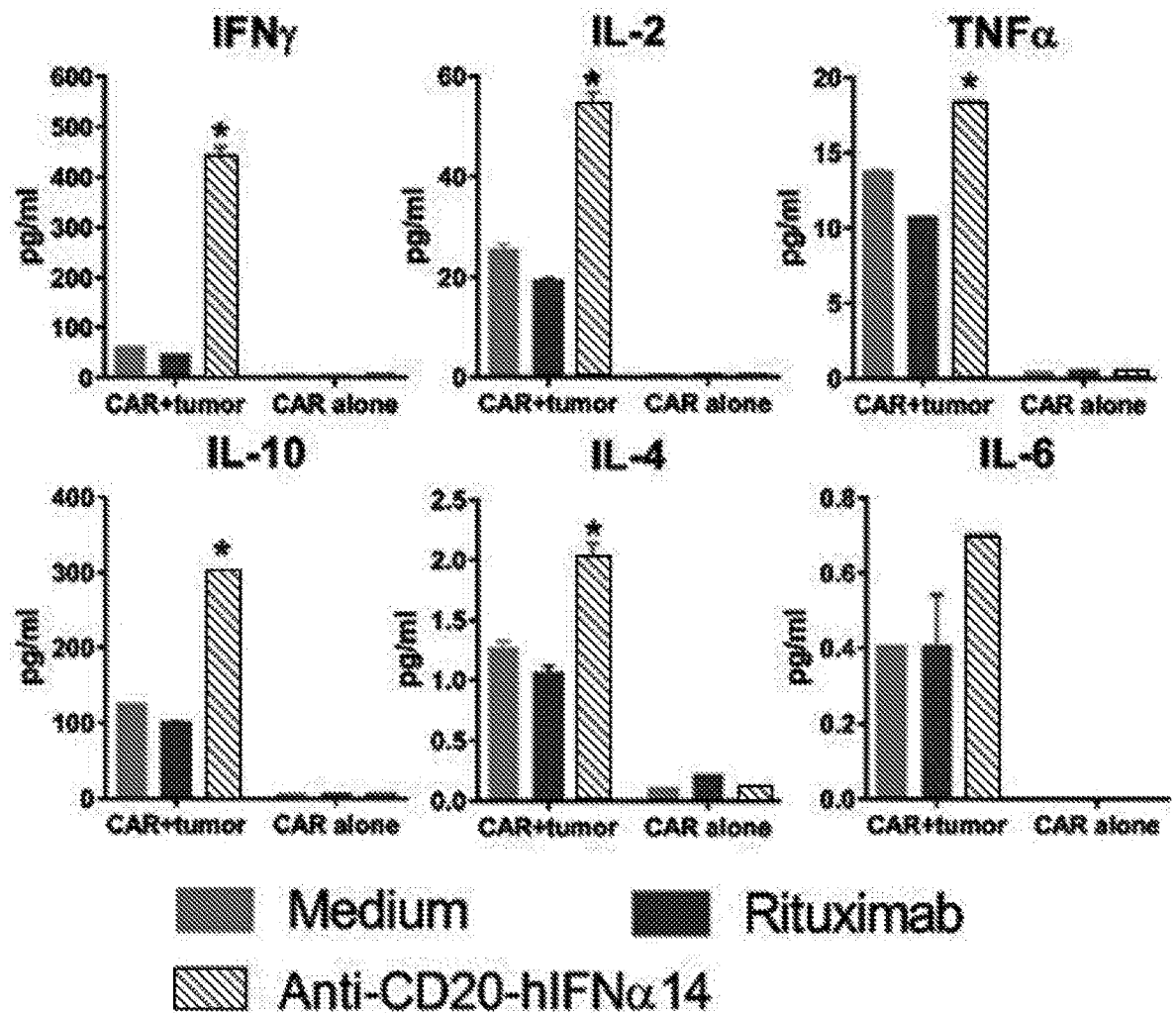
Fig. 8, cont'd.

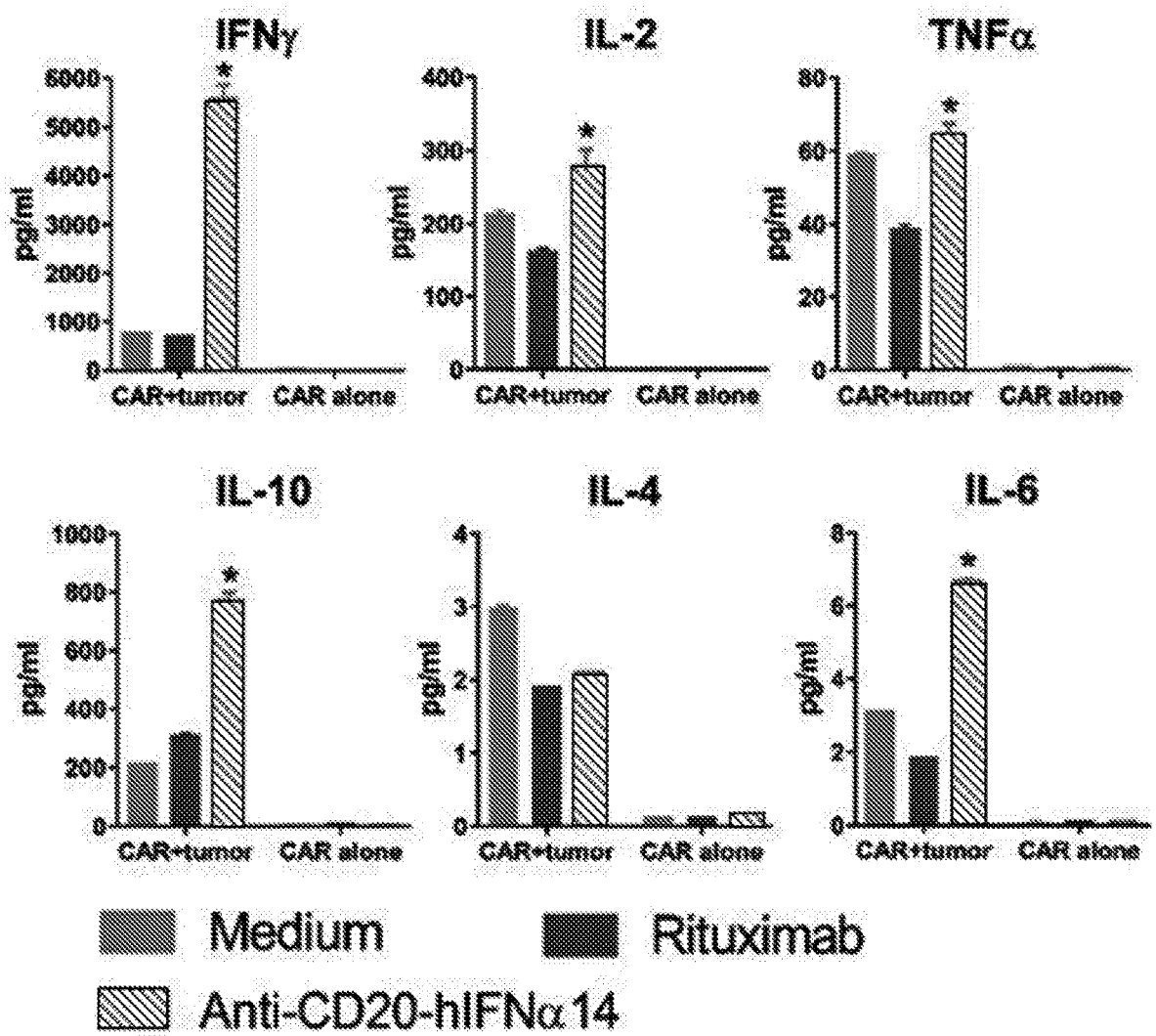
Fig. 8, cont'd.

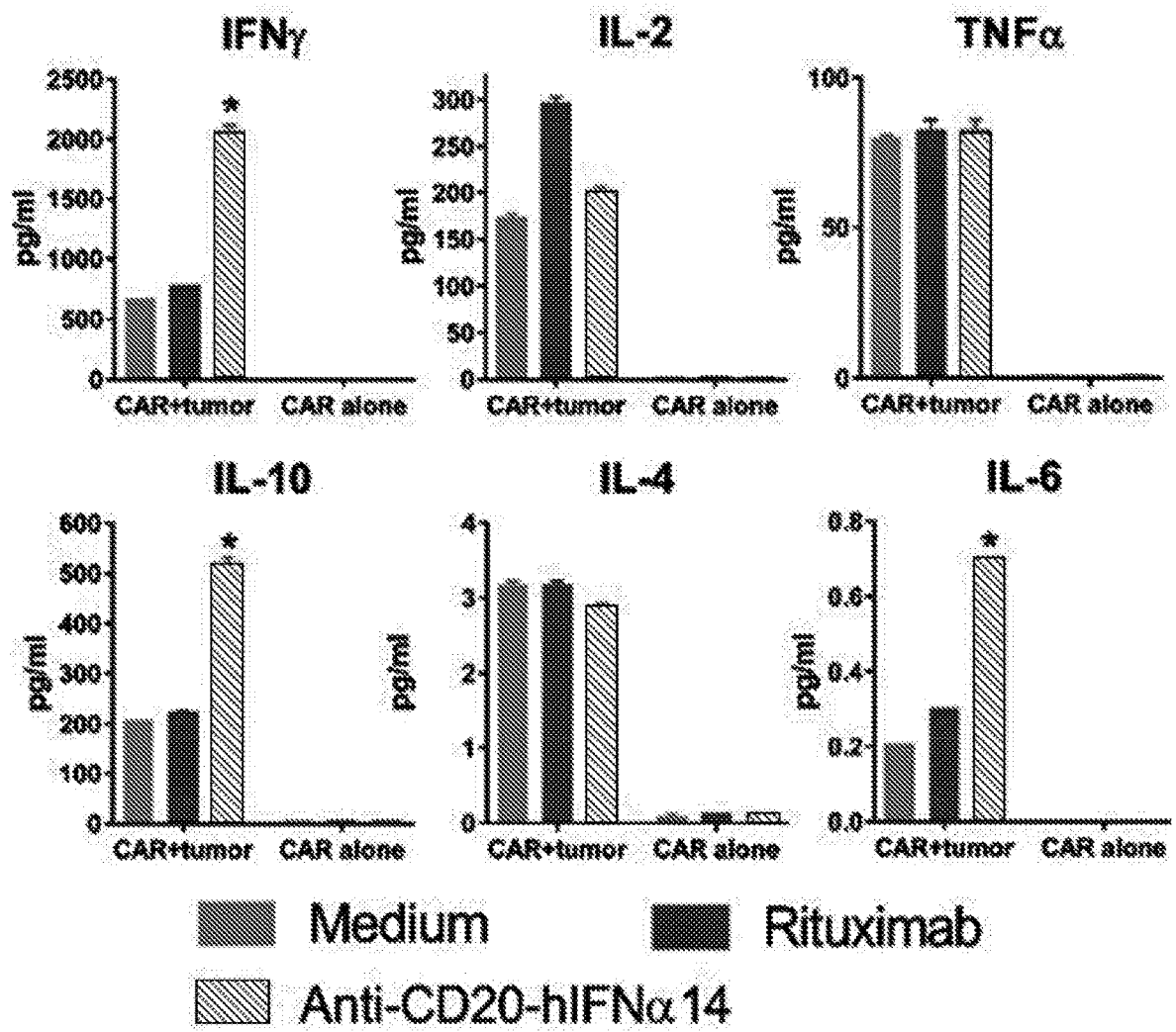
Fig. 8, cont'd.

ANTIBODY-INTERFERON FUSION PROTEINS FOR ENHANCING ADOPTIVE T CELL THERAPIES FOR THE TREATMENT OF CANCER

CROSS-REFERENCE TO RELATED APPLICATIONS

This application is a national stage application, filed under 35 U.S.C. § 371, of International Patent Application No. PCT/US2019/022813, filed on Mar. 18, 2019, which claims benefit of and priority to U.S. Ser. No. 62/645,061, filed on Mar. 19, 2018, both of which are incorporated herein by reference in their entirety for all purposes.

STATEMENT OF GOVERNMENTAL SUPPORT

This invention was made with government support under Grant Numbers CA162964 and CA200910, awarded by the National Institutes of Health. The government has certain rights in the invention.

INCORPORATION BY REFERENCE OF SEQUENCE LISTING PROVIDED AS A TEXT FILE

This application contains references to nucleic acid sequences that have been submitted concurrently herewith as the sequence listing text file "UCLA-P199US_ST25.txt", file size 45.6 kb, created on 11/24/2020, which is incorporated by reference in its entirety pursuant to 37 C.F.R. § 1.52(e)(5).

BACKGROUND

Adoptive cell therapy (ACT) is a revolutionary form of immunotherapy in anti-cancer treatment, which includes chimeric antigen receptors (CARs). CARs are recombinant proteins with antigen recognition moieties and T cell activation domains that can be expressed by host T cells via retroviral transduction. The resulting CAR T cell can redirect the specificity of the T cell to a tumor-associated antigen. Specifically, the treatment of patients with CD19 CAR T cells has elicited objective tumor responses with tolerable toxicities reported thus far resulting in approval for use in acute lymphoblastic leukemia (ALL) and diffuse large B cell lymphoma (DLBCL) (Abramson and others 2017; Brentjens and others 2013; Kochenderfer and others 2015; Neelapu and others 2017; Schuster and others 2017; Turtle and others 2016). Despite the initial success with response rates in non-Hodgkin lymphoma (NHL) ranging between 59-84% (Abramson and others 2017; Schuster and others 2017), longer follow-up has shown that the majority of patients relapse by 3-6 months (Abramson and others 2017; Neelapu and others 2017). Thus, given the limited durability of CAR T cell therapy, further studies are warranted to induce a sustained treatment response.

Interferons (IFNs) have both antiviral and immunostimulatory properties, acting as essential mediators of anti-cancer immunity (Parker and others 2016). IFN enhances CD8+ T cell cytotoxicity, dendritic cell maturation (Papewalis and others 2008), protects T cells from NK cell attack (Crouse and others 2014; Xu and others 2014), and suppresses regulatory T cells (Bacher and others 2013). Furthermore, type I IFNs increase T cell infiltration into tumors, recognition of lymphoma cells, and promotes survival of memory T cells (Zitvogel and others 2015). Antibody-targeted therapy harnesses the specificity of monoclonal antibodies to direct immunotherapeutic agents, such as IFN, directly to the tumor site thereby minimizing systemic toxicity while maximizing the properties of IFN as an anti-cancer agent (Young and others 2014). Anti-CD20-IFN fusion proteins were developed in our laboratory, and previously have been shown to have superior anti-tumor effects in vitro and in vivo in both mouse and xenograft lymphoma models. Importantly, the anti-tumors effects could be achieved without systemic toxicity (Trinh and others 2013; Xuan and others 2010). A first-in-human phase I study of anti-CD20-hIFNα2 (IGN002) is now ongoing (NCT02519270) (Young and others 2016).

SUMMARY

In various embodiments methods are provided that involve the use of antibody-interferon (Ab-IFN) fusion proteins to boost the cancer-fighting capacity of adoptive T cell therapies (ACT), including any T cells that are manipulated and grown outside the body, then returned to the patient with the goal of having the infused T cells home to sites of tumor and destroy the cancer in an immunologic attack. Illustrative, but non-limiting, adoptive T cell therapies include chimeric antigen receptor (CAR) T cells, tumor-infiltrating lymphocytes (TILs), virus-specific T cells, and T cell receptor transgenic T cells. By treating the patient with antibody-IFN fusion proteins either before, during, or after adoptive T cell therapies, the IFN reaching the tumor sites can result in immunologic reactions that can A) weaken the tumor cells by inhibiting their growth, and/or B) alter expression of cell surface molecules on tumor cells that make them more recognizable to T cells (ex: adhesion, costimulation and HLA molecules), and/or C) induce local production of other cytokines and chemokines that promote T cell infiltration into tumors, and D) activate T cells localizing to the tumor site to attain more potent cytolytic functions (see, e.g., FIG. 1).

Accordingly, various embodiments contemplated herein may include, but need not be limited to, one or more of the following:

Embodiment 1: A method of treating a cancer in a mammal, said method comprising:
 administering to said mammal a targeted interferon where said targeted interferon comprises an interferon attached to an antibody that binds to a cell surface marker of said cancer; and administering to said mammal an adoptive T cell therapy targeted to said cancer.

Embodiment 2: A method of improving efficacy of an adoptive T cell therapy directed against a cancer in a mammal, said method comprising:
 administering to a mammal receiving said adoptive T cell therapy a targeted interferon where said targeted interferon comprises an interferon attached to an antibody that binds to a cell surface marker of said cancer.

Embodiment 3: The method according to any one of embodiments 1-2, wherein said targeted interferon improves recognition of tumor cells, and/or cytotoxicity, and/or activation and survival of an adoptive T cell therapeutic as compared to the use of said adoptive T cell therapeutic in the absence of said targeted interferon.

Embodiment 4: The method according to any one of embodiments 1-3, wherein said adoptive T cell therapy comprises use of a therapeutic selected from the group consisting of a chimeric antigen receptor (CAR) T cell, a tumor infiltrating lymphocyte (TIL), a virus-specific T cell, a tumor-reactive T cell derived from the peripheral blood, and a T cell receptor transgenic T cell.

Embodiment 5: The method of embodiment 4, wherein said adoptive T cell therapy comprise use of a chimeric antigen receptor (CAR) T cell.

Embodiment 6: The method of embodiment 4, wherein said adoptive T cell therapy comprises use of a T cell receptor transgenic T cell.

Embodiment 7: The method of embodiment 4, wherein said adoptive T cell therapy comprise use of a tumor infiltrating lymphocyte (TIL).

Embodiment 8: The method according to any one of embodiments 1-7, wherein said targeted interferon is administered prior to said adoptive T cell therapy.

Embodiment 9: The method of embodiment 8, wherein said adoptive T cell therapy is administered 30 days or less after administration of said targeted interferon.

Embodiment 10: The method according to any one of embodiments 1-7, wherein said targeted interferon is administered at the same time as said adoptive T cell therapy.

Embodiment 11: The method according to any one of embodiments 1-10, wherein said cancer comprises a cancer selected from the group consisting of a B cell lymphoma, a T cell lymphoma, a Hodgkin lymphoma, a B cell leukemia, a T cell leukemia, a myeloid leukemia, lung cancer, a bronchus cancer, a colorectal cancer, a prostate cancer, a breast cancer, a pancreas cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, a adrenal gland cancer, an osteosarcoma, a chondrosarcoma, a liposarcoma, a testes cancer, and a malignant fibrous histiocytoma.

Embodiment 12: The method of embodiment 11, wherein said cancer comprises a cancer selected from the group consisting of acute lymphoblastic leukemia (ALL) or diffuse large B cell lymphoma (DLBCL), or other non-Hodgkin lymphoma (NHL) including Burkitt, primary mediastinal, mantle cell, small lymphocytic, lymphoplasmacytoid, marginal zone, transformed, or primary CNS.

Embodiment 13: The method according to any one of embodiments 1-6, 11, and 12, wherein said adoptive T cell therapy comprises a CAR-T cell, TIL, blood-derived T cell or a T cell receptor transgenic T cell comprising a T cell receptor that binds a cancer marker selected from the group consisting of CD20, CD19, BCMA, CSPG4, TNMuc1, ROR1, CD33, EGFRVIII, CD30, EGFR, FOLR1, HER2, HGFR, CAIX, CD22, EpCAM, GPC3, IL13Ru2, MSLN (mesothelin), CD138, CD38, HER2, CA 125, AFP, beta-hCG, carcinoembryonic antigen (CEA), bombesin, PSA, RET & BRAF mutation, EGFR, RET mutation (associated with MEN 2A/B), RAS (thyroid), CD46, CD55, CD59, MAGE, CD1, CD2, CD5, CD7, CD7, CD13, CD15, CD22, CD33, CD34, EGFR, HER2, MUC1, Tag-72, CD3, CD19, CD20, CD21, CD25, HLA-DR, CD19, CD21, CD25, Leu-M1, HMB 45, PSMA, SE10, GD2, NY-ESO-1 (CTAG1B), folate receptor alpha or beta, NKG2D ligands, CLEC12A, FLT3, CLL1, LeY, L1-CAM, CD70, CD116, CD123, and CD133.

Embodiment 14: The method according to any one of embodiments 1-4, and 10-12, wherein said adoptive T cell therapy comprises a tumor infiltrating lymphocyte (TIL) that is directed to a cancer that expresses one or more cancer markers selected from the group consisting of CD20, CD19, BCMA, CSPG4, TNMuc1, ROR1, CD33, EGFRVIII, CD30, EGFR, FOLR1, HER2, HGFR, CAIX, CD22, EpCAM, GPC3, IL13Ru2, MSLN (mesothelin), CD138, CD38, HER2, CA 125, AFP, b-hCG, carcinoembryonic antigen (CEA), bombesin, PSA, RET & BRAF mutation, EGFR, RET mutation (associated with MEN 2A/B), RAS (thyroid), CD19, CD20, CD46, CD55, CD59, MUC1, MAGE, CD1, CD2, CD5, CD7, CD7, CD13, CD15, CD33, CD34, EGFR, HER2, MUC1, Tag-72, CEA, CD3, CD19, CD20, CD21, CD25, HLA-DR, CD19, CD21, CD25, Leu-M1, HMB 45, PSMA, SE10, GD2, NY-ESO-1 (CTAG1B), folate receptor alpha or beta, NKG2D ligands, CLEC12A, FLT3, CLL1, LeY, L1-CAM, CD70, CD116, CD123, and CD133.

Embodiment 15: The method according to any one of embodiments 1-14, wherein said antibody attached to said interferon comprise an antibody that that binds to a cancer marker selected from the group consisting of CD20, CD19, BCMA, CSPG4, TNMuc1, ROR1, CD33, EGFRVIII, CD30, EGFR, FOLR1, HER2, HGFR, CAIX, CD22, EpCAM, GPC3, IL13Ru2, MSLN, CD138, CD38, HER2, CA 125, AFP, b-hCG, carcinoembryonic antigen (CEA), bombesin, PSA, RET & BRAF mutation, EGFR, RET mutation (associated with MEN 2A/B), RAS (thyroid), CD46, CD55, CD59, MUC1, MAGE, CD1, CD2, CD5, CD7, CD7, CD13, CD15, CD33, CD34, EGFR, HER2, MUC1, Tag-72, CEA, CD3, CD21, CD25, HLA-DR, CD19, CD21, CD25, Leu-M1, HMB 45, PSMA, SE10, GD2, NY-ESO-1 (CTAG1B), folate receptor alpha or beta, NKG2D ligands, CLEC12A, FLT3, CLL1, LeY, L1-CAM, CD70, CD116, CD123, and CD133.

Embodiment 16: The method according to any one of embodiments 1-15, wherein said antibody comprising said targeted interferon and said adoptive T cell therapeutic are directed to different cancer markers on the same cancer.

Embodiment 17: The method of embodiment 16, wherein said targeted interferon comprises an antibody that binds to CD20 and said adoptive T cell therapy targets a CD19.

Embodiment 18: The method of embodiment 16, wherein said targeted interferon comprises an antibody that binds to CD19 and said adoptive T cell therapy targets a CD20.

Embodiment 19: The method according to any one of embodiments 1-15, wherein said antibody comprising said targeted interferon and said adoptive T cell therapeutic are directed to the same cancer marker.

Embodiment 20: The method of embodiment 19, wherein said targeted interferon comprises an antibody that binds to CD20 and said adoptive T cell therapy targets a CD20.

Embodiment 21: The method of embodiment 19, wherein said targeted interferon comprises an antibody that binds to CD19 and said adoptive T cell therapy targets a CD19.

Embodiment 22: The method according to any one of embodiments 19-21, wherein said adoptive T cell therapy comprises a T cell whose targeting component comprises or is derived from the same antibody as the antibody comprising the targeted interferon.

Embodiment 23: The method according to any one of embodiments 1-22, wherein said antibody is an antibody comprising said targeted interferon comprises an antibody selected from the group consisting of a single chain Fv (scFv), a FAB, a (Fab')$_2$, an (scFv)$_2$, and a full immunoglobulin.

Embodiment 24: The method of embodiment 23, wherein said antibody is an scFv.

Embodiment 25: The method of embodiment 23, wherein said antibody is a full immunoglobulin.

Embodiment 26: The method of embodiment 25, wherein said antibody is selected from the group consisting of an IgG, an IgE, an IgA, an IgM, and an IgD.

Embodiment 27: The method of embodiment 26, wherein said antibody is an IgG.

Embodiment 28: The method according to any one of embodiments 1-27, wherein said interferon comprises an interferon selected from the group consisting of interferon alpha (IFNα), interferon beta (IFNβ), and interferon gamma (IFNγ).

Embodiment 29: The method of embodiment 28, wherein said interferon is an interferon-alpha (IFNα).

Embodiment 30: The method of embodiment 29, wherein said interferon is an interferon alpha subtype selected from the group consisting of IFNα14, IFNα2, IFNα1, IFNα4, IFNα5, IFNα6, IFNα7, IFNα8, IFNα10, IFNα13, IFNα16, IFNα17, IFNα21.

Embodiment 31: The method of embodiment 30, wherein said interferon is an IFN-α14.

Embodiment 32: The method of embodiment 30, wherein said interferon is an IFN-α2.

Embodiment 33: The method of embodiment 30, wherein said interferon is an IFN-α10.

Embodiment 34: The method of embodiment 28, wherein said interferon is an interferon-beta (IFNβ).

Embodiment 35: The method of embodiment 28, wherein said interferon is an interferon gamma (IFNγ).

Embodiment 36: The method of embodiment 35, wherein said interferon gamma is a full-length interferon gamma.

Embodiment 37: The method of embodiment 35, wherein said interferon gamma is a truncated interferon gamma.

Embodiment 38: The method of embodiment 35, wherein said interferon gamma is an interferon gamma having 1-15 amino acids truncated from the carboxyl terminus and/or 1-3 amino acids truncated from the amino terminus.

Embodiment 39: The method of embodiment 35, wherein said interferon gamma is a truncated interferon gamma where the amino acid sequence of said truncated interferon gamma consists of the sequence

```
                                    (SEQ ID NO: 24)
DPYVKEAE NLKKYFNAGH SDVADNGTLF LGILKNWKEE

SDRKIMQSQI VSFYFKLFKN FKDDQSIQKS VETIKEDMNV

KFFNSNKKKR DDFEKLTNYS VTDLNVQRKA IHELIQVMAE

LSPAAKTGKR KRSQM.
```

Embodiment 40: The method according to any one of embodiments 1-39, wherein said interferon is a human interferon.

Embodiment 41: The method according to any one of embodiments 1-39, wherein said interferon is a non-human interferon.

Embodiment 42: The method of embodiment 41, wherein said interferon is a murine interferon.

Embodiment 43: The method according to any one of embodiments 1-39, wherein said interferon is a mutant interferon gamma.

Embodiment 44: The method of embodiment 43, wherein said interferon is a mutant interferon-alpha.

Embodiment 45: The method of embodiment 44, wherein said interferon is a mutant interferon-alpha having lower activity than native interferon alpha.

Embodiment 46: The method of embodiment 44, wherein said interferon is a mutant interferon-alpha having higher activity than native interferon alpha.

Embodiment 47: The method of embodiment 44, wherein said interferon is a mutant human interferon α-2 having mutations at one or more sites selected from the group consisting of His57, Glu58, and Gln61.

Embodiment 48: The method of embodiment 47, wherein said interferon is an interferon α-2 having a mutation at His57.

Embodiment 49: The method of embodiment 48, wherein said mutation at His57 is a mutation to an amino acid selected from the group consisting of A, Y, and M.

Embodiment 50: The method of embodiment 49, wherein said mutation at His57 is a mutation to tyrosine (Y).

Embodiment 51: The method according to any one of embodiments 47-50, wherein said interferon is an interferon α-2 having a mutation at Glu58.

Embodiment 52: The method of embodiment 51, wherein said mutation at Glu58 is a mutation to an amino acid selected from the group consisting of A, N, D, and L.

Embodiment 53: The method of embodiment 52, wherein said mutation at Glu58 is a mutation to asparagine (N).

Embodiment 54: The method according to any one of embodiments 47-53, wherein said interferon is an interferon α-2 having a mutation at Gln61.

Embodiment 55: The method of embodiment 54, wherein said mutation at Gln61 is a mutation to an amino acid selected from the group consisting of A, S, and D.

Embodiment 56: The method of embodiment 55, wherein said mutation at Gln61 is a mutation to serine (S).

Embodiment 57: The method of embodiment 47, wherein said interferon comprises the mutations H57Y, E58N, and Q61S.

Embodiment 58: The method of embodiment 47, wherein said interferon comprises the mutations H57M, E58L, and Q61D.

Embodiment 59: The method of embodiment 47, wherein said interferon comprises the mutations H57Y, E58L, and Q61D.

Embodiment 60: The method of embodiment 47, wherein said interferon comprises the mutations H57Y, E58A, and Q61S.

Embodiment 61: The method of embodiment 47, wherein said interferon comprises the mutations H57A, E58A, and Q61A.

Embodiment 62: The method of embodiment 44, wherein said interferon is a mutant human interferon α-2 having attenuated activity.

Embodiment 63: The method of embodiment 47, wherein said interferon comprises a mutation at residue 144 and/or residue 145.

Embodiment 64: The method of embodiment 63, wherein said interferon comprises a mutation selected from the group consisting of R144A, R144T, and R144I.

Embodiment 65: The method of embodiment 64, wherein said interferon comprises an R144A mutation.

Embodiment 66: The method of embodiment 64, wherein said interferon comprises an R144T mutation.

Embodiment 67: The method of embodiment 64, wherein said interferon comprises an R144I mutation.

Embodiment 68: The method according to any one of embodiments 63-67, wherein said interferon comprise a mutation selected from the group consisting of A145G, A145H, and A145D.

Embodiment 69: The method of embodiment 68, wherein said interferon comprises an A145G mutation.

Embodiment 70: The method of embodiment 68, wherein said interferon comprises an A145H mutation.

Embodiment 71: The method of embodiment 68, wherein said interferon comprises an A145D mutation.

Embodiment 72: The method according to any of embodiments 1-71, wherein said antibody is chemically coupled to said interferon.

Embodiment 73: The method according to any of embodiments 1-71, wherein said antibody is directly joined to said interferon.

Embodiment 74: The method according to any of embodiments 1-71, wherein said antibody is joined to said interferon with a single amino acid or peptide linker.

Embodiment 75: The method of embodiment 74, wherein a said peptide linker joins said interferon to the carboxyl terminus of the CH3 domain of said antibody.

Embodiment 76: The method of embodiment 75, wherein said peptide linker joins the amino terminus of said interferon to the carboxyl terminus of the CH3 domain of said antibody.

Embodiment 77: The method of embodiment 75, wherein said peptide linker joins the carboxyl terminus of said interferon to the carboxyl terminus of the CH3 domain of said antibody.

Embodiment 78: The method according to any one of embodiments 74-77, wherein said peptide linker is proteolysis resistant.

Embodiment 79: The method according to any one of embodiments 74-78, wherein said peptide linker is fewer than 30 amino acids in length.

Embodiment 80: The method according to any one of embodiments 74-79, wherein said peptide linker is not (Gly$_4$Ser)$_3$.

Embodiment 81: The method according to any one of embodiments 74-77, wherein the amino acid sequence of said peptide linker is selected from the group consisting of

```
                                       (SEQ ID NO: 31)
GGG, GGS, GGGGS, (SEQ ID NO: 32)
SGGGGS, (SEQ ID NO: 33)
GGGGSGGGGS, (SEQ ID NO: 34)
A EAAAK A, (SEQ ID NO: 35)
A EAAAK EAAAK A, (SEQ ID NO: 36)
A EAAAK EAAAK EAAAK A, (SEQ ID NO: 37)
A EAAAK EAAAK EAAAK EAAAK A, (SEQ ID NO: 38)
A EAAAK EAAAK EAAAK EAAAK EAAAK A, (SEQ ID NO: 39)
AEAAAKEAAAKAG, (SEQ ID NO: 40)
AEAAAKEAAAKAGS, (SEQ ID NO: 41)
GGGGG, (SEQ ID NO: 42)
GGAGG, (SEQ ID NO: 43)
GGGGGGGG, (SEQ ID NO: 44)
GAGAGAGAGA, (SEQ ID NO: 45)
RPLSYRPPFPFGFPSVRP, (SEQ ID NO: 46)
YPRSIYIRRRHPSPSLTT, (SEQ ID NO: 47)
TPSHLSHILPSFGLPTFN, (SEQ ID NO: 48)
RPVSPFTFPRLSNSWLPA, (SEQ ID NO: 49)
SPAAHFPRSIPRPGPIRT, (SEQ ID NO: 50)
APGPSAPSHRSLPSRAFG, (SEQ ID NO: 51)
PRNSIHFLHPLLVAPLGA, (SEQ ID NO: 52)
MPSLSGVLQVRYLSPPDL, (SEQ ID NO: 53)
SPQYPSPLTLTLPPHPSL, (SEQ ID NO: 54)
NPSLNPPSYLHRAPSRIS, (SEQ ID NO: 55)
LPWRTSLLPSLPLRRRP, (SEQ ID NO: 56)
PPLFAKGPVGLLSRSFPP, (SEQ ID NO: 57)
VPPAPVVSLRSAHARPPY, (SEQ ID NO: 58)
LRPTPPRVRSYTCCPTP, (SEQ ID NO: 59)
PNVAHVLPLL TVPWDNLR, (SEQ ID NO: 60)
CNPLLPLCARSPAVRTFP, (SEQ ID NO: 61)
LGTPTPTPTPTGEF, (SEQ ID NO: 62)
EDFTRGKL, (SEQ ID NO: 63)
L EAAAR EAAAR EAAAR EAAAR, (SEQ ID NO: 64)
L EAAAR EAAAR EAAAR, (SEQ ID NO: 65)
L EAAAR EAAAR, (SEQ ID NO: 66)
L EAAAR, (SEQ ID NO: 67)
EAAAR EAAAR EAAAR EAAAR, (SEQ ID NO: 68)
EAAAR EAAAR EAAAR, (SEQ ID NO: 69)
EAAAR EAAAR,
```

-continued

EAAAR, (SEQ ID NO: 70)

LTEEQQEGGG, (SEQ ID NO: 71)

TEEQQEGGG, (SEQ ID NO: 72)

LAKLKQKTEQLQDRIAGGG, (SEQ ID NO: 73)

LELKTPLGDT THTCPRCPEP KSCDTPPPCP RCPEPKSCDT PPPCPRCPEP KSCDTPPPCP RCPGG, and (SEQ ID NO: 74)

LEPKSSDKTHTSPPSPGG. (SEQ ID NO: 75)

Embodiment 82: The method according to any one of embodiments 74-77, wherein the amino acid sequence of said peptide linker is selected from the group consisting of SGGGGS, GGGGS, AEAAAKEAAAKAG, and AEAAAKEAAAKAGS.

Embodiment 83: The method according to any one of embodiments 74-77, wherein the amino acid sequence of said peptide linker is SGGGGS.

Embodiment 84: The method according to any one of embodiments 74-77, wherein the amino acid sequence of said peptide linker is LTEEQQEGGG (SEQ ID NO:69).

Embodiment 85: The method according to any one of embodiments 74-77, wherein the amino acid sequence of said peptide linker is TEEQQEGGG (SEQ ID NO:70).

Embodiment 86: The method according to any one of embodiments 74-77, wherein the amino acid sequence of said peptide linker is LAKLKQKTEQLQDRIAGGG (SEQ ID NO:71).

Embodiment 87: The method according to any one of embodiments 74-77, wherein the amino acid sequence of said peptide linker is LELKTPLGDT THTCPRCPEP KSCDTPPPCP RCPEPKSCDT PPPCPRCPEP KSCDTPPPCP RCPGG (SEQ ID NO:72).

Embodiment 88: The method according to any one of embodiments 74-77, wherein the amino acid sequence of said peptide linker is LEPKSSDKTHTSPPSPGG (SEQ ID NO:73).

Embodiment 89: The method according to any one of embodiments 1-27, wherein said targeted interferon comprises an interferon alpha 14 attached to an antibody comprising the variable region of rituximab.

Embodiment 90: The method of embodiment 89, wherein said antibody is an IgG.

Embodiment 91: The method according to any one of embodiments 89-90, wherein said antibody is attached to said interferon by an SGGGGS (SEQ ID NO:27) linker.

Definitions

The terms "targeted interferon" as used herein refers to an interferon attached to a "targeting moiety" (e.g., an antibody) that binds to a molecule disposed on the surface of a cell (e.g., a cancer cell).

An adoptive cell therapy (ACT) is said to be "directed to a cancer" or "directed against a cancer) when the cells comprising the adoptive cell therapeutic are selected or designed to target a particular cancer. In the case of tumor infiltrating lymphocytes the TILs are selected that infiltrate and ultimately kill or inhibit growth and/or proliferation of the cancer. Such TILs are often derived from cells obtained from the same cancer. A chimeric antigen receptor (CAR) T cell and a T cell receptor transgenic T cell are "directed to a cancer" or "directed against a cancer" when the CAR-T cell or the TCR binds to a marker expressed by the target cancer cell(s). Illustrative markers include, but are not limited to CD19, CD10, and the like.

A "targeted interferon" refers to an interferon that is attached to a "targeting moiety" that binds to a particular target (e.g., a marker found on cancer cells). @ice the targeting moiety comprises an antibody that binds (e.g., that specifically binds) a The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Preferred "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxyl terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

An "antibody", as used herein, refers to a protein consisting of one or more polypeptides substantially encoded by immunoglobulin genes or fragments of immunoglobulin genes. In certain embodiments, the immunoglobulin genes are human immunoglobulin genes. Recognized immunoglobulin genes include the kappa, lambda, alpha, gamma, delta, epsilon and mu constant region genes, as well as myriad immunoglobulin variable region genes. Light chains are typically classified as either kappa or lambda. Heavy chains are typically classified as gamma, mu, alpha, delta, or epsilon, which in turn define the immunoglobulin classes, IgG, IgM, IgA, IgD and IgE, respectively.

A typical (native) immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these regions of the light and heavy chains respectively. It is noted that immunoglobulins IgA and IgM contain multiple copies of the four chain structure.

Antibodies exist as intact immunoglobulins (also referred to as a "full antibody" or a "full-length antibody") or as a number of well characterized fragments produced by digestion with various peptidases or expressed de novo. Thus, for example, pepsin digests an antibody below the disulfide linkages in the hinge region to produce F(ab)'2, a dimer of Fab which itself is a light chain joined to $V_H$-$C_H$1 by a disulfide bond. The F(ab)'2 may be reduced under mild conditions to break the disulfide linkage in the hinge region thereby converting the (Fab')$_2$ dimer into an Fab' monomer. The Fab' monomer is essentially an Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies, including, but are not limited to, Fab'2, IgG, IgM, IgA, IgE, scFv, dAb, nanobodies, unibodies, and diabodies. In various embodiments preferred antibodies include, but are not limited to Fab'2, IgG, IgM, IgA, IgE, and single chain antibodies, more preferably single chain Fv (scFv) antibodies in which a variable heavy and a variable light chain are joined together (directly or through a peptide linker) to form a continuous polypeptide.

In certain embodiments antibodies and fragments used in the constructs described herein can be bispecific. Bispecific antibodies or fragments can be of several configurations. For example, bispecific antibodies may resemble single antibodies (or antibody fragments) but have two different antigen binding sites (variable regions). In various embodiments bispecific antibodies can be produced by chemical techniques (Kranz et al. (1981) *Proc. Natl. Acad. Sci. USA*, 78: 5807), by "polydoma" techniques (see, e.g., U.S. Pat. No. 4,474,893), or by recombinant DNA techniques. In certain embodiments bispecific antibodies of the present invention can have binding specificities for at least two different epitopes at least one of which is a tumor associate antigen. In various embodiments the antibodies and fragments can also be heteroantibodies. Heteroantibodies are two or more antibodies, or antibody binding fragments (e.g., Fab) linked together, each antibody or fragment having a different specificity.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. *Sequences of proteins of immunological interest*, 4th ed. U.S. Dept. Health and Human Services, Public Health Services, Bethesda, MD (1987).

The term "interferon" refers to a full-length interferon or to an interferon fragment (truncated interferon) or interferon mutant, that substantially retains the biological activity of the full length wild-type interferon (e.g., 10%, or at least 20%, or at least 30%, or at least 40%, or at least 50%, or at least 60%, or at least 70%, or at least 80%, or at least 90%, more preferably at least 95%, 98%, or 99% of the full-length interferon in its free form (e.g., when not a component of a chimeric construct). In certain embodiments, the interferon includes a mutated interferon that either enhances or attenuates interferon activity. Attenuated interferons are described, inter alia, by Pogue et al. (2016) *PLoS One* 11(9): e0162472. In certain embodiments an attenuated interferon has activity less than about 10% in binding to its receptor. Interferons include type I interferons (e.g., interferon-alpha and interferon-beta) as well as type II interferons (e.g., interferon-gamma). The interferon (e.g., IFN-α) can be from essentially any mammalian species. In certain preferred embodiments, the interferon is from a species selected from the group consisting of human, equine, bovine, rodent, porcine, lagomorph, feline, canine, murine, caprine, ovine, a non-human primate, and the like. In various embodiments the mutated interferon comprises one or more amino acid substitutions, insertions, and/or deletions.

A single chain Fv ("sFv" or "scFv") polypeptide is a covalently linked $V_H$:$V_L$ heterodimer which, in certain embodiments, may be expressed from a nucleic acid including $V_H$- and $V_L$-encoding sequences either joined directly or joined by a peptide-encoding linker. Huston et al. (1998) *Proc. Nat. Acad. Sci. USA*, 85: 5879-5883. A number of approaches for converting the naturally aggregated, but chemically separated light and heavy polypeptide chains from an antibody V region into an sFv molecule that will fold into a three dimensional structure substantially similar to the structure of an antigen-binding site are known (see, e.g., U.S. Pat. Nos. 5,091,513 and 5,132,405, and 4,956,778).

Chondroitin sulfate proteoglycan 4 (CSPG4) consisting of a protein core and a chondroitin sulfate side chain is also known as high-molecular weight melanoma associated antigen (HMW-MAA) and melanoma chondroitin sulface proteoglycan (MCSP). It has been studied as a target for the treatment of melanoma. This tumor antigen is highly expressed on greater than 80% of human melanomas and has a restricted distribution in normal tissues. CSPG4 plays an important role in the biology of melanoma cells through its modulation of integrin function and enhanced growth factor receptor-regulated pathways including sustained activation of ERK 1,2. It is also expressed on cancer-initiating cells and a broad range of other tumors including breast cancer including triple negative breast cancer, glioma, squamonous cell carcinoma of head and neck, myeloid leukemic cells, pancreatic carcinoma, chondrosarcoma, chordoma, mesothelioma, renal cell carcinoma, lung carcinoma, cancer stem cells, and ovarian carcinoma. Expression of CSPG4 is associated with the progression of many different cancers.

The phrase "inhibition of growth and/or proliferation" of a cancer cell refers to decrease in the growth rate and/or proliferation rate of a cancer cell. In certain embodiments this includes death of a cancer cell (e.g. via apoptosis). In certain embodiments this term also refers to inhibiting the growth and/or proliferation of a solid tumor and/or inducing tumor size reduction or elimination of the tumor.

The terms "tumor associated antigen", "TAA", and "cancer marker" are used interchangeably to refer to biomolecules such as proteins, carbohydrates, glycoproteins, and the like that are exclusively or preferentially or differentially expressed on a cancer cell and/or are found in association with a cancer cell and thereby provide targets preferential or specific to the cancer. In various embodiments the preferential expression can be preferential expression as compared to any other cell in the organism, or preferential expression within a particular area of the organism (e.g. within a particular organ or tissue).

The terms "subject," "individual," and "patient" may be used interchangeably and refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, psychiatric care facility, as an outpatient, or other clinical context. In certain embodiments, the subject may not be under the care or prescription of a physician or other health worker.

The phrase "cause to be administered" refers to the actions taken by a medical professional (e.g., a physician), or a person controlling medical care of a subject, that control and/or permit the administration of the agent(s)/compound (s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like. Where administration is described herein, "causing to be administered" is also contemplated.

The term "exhibiting IFN gamma activity" is intended to indicate that the polypeptide has one or more of the functions of native IFNγ, in particular huIFNγ or rhIFNγ. Such functions include, inter alia, the capability to bind to an IFNγ receptor and cause transduction of the signal transduced upon huIFNγ-binding of its receptor as determined in vitro or in vivo (i.e., in vitro or in vivo bioactivity). The IFNγ receptor has been described by Aguet et al. (1988) *Cell* 55: 273-280) and Calderon et al. (1988) *Proc. Natl. Acad. Sci. USA*, 85:4837-4841. The "IFNγ polypeptide" is a polypeptide exhibiting IFNγ activity and is used herein about the polypeptide in monomer or dimeric form, as appropriate. For instance, when specific substitutions are indicated these are normally indicated relative to the IFNγ polypeptide monomer. When reference is made to the IFNγ as part of a conjugate this is normally in dimeric form (and thus, e.g., comprises two IFNγ polypeptide monomers modified as described). The dimeric form of the IFNγ polypeptides may be provided by the normal association of two monomers or be in the form of a single chain dimeric IFNγ polypeptide. The IFNγ polypeptide described herein may have an in vivo or in vitro bioactivity of the same magnitude as huJFNγ or rhuIFNγ or lower or higher, e.g. an in vivo or in vitro bioactivity of >100% (e.g., 125% or greater, or 150% or greater, or 200% or greater, or 300% or greater, or 400% or greater, or 500% or greater, or 1000% (10-fold) or greater, and so forth), 1-100% of that of huIFNγ or rhuIFNγ, as measured under the same conditions, e.g. 1-25% or 1-50% or 25-100% or 50-100% of that of huIFNγ or rhuIFNγ.

DETAILED DESCRIPTION

Figure 1:
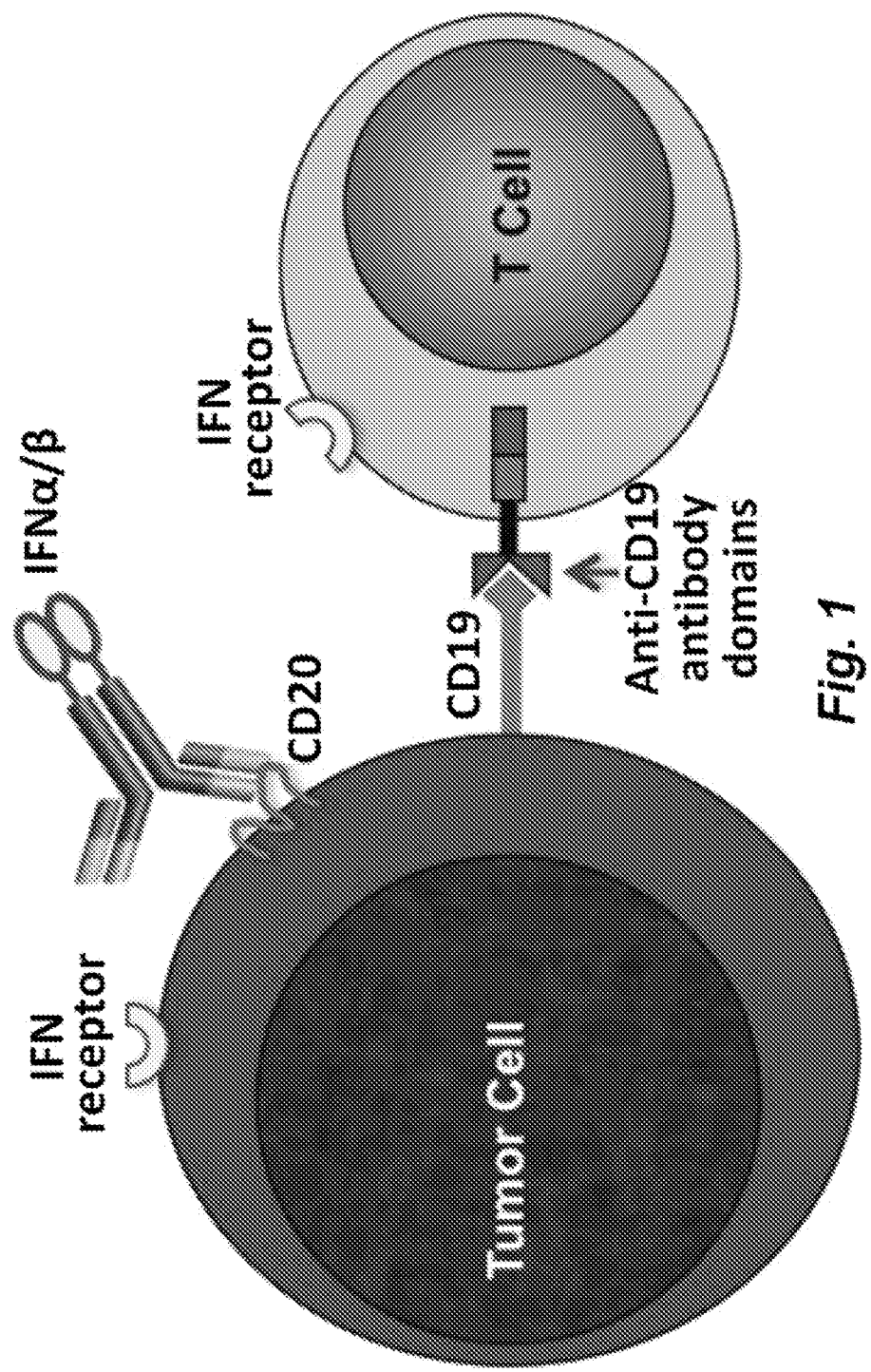
FIG. 1 illustrates the use of antibody-interferon fusion proteins to boost the efficacy of adoptive T cell and CAR T cell therapies against cancer. As an illustrative, but non-limiting example, antibody-interferon (Ab-IFNα/0) fusion protein targeting CD20 on B cell lymphomas attaches to the tumor cell surface. Then the fused IFN moiety can attach to IFN receptors on T cells themselves to stimulate their cytolytic function and survival, thereby improving tumor response.

With the multitude of immunotherapeutic properties of IFN, we hypothesized that pretreatment of lymphoma tumor cells with anti-CD20-hIFNα14 would result in enhanced cell killing and increased production of cytokines during CAR T cell therapy. The goal of this study was to examine the effect of anti-CD20-hIFNα14 treatment on CD19 specific killing by CAR T cells in cell lines of varying histology. In order to corroborate the enhanced cell killing, we examined the cytokine production of combination therapy with CAR T cells and anti-CD20-hIFNα14 or rituximab. Indeed, we found cell killing of lymphoma cell lines when treated with combination of anti-CD20-hIFNα14 and CAR T cell therapy with a marked increase in the production of proinflammatory cytokines by the CAR T cells. These data suggest that anti-CD20-hIFNα14 may be useful in improving the efficacy of CAR T cell therapy. More generally, these data suggest that a targeted interferon (e.g., an interferon attached to an antibody that binds to a cancer cell marker) directed to (e.g., that binds to) can enhance the activity of an adoptive T cell therapy targeted to the same cancer. Thus, for example, a targeted interferon that binds a cancer marker found on a B cell lymphoma (e.g., CD20) can promote T cell activities including recognition of tumor cells, cytotoxicity, activation and survival of an adoptive T cell therapeutic (e.g., a chimeric antigen receptor (CAR) T cell, a tumor infiltrating lymphocyte (TIL), a virus-specific T cell, and a T cell receptor transgenic T cell) directed against another marker found on a B cell lymphoma (e.g., CD19).

Accordingly in certain embodiments, methods of treating a cancer in a mammal (e.g., a human or a non-human mammal) are provided where the methods comprise: administering to the mammal a targeted interferon where the targeted interferon comprises an interferon attached to an antibody that binds to a cell surface marker of the cancer; and administering to the mammal an adoptive T cell therapy targeted to the same cancer. In certain embodiments the treatment inhibits the growth and/or proliferation and/or invasiveness of cancer cells. In certain embodiments the method reduces or eliminates tumor burden. In certain embodiments the method reduces or eliminates metastatic cell burden.

In certain embodiments methods of improving efficacy of an adoptive T cell therapy directed against a cancer in a mammal are provided where the method comprises administering to a mammal receiving an adoptive T cell therapy a targeted interferon where the targeted interferon comprises an interferon attached to an antibody that binds to a cell surface marker of the same cancer to which the adoptive T cell therapy is directed. In certain embodiments these methods improve recognition of tumor cells, and/or cytotoxicity, and/or activation, and/or survival of an adoptive T cell therapeutic as compared to the use of the adoptive T cell therapeutic in the absence of said targeted interferon.

In various embodiments the adoptive T cell therapy comprises use of a therapeutic selected from the group consisting of a chimeric antigen receptor (CAR) T cell, a tumor infiltrating lymphocyte (TIL), a virus-specific T cell, and a T cell receptor transgenic T cell.

There is potentially a tremendous market for adoptive T cell therapy (ACT) in its growing number of forms. There are several other strategies that have been proposed for boosting ACT in cancer, but none has the feature of antibody-IFN fusion proteins, which have the unique properties of: 1) antibody-mediated targeting of another immune-reactive molecule to the tumor site. For example, lymphomas express both markers CD19 and CD20. One can use a CD20-targeting fusion protein (as in our provided example) plus CAR T cells targeting CD19, and thus achieve a two-pronged attack against the cancer cells. 2) Antibody-IFN fusion proteins actually lead to signals that attract therapeutic T cells to home to sites of cancers, via production of chemokines and other cytokines. While direct injection of IFNs or molecules that can induce their production (Toll-like receptor agonists, STING agonists) can be performed, this existing approach is severely limited by the need for repeated direct injection into 1 or several tumor sites, but the injected material will diffuse away, and most cancer patients have innumerable tumor sites, some even microscopic, making direct tumor injection technically challenging, if not impossible. In contrast to these existing approaches, antibody-IFN fusion proteins localize to all sites of tumor in the body, thus permitting potentiation of ACT wherever tumors are found in the body.

Although IFNα2 has been most broadly studied clinically (Borden and others 2000), a recent study showed that among the 12 human IFN subtype α14 has the strongest anti-proliferative activity against cancer cells (Lavoie and others 2011)). Therefore, for the studies described in Example 1, we focused our attention on the fusion protein, anti-CD20-hIFNα14. However as explained herein the use of any of a number of other targeted interferons is contemplated.

Targeted Interferons.

It was a surprising discovery that targeted interferon (e.g., Ab-INFα14) can prime tumor cells for CAR T (or other adoptive T cell) therapy and that the fusion protein that is bound to the target cancer cell(s) (e.g., lymphoma cells) is sufficient for the enhanced killing by the adoptive T cell therapy (e.g., CAR T cells). Accordingly, as explained above, it is believed that targeted interferon can be used to enhance the efficacy of an adoptive T cell therapy.

In certain embodiments the targeting moieties (e.g., antibodies) are chemically conjugated to the interferon, while in other embodiments, the targeting moiety is expressed as a fusion protein with the interferon. When produced as a fusion protein the targeting moiety (e.g., antibody) component can be directly fused to the interferon, or attached to the interferon by a single amino acid, or attached to the interferon by a peptide linker (e.g., a SerGlyGlyGlyGlySer (SEQ ID NO:1) linker, a $(Gly_4Ser)_3$ (SEQ ID NO:2) linker, a AEAAAKEAAAKA (SEQ ID NO:3) and the like.

Targeting Moieties.

In various embodiments, the targeting moiety comprising the targeted interferon is a molecule that specifically or preferentially binds a marker expressed by (e.g., on the surface of) or associated with the target cancer cell(s). Cancers cells include but are not limited to solid tumors, such as cancers of the breast, respiratory tract, brain, reproductive organs, digestive tract, urinary tract, eye, liver, skin, head and neck, thyroid, parathyroid and their distant metastases. These disorders also include lymphomas, sarcomas, and leukemias. Examples of breast cancer include, but are not limited to invasive ductal carcinoma, invasive lobular carcinoma, ductal carcinoma in situ, and lobular carcinoma in situ. Examples of cancers of the respiratory tract include but are not limited to small-cell and non-small-cell lung carcinoma, as well as bronchial adenoma and pleuropulmonary blastoma. Examples of brain cancers include but are not limited to brain stem and hypophtalmic glioma, cerebellar and cerebral astrocytoma, medulloblastoma, ependymoma, as well as neuroectodermal and pineal tumor. Tumors of the male reproductive organs include but are not limited to prostate and testicular cancer. Tumors of the female reproductive organs include, but are not limited to endometrial, cervical, ovarian, vaginal, and vulvar cancer, as well as sarcoma of the uterus. Tumors of the digestive tract include, but are not limited to anal, colon, colorectal, esophageal, gallbladder, gastric, pancreatic, rectal, small-intestine, and salivary gland cancers. Tumors of the urinary tract include, but are not limited to bladder, penile, kidney, renal pelvis, ureter, and urethral cancers. Eye cancers include but are not limited to intraocular melanoma and retinoblastoma. Examples of liver cancers include but are not limited to hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to squamous cell carcinoma, Kaposi's sarcoma, malignant melanoma, Merkel cell skin cancer, and non-melanoma skin cancer. Head-and-neck cancers include but are not limited to laryngeal/hypopharyngeal/nasopharyngeal/oropharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system. Sarcomas include but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals and can be treated similarly by the use of a targeted interferon in combination with an adoptive T cell therapy, e.g., as described herein.

In certain embodiments, the targeting moiety is a moiety that binds a cancer marker (e.g., a tumor associated antigen). A wide variety of cancer markers are known to those of skill in the art. The markers need not be unique to cancer cells but can also be effective where the expression of the marker is elevated in a cancer cell (as compared to normal healthy cells) or where the marker is not present at comparable levels in surrounding tissues (especially where the chimeric moiety is delivered locally).

Illustrative cancer markers include, for example, the tumor marker recognized by the ND4 monoclonal antibody. This marker is found on poorly differentiated colorectal cancer, as well as gastrointestinal neuroendocrine tumors (see, e.g., Tobi et al. (1998) *Cancer Detection and Prevention*, 22(2): 147-152). Other important targets for cancer immunotherapy are membrane bound complement regulatory glycoprotein: CD46, CD55 and CD59, which have been found to be expressed on most tumor cells in vivo and in vitro. Human mucins (e.g. MUC1) are known tumor markers as are gp100, tyrosinase, and MAGE, which are found in melanoma. Wild-type Wilms' tumor gene WT1 is expressed at high levels not only in most of acute myelocytic, acute lymphocytic, and chronic myelocytic leukemia, but also in various types of solid tumors including lung cancer.

Acute lymphocytic leukemia has been characterized by the TAAs HLA-DR, CD1, CD2, CD5, CD7, CD19, and CD20. Acute myelogenous leukemia has been characterized by the TAAs HLA-Dr, CD7, CD13, CD14, CD15, CD33, CD34. Breast cancer has been characterized by the markers EGFR, HER2, MUC1, Tag-72. Various carcinomas have been characterized by the markers MUC1, TAG-72, and CEA. Chronic lymphocytic leukemia has been characterized by the markers CD3, CD19, CD20, CD21, CD25, and HLA-DR. Hairy cell leukemia has been characterized by the markers CD19, CD20, CD21, CD25. Hodgkin's disease has been characterized by the Leu-M1 marker. Various melanomas have been characterized by the HMB 45 marker. Non-Hodgkin lymphomas have been characterized by the CD20, CD19, CD22, and Ia markers. And various prostate cancers have been characterized by the PSMA and SE10 markers.

In addition, many kinds of tumor cells display unusual antigens that are either inappropriate for the cell type and/or its environment or are only normally present during the organisms' development (e.g. fetal antigens). Examples of such antigens include the glycosphingolipid GD2, a disialoganglioside that is normally only expressed at a significant level on the outer surface membranes of neuronal cells, where its exposure to the immune system is limited by the blood-brain barrier. GD2 is expressed on the surfaces of a wide range of tumor cells including neuroblastoma, medulloblastomas, astrocytomas, melanomas, small-cell lung cancer, osteosarcomas and other soft tissue sarcomas. GD2 is thus a convenient tumor-specific target for immunotherapies.

Other kinds of tumor cells display cell surface receptors that are rare or absent on the surfaces of healthy cells, and which are responsible for activating cellular signaling pathways that cause the unregulated growth and division of the tumor cell. Examples include (Erb2). HER2/neu, a constitutively active cell surface receptor that is produced at abnormally high levels on the surface of breast cancer tumor cells.

Other useful targets include, but are not limited to CD19, CD20, CD52, CD33, epidermal growth factor receptor and the like.

An illustrative, but not limiting list of suitable tumor markers is provided in Table 1. Antibodies to these and other cancer markers are known to those of skill in the art and can be obtained commercially or readily produces, e.g. using phage-display technology.

TABLE 1

Illustrative cancer markers and associated references, all of which are incorporated herein by reference for the purpose of identifying the referenced tumor markers.

| Marker | Reference |
|---|---|
| 5 alpha reductase | Délos et al. (1998) *Int J Cancer*, 75: 6 840-846 |
| α-fetoprotein | Esteban et al. (1996) *Tumour Biol.*, 17(5): 299-305 |
| AM-1 | Harada et al. (1996) *Tohoku J Exp Med.*, 180(3): 273-288 |
| APC | Dihlmannet al. (1997) *Oncol Res.*, 9(3) 119-127 |
| APRIL | Sordat et al. ('998) *J Exp Med.*, 188(6): 1185-1190 |
| BAGE | Böel et al. (1995) *Immunity*, 2: 167-175. |
| β-catenin | Hugh et al. (1999) *Int J Cancer*, 82(6): 504-11 |
| Bcl2 | Koty et al. (1999) *Lung Cancer*, 23(2): 115-127 |
| bcr-abl (b3a2) | Verfaillie et al.('996) *Blood*, 87(11): 4770-4779 |
| CA-125 | Bast et al. ('998) *Int J Biol Markers*, 13(4): 179-187 |
| CASP-8/FLICE | Mandruzzato et al. (1997) *J Exp Med.*, 186(5): 785-793. |
| Cathepsins | Thomssen et al. (1995) *Clin Cancer Res.*, 1(7): 741-746 |
| CD19 | Scheuermann et al. (1995) *Leuk Lymphoma*, 18(5-6): 385-397 |
| CD20 | Knox et al. (1996) *Clin Cancer Res.*, 2(3): 457-470 |
| CD21, CD23 | Shubinsky et al. (1997) *Leuk Lymphoma*, 25(5-6): 521-530 |
| CD22, CD38 | French et al. (1995) *Br J Cancer*, 71(5): 986-994 |
| CD33 | Nakase et al. (1996) *Am J Clin Pathol.*, 105(6): 761-768 |
| CD35 | Yamakawa et al. *Cancer*, 73(11): 2808-2817 |
| CD44 | Naot et al. (1997) *Adv Cancer Res.*, 71: 241-319 |
| CD45 | Buzzi et al. (1992) *Cancer Res.*, 52(14): 4027-4035 |
| CD46 | Yamakawa et al. (1994) *Cancer*, 73(11): 2808-2817 |
| CD5 | Stein et al. (1991) *Clin Exp Immunol.*, 85(3): 418-423 |
| CD52 | Ginaldi et al. (1998) *Leuk Res.*, 22(2): 185-191 |
| CD55 | Spendlove et al. (1999) *Cancer Res.*, 59: 2282-2286. |
| CD59 (791Tgp72) | Jarvis et al. (1997) *Int J Cancer*, 71(6): 1049-1055 |
| CDC27 | Wang et al. (1999) *Science*, 284(5418): 1351-1354 |
| CDK4 | Wölfel et al. (1995) *Science*, 269(5228): 1281-1284 |
| CEA | Kass et al. (1999) *Cancer Res.*, 59(3): 676-683 |
| c-myc | Watson et al. (1991) *Cancer Res.*, 51(15): 3996-4000 |
| Cox-2 | Tsujii et al. (1998) *Cell*, 93: 705-716 |
| DCC | Gotley et al. (1996) *Oncogene*, 13(4): 787-795 |
| DcR3 | Pitti et al. (1998) *Nature*, 396: 699-703 |
| E6/E7 | Steller et al. (1996) *Cancer Res.*, 56(21): 5087-5091 |
| EGFR | Yang et al. (1999) *Cancer Res.*, 59(6): 1236-1243. |
| EMBP | Shiina et al. (1996) *Prostate*, 29(3): 169-176. |
| Ena78 | Arenberg et al. (1998) *J. Clin. Invest.*, 102: 465-472. |
| FGF8b and FGF8a | Dorkin et al. (1999) *Oncogene*, 18(17): 2755-2761 |
| FLK-1/KDR | Annie and Fong (1999) *Cancer Res.*, 59: 99-106 |
| Folic Acid Receptor | Dixon et al. (1992) *J Biol Chem.*, 267(33): 24140-72414 |
| G250 | Divgi et al. (1998) *Clin Cancer Res.*, 4(11): 2729-2739 |
| GAGE-Family | De Backer et al. (1999) *Cancer Res.*, 59(13): 3157-3165 |
| gastrin 17 | Watson et al. (1995) *Int J Cancer*, 61(2): 233-240 |
| Gastrin-releasing hormone (bombesin) | Wang et al. (1996) *Int J Cancer*, 68(4): 528-534 |
| GD2/GD3/GM2 | Wiesner and Sweeley (1995) *Int J Cancer*, 60(3): 294-299 |
| GnRH | Bahk et al. (1998) *Urol Res.*, 26(4): 259-264 |

TABLE 1-continued

Illustrative cancer markers and associated references, all of which are incorporated herein by reference for the purpose of identifying the referenced tumor markers.

| Marker | Reference |
|---|---|
| GnTV | Hengstler et al. (1998) *Recent Results Cancer Res.*, 154: 47-85 |
| gp100/Pmel17 | Wagner et al. (1997) *Cancer Immunol Immunother.*, 44(4): 239-247 |
| gp-100-in4 | Kirkin et al. (1998) *APMIS*, 106(7): 665-679 |
| gp15 | Maeurer et al. (1996) *Melanoma Res.*, 6(1): 11-24 |
| gp75/TRP-1 | Lewis et al.(1995) *Semin Cancer Biol.*, 6(6): 321-327 |
| hCG | Hoermann et al. (1992) *Cancer Res.*, 52(6): 1520-1524 |
| Heparanase | Vlodavsky et al. (1999) *Nat Med.*, 5(7): 793-802 |
| Her2/neu Her3 | Lewis et al. (1995) *Semin Cancer Biol.*, 6(6): 321-327 |
| HMTV | Kahl et al. (1991) *Br J Cancer*, 63(4): 534-540 |
| Hsp70 | Jaattela et al. (1998) *EMBO J.*, 17(21): 6124-6134 |
| hTERT (telomerase) | Vonderheide et al. (1999) *Immunity*, 10: 673-679. 1999. |
| IGFR1 | Ellis et al. (1998) *Breast Cancer Res. Treat.*, 52: 175-184 |
| IL-13R | Murata et al. (1997) *Biochem Biophys Res Commun.*, 238(1): 90-94 |
| iNOS | Klotz et al. (1998) *Cancer*, 82(10): 1897-1903 |
| Ki 67 | Gerdes et al. (1983) *Int J Cancer*, 31: 13-20 |
| KIAA0205 | Guéguen et al. (1998) *J Immunol.*, 160(12): 6188-6194 |
| K-ras, H-ras, N-ras | Abrams et al. (1996) *Semin Oncol.*, 23(1): 118-134 |
| KSA (CO17-1A) | Zhang et al. (1998) *Clin Cancer Res.*, 4(2): 295-302 |
| LDLR-FUT | Caruso et al. (1998) *Oncol Rep.*, 5(4): 927-930 |
| MAGE Family (MAGE1, MAGE3, etc.) | Marchand et al. (1999) *Int J Cancer*, 80(2): 219-230 |
| Mammaglobin | Watson et al. (1999) *Cancer Res.*, 59: 13 3028-3031 |
| MAP17 | Kocher et al. (1996) *Am J Pathol.*, 149(2): 493-500 |
| Melan-A/ MART-1 | Lewis and Houghton (1995) *Semin Cancer Biol.*, 6(6): 321-327 |
| mesothelin | Chang et al. (1996) *Proc. Natl. Acad. Sci., USA*, 93(1): 136-140 |
| MIC A/B | Groh et al. (1998) *Science*, 279: 1737-1740 |
| MT-MMP's, such as MMP2, MMP3, MMP7, MMP9 | Sato and Seiki (1996) *J Biochem (Tokyo)*, 119(2): 209-215 |
| Mox1 | Candia et al. (1992) *Development*, 116(4): 1123-1136 |
| Mucin, such as MUC-1, MUC-2, MUC-3, and MUC-4 | Lewis and Houghton (1995) *Semin Cancer Biol.*, 6(6): 321-327 |
| MUM-1 | Kirkin et al. (1998) *APMIS*, 106(7): 665-679 |
| NY-ESO-1 | Jager et al. (1998) *J. Exp. Med.*, 187: 265-270 |
| Osteonectin | Graham et al. (1997) *Eur J Cancer*, 33(10): 1654-1660 |
| p15 | Yoshida et al. (1995) *Cancer Res.*, 55(13): 2756-2760 |
| P170/MDR1 | Trock et al. (1997) *J Natl Cancer Inst.*, 89(13): 917-931 |
| p53 | Roth et al. (1996) *Proc. Natl. Acad. Sci., USA*, 93(10): 4781-4786 |
| p97/ melanotransferrin | Furukawa et al. (1989) *J Exp Med.*, 169(2): 585-590 |
| PAI-1 | Grøndahl-Hansen et al. (1993) *Cancer Res.*, 53(11): 2513-2521 |
| PDGF | Vassbotn et al. (1993) *Mol Cell Biol.*, 13(7): 4066-4076 |
| Plasminogen (uPA) | Naitoh et al. (1995) *Jpn J Cancer Res.*, 86(1): 48-56 |
| PRAME | Kirkin et al. (1998) *APMIS*, 106(7): 665-679 |
| Probasin | Matuo et al. (1985) *Biochem Biophys Res Commun.*, 130(1): 293-300 |
| Progenipoietin | — |
| PSA | Sanda et al. (1999) *Urology*, 53(2): 260-266. |
| PSM | Kawakami et al.(1997) *Cancer Res.*, 57(12): 2321-2324 |
| RAGE-1 | Gaugler et al.(1996) *Immunogenetics*, 44(5): 323-330 |
| Rb | Dosaka-Akita et al. (1997) *Cancer*, 79(7): 1329-1337 |
| RCAS1 | Sonoda et al.(1996) *Cancer*, 77(8): 1501-1509. |
| SART-1 | Kikuchi et al. (1999( *Int J Cancer*, 81(3): 459-466 |
| SSX gene family | Gure et al. (1997) *Int J Cancer*, 72(6): 965-971 |
| STAT3 | Bromberg et al. (1999) *Cell*, 98(3): 295-303 |

TABLE 1-continued

Illustrative cancer markers and associated references, all of which are incorporated herein by reference for the purpose of identifying the referenced tumor markers.

| Marker | Reference |
|---|---|
| STn (mucin assoc.) | Sandmaier et al. (1999) *J Immunother.*, 22(1): 54-66 |
| TAG-72 | Kuroki et al. (1990)*Cancer Res.*, 50(16): 4872-4879 |
| TGF-α | Imanishi et al. (1989) *Br J Cancer*, 59(5): 761-765 |
| TGF-β | Picon et al. (1998) *Cancer Epidemiol Biomarkers Prev*, 7(6): 497-504 |
| Thymosin β 15 | Bao et al. (1996) *Nature Medicine.* 2(12), 1322-1328 |
| IFN-α | Moradi et al. (1993) *Cancer*, 72(8): 2433-2440 |
| TPA | Maulard et al. (1994) *Cancer*, 73(2): 394-398 |
| TPI | Nishida et al. (1984) *Cancer Res* 44(8): 3324-9 |
| TRP-2 | Parkhurst et al. (1998) *Cancer Res.*, 58(21) 4895-4901 |
| Tyrosinase | Kirkin et al. (1998) *APMIS*, 106(7): 665-679 |
| VEGF | Hyodo et al. (1998) *Eur J Cancer*, 34(13): 2041-2045 |
| ZAG | Sanchez et al. (1999) *Science*, 283(5409): 1914-1919 |
| p16INK4 | Quelle et al. (1995) *Oncogene* Aug. 17, 1995; 11(4): 635-645 |
| Glutathione S-transferase | Hengstler (1998) et al. *Recent Results Cancer Res.*, 154: 47-85 |

As explained above, in certain embodiments the targeted interferon and adoptive T cell therapy are selected so as to target the same cancer. In certain embodiments, the targeted interferon and the adoptive T cell therapeutic target the same cancer marker and, in some instances can target the same epitope (e.g., where the same antibody is used for the targeted interferon and engineered into the CAR T cell TCR).

In other embodiments, the targeted interferon and the adoptive T cell therapy are selected so as to bind different cancer cell markers that are present on (or associated with) the same cancer. Thus, for example, CD19 and CD20 are both associated with B cell lymphomas and the targeted interferon can target (bind) CD20 while the adoptive T cell therapeutic (e.g., a CAR T cell) binds CD19, or vice versa.

Of course the use of CD19 and CD20 is illustrative and non-limiting. Numerous cancer markers (e.g., TAAs) and the respective cancers with which they are associated are known to those of skill in the art (see, e.g., Table 2, below).

TABLE 2

Illustrative cancer markers and associated cancers.

| Marker | Pathology |
|---|---|
| CD1a, CD207 | Langerhan cell histiocytosis cells |
| CD11c, CD25, CD103, CD123 | Hairy cell leukemia cells |
| CD13, CD33, CD117 | Myeloid cells |
| CD14, CD64 | Monocytic cells (positive in AML-M4 and AML-M5) |
| CD15 | Reed-Sternberg cells, neutrophils |
| CD16, CD56 | Natural killer cells |
| CD19, CD20, CD21, CD22 | B cells |
| CD23 and CD5 | Chronic lymphocytic leukemia/small lymphocytic lymphoma |
| CD5 | Mantle cell lymphoma cells |
| CD30, CD15 | Reed-Sternberg cells(Hodgkin's lymphoma) |
| CD30 | Anaplastic large cell lymphoma cells |
| CD31 | Endothelial cells (positive in angiosarcoma) |
| CD34 | Angiosarcoma |
| CD41, CD61 | Acute myoblastic leukemia |
| CD68 | Histiocytes (positive in malignant fibrous histiocytosis) |
| CD99 | Ewings sarcoma cells |
| CD117 | Gastrointestinal stromal tumor (GIST) cells, mast cells (positive in mastocytosis), myeloid cells |
| CA 125 | ovarian neoplasms |
| AFP | yolk sac (endodermal sinus) tumor and HCC |
| b-hCG | choriocarcinoma, hyatidiform moles, gestational trophoblastic tumors |
| carcinoembryonic antigen (CEA) | colorectal cancer (also elevated in pancreatic, gastric, and breast tumors) |
| bombesin | neuroblastoma (also elevated in lung and gastric cancers) |
| PSA | prostate carcinoma |
| RET & BRAF mutation | papillary carcinoma |
| RET mutation (assoc with MEN 2A/B) | medullary carcinoma |
| RAS (thyroid) | follicular carcinoma |
| CD20, CD23, CD5 | chronic lymphocytic leukemia/small lymphocytic lymphoma |
| BCMA | Multiple myeloma, leukemia, B-Cell lymphoma |
| CD19 | Acute leukemia, B-Cell lymphoma |
| ROR1 | Leukemia, breast cancer |
| CD33 | Acute myeloid leukemia |
| EGFRVIII | Glioblastoma |
| CD30 | Leukemia, B-Cell lymphoma |
| EGFR | NSCLC, epithelial carcinoma, glioma |
| FOLR1 | Ovarian cancer |
| HER2 | Ovarian cancer, breast cancer, glioblastoma, osteosarcoma |
| HGFR | Malignant melanoma, breast cancer |
| CAIX | Renal cell carcinoma (RCC) |
| CD20 | Leukemia, B-Cell lymphoma |
| CD22 | Leukemia, B-Cell lymphoma |
| EpCAM | Liver neoplasms, stomach neoplasms |
| GPC3 | Hepatocellular carcinoma |
| IL13Rα2 | Glioma |
| MSLN | Mesothelioma, ovarian cancer |
| MUC1 | Seminal vesicle cancer |
| CD138 | Multiple myeloma |
| CD38 | B-cell Malignancies |
| CSPG4 | tumors of neuroectodermal origin including melanoma and glioma, breast cancer including triple negative breast cancer, squamonous cell carcinoma of head and neck, myeloid leukemia, pancreatic carcinoma, chondrosarcoma, chordoma, mesothelioma, renal cell carcinoma, lung carcinoma, ovarian carcinoma and cancer stem cells representing various histologies |

Any of the foregoing markers can be used as targets for the targeting moieties comprising the targeted interferons described herein. In certain embodiments the target markers include, but are not limited to CD19 or CD20, or to members of the epidermal growth factor family (e.g., HER2, HER3, EGF, HER4), CD1, CD2, CD3, CD5, CD7, CD13, CD14, CD15, CD19, CD20, CD21, CD23, CD25, CD33, CD34, CD38, 5E10, CEA, HLA-DR, HM 1.24, HMB 45, 1a, Leu-M1, MUC1, PMSA, TAG-72, phosphatidyl serine antigen, and the like.

The foregoing markers are intended to be illustrative and not limiting. Other tumor associated antigens will be known to those of skill in the art.

Where the tumor marker is a cell surface receptor, ligand to that receptor can function as targeting moieties. Similarly, mimetics of such ligands can also be used as targeting moieties.

In certain embodiments, the targeting moieties can comprise antibodies, unibodies, or affybodies that specifically or preferentially bind the tumor marker. Antibodies that specifically or preferentially bind tumor markers are well known to those of skill in the art. Thus, for example, antibodies that bind to CD19 are described, inter alia, in PCT Publication No: WO 2009/054863 A2, U.S. Patent Pub. No: 2010/0104509 A1, Chinese Patent No: CN20078050552, by Löffler et al. (2000) Blood, 95:2098-2103, and the like. Similarly, known anti-CD20 antibodies include, but are not limited to rituximab, ofatumumab, tositumomab, obinutuzumab, ibritumomab, ocrelizumab, and the like. Antibodies that bind the CD22 antigen expressed on human B cells include but are not limited to HD6, RFB4, UV22-2, Tol5, 4KB128, a humanized anti-CD22 antibody (hLL2) (see, e.g., Li et al. (1989) Cell. Immunol. 111:85-99; Mason et al. (1987) Blood 69:836-40; Behr et al. (1999) Clin. Cancer Res. 5: 3304s-3314s; Bonardi et al. (1993) Cancer Res. 53:3015-3021).

Antibodies to CD33 include for example, HuM195 (see, e.g., Kossman et al. (1999) Clin. Cancer Res. 5: 2748-2755), CMA-676 (see, e.g., Sievers et al., (1999) Blood 93: 3678-3684.

Antibodies to CD38 include for example, AT13/5 (see, e.g., Ellis et al. (1995) J. Immunol. 155: 925-937), HB7, and the like.

Antibodies to HER2 include but are not limited to trastuzumab (e.g., HERCEPTIN®; Forier et al., Oncology 13: 647-58 (1999)), TAB-250 (Rosenblum et al., (1999) Cin. Cancer Res. 5: 865-874), BACH-250 (Id.), TA1 (Maier et al. (1991) Cancer Res. 51: 5361-5369 (1991)), and the mAbs described in U.S. Pat. Nos. 5,772,997; 5,770,195 (mAb 4D5; ATCC CRL 10463); and U.S. Pat. No. 5,677,171. Other fully human anti-HER2/neu antibodies are well known to those of skill in the art. Such antibodies include, but are not limited to the C6 antibodies such as C6.5, DPL5, G98A, C6MH3-B1, B1D2, C6VLB, C6VLD, C6VLE, C6VLF, C6MH3-D7, C6MH3-D6, C6MH3-D5, C6MH3-D3, C6MH3-D2, C6MH3-D1, C6MH3-C4, C6MH3-C3, C6MH3-B9, C6MH3-B5, C6MH3-B48, C6MH3-B47, C6MH3-B46, C6MH3-B43, C6MH3-B41, C6MH3-B39, C6MH3-B34, C6MH3-B33, C6MH3-B31, C6MH3-B27, C6MH3-B25, C6MH3-B21, C6MH3-B20, C6MH3-B2, C6MH3-B16, C6MH3-B15, C6MH3-B11, C6MH3-B1, C6MH3-A3, C6MH3-A2, and C6ML3-9. These and other anti-HER2/neu antibodies are described in U.S. Pat. Nos. 6,512,097 and 5,977,322, in PCT Publication WO 97/00271, in Schier et al. (1996) J Mol Biol 255: 28-43, Schier et al. (1996) J Mol Biol 263: 551-567, and the like.

Illustrative anti-MUC-1 antibodies include, but are not limited to Mc5 (see, e.g., Peterson et al. (1997) Cancer Res. 57: 1103-1108; Ozzello et al. (1993) Breast Cancer Res. Treat. 25: 265-276), and hCTMO1 (see, e.g., Van Hof et al. (1996) Cancer Res. 56: 5179-5185).

Illustrative anti-TAG-72 antibodies include, but are not limited to CC49 (see, e.g., Pavlinkova et al. (1999) Cin. Cancer Res. 5: 2613-2619), B72.3 (see, e.g., Divgi et al. (1994) Nucl. Med. Biol. 21: 9-15), and those disclosed in U.S. Pat. No. 5,976,531.

Illustrative anti-HM1.24 antibodies include but are not limited to a mouse monoclonal anti-HM1.24 IgG$_{2a}$/κ and a humanized anti-HM1.24 IgG$_1$/κ. antibody (see, e.g., Ono et al. (1999) Mol. Immuno. 36: 387-395).

Antibodies that bind to CSPG4 are disclosed, for example, in WO 1989/011296. Such antibodies include mouse monoclonal antibodies 225.28, 225.28s; 763.74; VF1-TP41.2; VT80.1 12; 653.25; 763.74; TP61.5, and T8-203 (see e.g., WO 1989/11296; Drake et al. (2009) Cancer Immunol. Immunother., 58(3): 415-427; Goto et al. (2008) Cin. Cancer Res. 14: 3401-3407), 9.2.27 (see, e.g., Morgan et al. (1981) Hybridoma, 1: 27-36) single chain antiboides 149.53, 225.28, 763.74, TP61.5, VF1-TP34, and VF1-TP41.2 (see, e.g., Campoli et al. (2004) Crit. Rev. Immunol., 24: 267-296 and Wang et al. (2011) Cancer Res., 71(24): 7410-7422), MEL-14, MEL-5 (see, e.g., U.S. Patent Publication No: 2010/0047164), and the like More generally, antibodies directed to various members of the epidermal growth factor receptor family are well suited for use as targeting moieties in the targeted interferons described herein. Such antibodies include, but are not limited to anti-EGF-R antibodies as described in U.S. Pat. Nos. 5,844,093 and 5,558,864, and in European Patent No. 706, 799A.). Other illustrative anti-EGFR family antibodies include, but are not limited to antibodies such as C6.5, C6ML3-9, C6MH3-B1, C6-B1D2, F5, HER3.A5, HER3.F4, HER3.H1, HER3.H3, HER3.E12, HER3.B12, EGFR.E12, EGFR.C10, EGFR.B11, EGFR.E8, HER4.B4, HER4.G4, HER4.F4, HER4.A8, HER4.B6, HER4.D4, HER4.D7, HER4.D11, HER4.D12, HER4.E3, HER4.E7, HER4.F8 and HER4.C7 and the like (see, e.g., U.S. Patent publications US 2006/0099205 A1 and US 2004/0071696 A1 which are incorporated herein by reference).

The Tn-MUC1 glycoprotein is present on a large number of tumors. Tn-MUC1 glycoprotein is an abnormal glycoform of MUC1, in which the unique patterns of sugars on a protein on the cell surface is changed. CAR T cells that expressing the monoclonal antibody 5E5, which specifically recognizes the sugar modification of Tn-MUC1 that is abundant specifically on cancer cells have been produced and recognized multiple types of cancer cells, including leukemia and ovarian, breast, and pancreatic cancer cells, but not normal tissues (see, e.g., Posey et al. (2016) Immunity, 44(6): 1444-1454). It will be recognized that targeted interferons that bind to these cancer cells or more specifically to Tn-MUC1 can be used to enhance the efficacy of the CAR T cells.

The targeted interferons described herein need not be limited to the use of the antibodies described above, and other such antibodies as they are known to those of skill in the art can readily be used.

While the above discussion pertains to "traditional" antibodies, it will be recognized that affybodies and/or unibodies or other antibody constructs can be used instead of antibodies.

Unibodies.

UniBody are antibody technology that produces a stable, smaller antibody format with an anticipated longer therapeutic window than certain small antibody formats. In certain embodiments unibodies are produced from IgG4 antibodies by eliminating the hinge region of the antibody. Unlike the full size IgG4 antibody, the half molecule fragment is very stable and is termed a uniBody. Halving the IgG4 molecule left only one area on the UniBody that can bind to a target. Methods of producing unibodies are described in detail in PCT Publication WO2007/059782, which is incorporated herein by reference in its entirety (see, also, Kolfschoten et al. (2007) Science 317: 1554-1557).

Affibodies.

Affibody molecules are class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (see, e.g., Nord et al. (1997) Nat. Biotechnol. 15: 772-777; Ronmark et al. (2002) Eur. J. Biochem., 269: 2647-2655.). Details of Affibodies and methods of production are known to those of skill (see, e.g., U.S. Pat. No. 5,831,012 which is incorporated herein by reference in its entirety).

It will be recognized that the antibodies described above canbe provided as whole intact antibodies (e.g., IgG), antibody fragments, or single chain antibodies, using methods well known to those of skill in the art. In addition, while the antibody can be from essentially any mammalian species, to reduce immunogenicity, it is desirable to use an antibody that is of the species in which the construct (e.g., anti-HER2/neu-IFN-α chimera) is to be used. In other words, for use in a human, it is desirable to use a human, humanized, or chimeric human antibody.

Interferons Comprising the Targeted Interferon

In various embodiments the methods described herein utilize a targeted interferon comprising an interferon (e.g., IFN-α, IFNβ, IFN-γ, etc.) joined to a targeting moiety (e.g., anti-CD20 antibody). In various embodiments the interferon can be a full length wild-type interferon (e.g. IFN-α, IFNβ, IFN-γ, etc.) an interferon fragment (e.g., an IFN-α fragment), and/or a mutated interferon. Typically, the interferon fragment is one that possesses the endogenous binding affinity and/or activity of the native interferon, preferably at a level of at least 60%, or of at least 80%, more preferably at least 90% or 95%, most preferably at least 98%, 99%, 100%, or a level greater than the wild-type interferon (in its isolated form).

Interferons and interferon mutants are a well-known and well characterized group of cytokines (see e.g., WO 2002/095067; WO 2002/079249; WO 2002/101048; WO 2002/095067; WO 2002/083733; WO 2002/086156; WO 2002/083733; WO 2003/000896; WO 2002/101048; WO 2002/079249; WO 2003/000896; WO 2004/022593; WO 2004/022747; WO 2003/023032; WO 2004/022593 and also in Kim et al. (2003) *Cancer Lett.* 189(2):183-188; Hussain et al. (2000) *J Interferon Cytokine Res.* 20(9): 763-768; Hussain et al. (1998) *J Interferon Cytokine Res.* 18(7): 469-477; Nyman et al. (1988) *Biochem. J.* 329 (Pt 2): 295-302; Golovleva et al. (1997) *J. Interferon Cytokine Res.* 17(10): 637-645; Hussain et al. (1997) *J. Interferon Cytokine Res.* 17(9): 559-566; Golovleva et al. (1997) *Hum. Hered.* 47(4): 185-188; Kita et al. (1997) *J. Interferon Cytokine Res.* 17(3): 135-140; Golovleva et al. (1996) *Am. J. Hum. Genet.* 59(3): 570-578; Hussain et al. (1996) *J. Interferon Cytokine Res.* 16(7): 523-529; Linge et al. (1995) *Biochim Biophys Acta.* 1264(3): 363-368; Gewert et al. (1995) *JInterferon Cytokine Res.* 15(5): 403-406; Lee et al. (1995) *J. Interferon Cytokine Res.* 15(4): 341-349; Kaluz et al. (1994) *Acta Virol.* 38(2): 101-104; Emanuel et al. (1993) *J Interferon Res.* 13(3): 227-231; Kaluz et al. (1993) *Acta Virol.* 37(1): 97-100; Li et al. (1992) *Sci. China B.* 35(2): 200-206.

By way of illustration, alleles of the human interferon α family of genes/proteins are illustrated in Table 3.

TABLE 3

Common alleles of the human interferon α family of genes/proteins and was constructed based on Pestka (1983) *Arch Biochem Biophys* 221: 1-37; Diaz et al. (1994) *Genomics* 22: 540-52; and Pestka (1986) *Meth. Enzymol.*, 119: 3-14; and reviewed in Krause et al. (2000) *J. Biol. Chem.* 275: 22995-3004.

| Gene | Interferon Proteins (allelic variant names) |
|---|---|
| IFNA1 | IFN-α1, IFN-αD |
| IFNA2 | IFN-α2, IFNα2b, IFN-αA, IFN-α2a, INF-α2c |
| IFNA4 | IFN-α4a, IFNα76, IFN-α4b, IFN-α74, IFN-αM |
| IFNA5 | IFN-α5, IFNαG, IFN-α61 |

TABLE 3-continued

Common alleles of the human interferon α family of genes/proteins and was constructed based on Pestka (1983) *Arch Biochem Biophys* 221: 1-37; Diaz et al. (1994) *Genomics* 22: 540-52; and Pestka (1986) *Meth. Enzymol.*, 119: 3-14; and reviewed in Krause et al. (2000) *J. Biol. Chem.* 275: 22995-3004.

| Gene | Interferon Proteins (allelic variant names) |
|---|---|
| IFNA6 | IFN-α6, IFN-αK, IFN-α54 |
| IFNA7 | IFN-α7, IFN-αJ, IFN-αJ1 |
| IFNA8 | IFN-α8, IFN-αB2, IFN-αB |
| IFNA10 | IFN-αC, IFN-α61 |
| IFNA13 | IFN-α13 |
| IFNA14 | IFN-α14, IFN-αH, IFN-αH1 |
| IFNA16 | IFN-α16, IFN-αWA, IFN-αO |
| IFNA17 | IFN-α17, IFN-α1, IFN-α88 |
| IFNA21 | IFN-α21, IFN-αF |
| IFNA22 | IFN-α22, IFN-αGX-1 |

Any of these IFN-α are contemplated for use in the constructs described herein. In certain embodiments the interferon is a human interferon isoform alpha 14 (IFNα14). In certain embodiments the interferon is a human interferon isoform alpha 2 (IFNα2). Additionally, IFN-β, IFN-γ, biologically active truncated interferons (truncated IFN-α, IFN-β, IFN-γ), and mutant interferons (e.g., mutant IFN-α, IFN-β, IFN-γ) are contemplated. Additionally, in certain embodiments, interferons with enhanced or attenuated bioactivity (e.g., through mutations) are also contemplated (see, e.g., Pogue et al. (2016) *PLoS One* 11(9): e0162472; Kalie et al. (2007) *J Biol. Chem.*, 282(15): 11602-11611; and the like).

In certain embodiments the interferon is a full-length human IFN-α, a full-length human IFN-β, or a full length human IFN-γ.

In certain embodiments the interferon is a biologically active truncated IFN-α, a biologically active truncated IFN-β, or a biologically active truncated IFN-γ.

Means of identifying such truncated or modified interferon molecules are routine to those of skill in the art. In one illustrative approach, a library of truncated and/or mutated IFN-α is produced and screened for IFN-α activity. Methods of producing libraries of polypeptide variants are well known to those of skill in the art. Thus, for example error-prone PCR can be used to create a library of mutant and/or truncated IFN-α (see, e.g., U.S. Pat. No. 6,365,408).

The resulting library members can then be screened according to standard methods know to those of skill in the art. Thus, for example, IFN-α activity can be assayed by measuring antiviral activity against a particular test virus. Kits for assaying for IFN-α activity are commercially available (see, e.g., ILITE™ alphabeta kit by Neutekbio, Ireland).

In various embodiments use of a mutated interferon alpha 2 (IFNα2) is contemplated. Certain mutants include a mutation of the His at position 57, and/or the E at position 58, and/or the Q at position 61. In certain embodiments the mutants include the mutation H57Y, and/or E58N, and/or Q61S. In certain embodiments the mutants include a mutated IFNα2 having the mutations H57Y, E58N, and Q61S (YNS) (see, e.g., Kalie et al. (2007) *J. Biol. Chem.*, 282: 11602-11611).

In certain embodiments the mutated interferon is mutated to reduces it activity thereby improving systemic tolerance while still providing on-target activity. Such attenuated interferons are well known to those of skill in the art (see, e.g., Pogue et al. (2016) *PLoS One,* 11(9):e0162472. Illustrative, but non-limiting examples of attenuated interferons include interferon alpha having at residue 144 and/or at residue 145. In certain embodiments the attenuated interferon comprises a mutation at residue 144 to alanine (IFNα(R144A)), or to threonine (IFNα(R144T)), or to inosine (IFNα(R144I)) and/or a mutation at residue 145 to glycine (IFNα(A145G)), or to histidine (IFNα(A145H)), or to aspartic acid (IFNα(A145D))).

In other embodiments mutants include a mutation of the His at position 57, and/or the E at position 58, and/or the Q at position 61 to A (alanine). In certain embodiments the mutants include a mutated IFNα2 having the mutations H57A, E58A, and Q61A (HEQ) (see, e.g., Jaitin et al. (2006) *Mol. Cellular Biol.,* 26(5): 1888-1897). In certain embodiments the mutant interferon comprises a mutation of His at position 57 to A, Y, or M, and/or a mutation of E at position 58 to A, or N, or D, or L, and/or a mutation of Q at position 61 to A, or S, or L, or D.

In certain embodiments mutant include mutants of interferon alpha 8 (IFN-α8). Various mutant IFN-α8 molecules are known (R145V, A146N, M149Y), (R145I, A146S, M149Y), and (R145L, A146S, M149Y)] that display improved anti-proliferative activity against a wide range of different cell lines (see, e.g., Yamamoto et.al. (2009) *J. Interferon & Cytokine Res,* 29:161-170). Accordingly, in certain embodiments IFN-α8 mutatns are contemplated that have R145 to V, I, or L, and/or A146 to N, or S, and/or M149 to Y are contemplated.

A mutated IFNβ comprising a serine substituted for the naturally occurring cysteine at amino acid 17 has also been demonstrated to show efficacy (see, e.g., Hawkins et al. (1985) *Cancer Res.,* 45, 5914-5920).

In various embodiments use of truncated interferons is also contemplated. Human INFα, for example, with deletions of the first 15 amino-terminal amino acid residues and/or the last 10-13 carboxyl-terminal amino acid residues, have been shown to exhibit virtually the same activity as the parent molecules (see, e.g., Ackerman (1984) *Proc. Natl. Acad. Sci., USA,* 81: 1045-1047). Accordingly, the use of IFN-αs having 1, 2, 3, up to 13 carboxyl terminal amino acid residues deleted and/or 1, 2, 3, up to 15 amino terminal amino acid residues deleted are contemplated.

It has also been demonstrated that activity resides in huIFN-α fragment HuIFN-α (1-110) (Id). Accordingly, carboxyl truncated IFNs with truncations after residue 110 and/or with 1, 2, 3, up to 15 amino terminal amino acid residues deleted are contemplated.

Certain C-terminally truncated interferon betas (IFNβ) have been shown to have increased activity (see, e.g., U.S. Patent Publication 2009/0025106 A1). Accordingly, in certain embodiments the interferon used in the constructs described herein includes the C-terminally truncated IFNβ described as IFN-Δ1, IFN-Δ2, IFN-Δ3, IFN-Δ4, IFN-Δ5, IFN-Δ6, IFN-Δ7, IFN-Δ8, IFN-Δ9, or IFN-Δ10 as described in U.S. Patent Publication NO: 2009/0025106 A1. In certain embodiments the interferon is IFN-Δ7, IFN-Δ8, or IFN-Δ9 (SEQ ID NOs: 57, 59, and 61 in US2009/0025106 A1 (see, Table 4).

TABLE 4

Truncated IFNβ showing enhanced activity (see U.S. Patent Publication 2009/0025106 A1).

| Truncated IFN | Amino Acid Sequence | SEQ ID NO |
|---|---|---|
| IFN-Δ7 | Met Gly Lys Met Ala Ser Leu Phe Ala Thr Phe Leu Val Val Leu Val<br>Ser Leu Ser Leu Ala Ser Glu Ser Ser Ala Cys Asp Leu Pro Gln Thr<br>His Ser Leu Gly Ser Arg Arg Thr Leu Met Leu Leu Ala Gln Met Arg<br>Arg Ile Ser Leu Phe Ser Cys Leu Lys Asp Arg His Asp Phe Gly Phe<br>Pro Gln Glu Glu Phe Gly Asn Gln Phe Gln Lys Ala Glu Thr Ile Pro<br>Val Leu His Glu Met Ile Gln Gln Ile Phe Asn Leu Phe Ser Thr Lys<br>Asp Ser Ser Ala Ala Trp Asp Glu Thr Leu Leu Asp Lys Phe Tyr Thr<br>Glu Leu Tyr Gln Gln Leu Asn Asp Leu Glu Ala Cys Val Ile Gln Gly<br>Val Gly Val Thr Glu Thr Pro Leu Met Lys Glu Asp Ser Ile Leu Ala<br>Val Arg Lys Tyr Phe Gln Arg Ile Thr Leu Tyr Leu Lys Glu Lys Lys<br>Tyr Ser Pro Cys Ala Trp Glu Val Val Arg Ala Glu Ile Met Arg Ser<br>Phe Ser Leu Ser Thr Asn Leu Gln | 4 |
| IFN-Δ8 | Met Gly Lys Met Ala Ser Leu Phe Ala Thr Phe Leu Val Val Leu Val<br>Ser Leu Ser Leu Ala Ser Glu Ser Ser Ala Cys Asp Leu Pro Gln Thr<br>His Ser Leu Gly Ser Arg Arg Thr Leu Met Leu Leu Ala Gln Met Arg<br>Arg Ile Ser Leu Phe Ser Cys Leu Lys Asp Arg His Asp Phe Gly Phe<br>Pro Gln Glu Glu Phe Gly Asn Gln Phe Gln Lys Ala Glu Thr Ile Pro<br>Val Leu His Glu Met Ile Gln Gln Ile Phe Asn Leu Phe Ser Thr Lys<br>Asp Ser Ser Ala Ala Trp Asp Glu Thr Leu Leu Asp Lys Phe Tyr Thr<br>Glu Leu Tyr Gln Gln Leu Asn Asp Leu Glu Ala Cys Val Ile Gln Gly<br>Val Gly Val Thr Glu Thr Pro Leu Met Lys Glu Asp Ser Ile Leu Ala<br>Val Arg Lys Tyr Phe Gln Arg Ile Thr Leu Tyr Leu Lys Glu Lys Lys<br>Tyr Ser Pro Cys Ala Trp Glu Val Val Arg Ala Glu Ile Met Arg Ser<br>Phe Ser Leu Ser Thr Asn Leu | 5 |
| IFN-Δ9 | Met Gly Lys Met Ala Ser Leu Phe Ala Thr Phe Leu Val Val Leu Val<br>Ser Leu Ser Leu Ala Ser Glu Ser Ser Ala Cys Asp Leu Pro Gln Thr<br>His Ser Leu Gly Ser Arg Arg Thr Leu Met Leu Leu Ala Gln Met Arg<br>Arg Ile Ser Leu Phe Ser Cys Leu Lys Asp Arg His Asp Phe Gly Phe<br>Pro Gln Glu Glu Phe Gly Asn Gln Phe Gln Lys Ala Glu Thr Ile Pro<br>Val Leu His Glu Met Ile Gln Gln Ile Phe Asn Leu Phe Ser Thr Lys<br>Asp Ser Ser Ala Ala Trp Asp Glu Thr Leu Leu Asp Lys Phe Tyr Thr | 6 |

TABLE 4-continued

Truncated IFNβ showing enhanced activity (see U.S. Patent Publication 2009/0025106 A1).

| Truncated IFN | Amino Acid Sequence | SEQ ID NO |
|---|---|---|
| | Glu Leu Tyr Gln Gln Leu Asn Asp Leu Glu Ala Cys Val Ile Gln Gly Val Gly Val Thr Glu Thr Pro Leu Met Lys Glu Asp Ser Ile Leu Ala Val Arg Lys Tyr Phe Gln Arg Ile Thr Leu Tyr Leu Lys Glu Lys Lys Tyr Ser Pro Cys Ala Trp Glu Val Val Arg Ala Glu Ile Met Arg Ser Phe Ser Leu Ser Thr Asn | |

In certain embodiments mutant interferons include but are not limited to mutant interferons described in U.S. Pat. No. 7,998,469 which is incorporated herein by reference for the mutant interferons described therein. Illustrative and non-limiting interferons include, for example, IFNα-2b proteins that have increased resistance proteolysis compared to the unmodified, typically wild-type, protein. The mutant IFNα-2b proteins include those selected from among proteins containing a single amino acid replacement, or a dual amino acid replacement, or a triple amino acid replacement, or 4 amino acid replacements, or 5 amino acid replacement in IFN-α2b:

(SEQ ID NO: 7)
Cys Asp Leu Pro Gln Thr His Ser Leu Gly Ser Arg

Arg Thr Leu Met Leu Leu Ala Gln Met Arg Arg Ile

Ser Leu Phe Ser Cys Leu Lys Asp Arg His Asp Phe

Gly Phe Pro Gln Glu Glu Phe Gly Asn Gln Phe Gln

Lys Ala Glu Thr Ile Pro Val Leu His Glu Met Ile

Gln Gln Ile Phe Asn Leu Phe Ser Thr Lys Asp Ser

Ser Ala Ala Trp Asp Glu Thr Leu Leu Asp Lys Phe

Tyr Thr Glu Leu Tyr Gln Gln Leu Asn Asp Leu Glu

Ala Cys Val Ile Gln Gly Val Gly Val Thr Glu Thr

Pro Leu Met Lys Glu Asp Ser Ile Leu Ala Val Arg

Lys Tyr Phe Gln Arg Ile Thr Leu Tyr Leu Lys Glu

Lys Lys Tyr Ser Pro Cys Ala Trp Glu Val Val Arg

Ala Glu Ile Met Arg Ser Phe Ser Leu Ser Thr Asn

Leu Gln Glu Ser Leu Arg Ser Lys Glu where the replacements are selected from the group consisting of: L by V at position 3; L by I at position 3; P by S at position 4; P by A at position 4; R by H at position 12; R by Q at position 12; R by H at position 13; R by Q at position 13; M by V at position 16; M by I at position 16; R by H at position 22; R by Q at position 22; R by H at position 23; R by Q at position 23; F by I at position 27; F by V at position 27; L by V at position 30; L by I at position 30; K by Q at position 31; K by T at position 31; R by H at position 33; R by Q at position 33; E by Q at position 41; E by H at position 41; K by Q at position 49; K by T at position 49; E by Q at position 58; E by H at position 58; K by Q at position 70; K by T at position 70; E by Q at position 78; E by H at position 78; K by Q at position 83; K by T at position 83; Y by H at position 89; Y by I at position 89; E by Q at position 96; E by H at position 96; E by Q at position 107; E by H at position 107; P by S at position 109; P by A at position 109; L by V at position 110; L by I at position 110; M by V at position 111; M by I at position 111; E by Q at position 113; E by H at position 113; L by V at position 117; L by I at position 117; R by H at position 120; R by Q at position 120; K by Q at position 121; K by T at position 121; R by H at position 125; R by Q at position 125; L by V at position 128; L by I at position 128; K by Q at position 131; K by T at position 131; E by Q at position 132; E by H at position 132; K by Q at position 133; K by T at position 133; K by Q at position 134; K by T at position 134; Y by H at position 135; Y by I at position 135; P by S at position 137; P by A at position 137; M by V at position 148; M by I at position 148; R by H at position 149; R by Q at position 149; E by Q at position 159; E by H at position 159; L by V at position 161; L by I at position 161; R by H at position 162; R by Q at position 162; K by Q at position 164; K by T at position 164; E by Q at position 165; and E by H at position 165.

In certain embodiments C-terminal deletions of interferon gamma (IFN-γ) are also contemplated (see, e.g., Lundell et al. (1991) *Protein Neg.*, 4(3): 335-341).

In certain embodiments, N-glycosylation sites can be added to increase resistance to proteolysis while maintaining or improving the requisite biological activity. Exemplary N-glycosylation mutants containing duo-amino acid replacements corresponding to the N-X-S or N-X-T consensus sequences are set forth in Example 3. Accordingly, provided herein are IFNα-2b and IFNα-2a mutant proteins having an increased resistance to proteolysis compared to unmodified IFNα-2b and IFNα-2a, selected from among proteins comprising one, or two, or three or four, or five, or more sets of duo-amino acid replacements in IFN-α2b (SEQ ID NO:7), corresponding to:
 D by N at position 2 and P by S at position 4;
 D by N at position 2 and P by T at position 4;
 L by N at position 3 and Q by S at position 5;
 L by N at position 3 and Q by T at position 5;
 P by N at position 4 and T by S at position 6;
 P by N at position 4 and T by T at position 6;
 Q by N at position 5 and H by S at position 7;
 Q by N at position 5 and H by T at position 7;
 T by N at position 6 and S by S at position 8;
 T by N at position 6 and S by T at position 8;
 H by N at position 7 and L by S at position 9;
 H by N at position 7 and L by T at position 9;
 S by N at position 8 and G by S at position 10;
 S by N at position 8 and G by T at position 10;
 L by N at position 9 and S by S at position 11;
 L by N at position 9 and S by T at position 11;
 M by N at position 21 and K by S at position 23;
 M by N at position 21 and K by T at position 23;
 R by N at position 22 and I by S at position 24;

R by N at position 22 and I by T at position 24;
K or R by N at position 23 and S by S at position 25;
K or R by N at position 23 and S by T at position 25;
I by N at position 24 and L by S at position 26;
I by N at position 24 and L by T at position 26;
S by N at position 25 and F by S at position 27;
S by N at position 25 and F by T at position 27;
L by N at position 26 and S by S at position 28;
L by N at position 26 and S by T at position 28;
S by N at position 28 and L by S at position 30;
S by N at position 28 and L by T at position 30;
L by N at position 30 and D by S at position 32;
L by N at position 30 and D by T at position 32;
K by N at position 31 and R by S at position 33;
K by N at position 31 and R by T at position 33;
D by N at position 32 and H by S at position 34;
D by N at position 32 and H by T at position 34;
R by N at position 33 and D by S at position 35;
R by N at position 33 and D by T at position 35;
H by N at position 34 and F by S at position 36;
H by N at position 34 and F by T at position 36;
D by N at position 35 and G by S at position 37;
D by N at position 35 and G by T at position 37;
F by N at position 36 and F by S at position 38;
F by N at position 36 and F by T at position 38;
G by N at position 37 and P by S at position 39;
G by N at position 37 and P by T at position 39;
F by N at position 38 and Q by S at position 40;
F by N at position 38 and Q by T at position 40;
P by N at position 39 and E by S at position 41;
P by N at position 39 and E by T at position 41;
Q by N at position 40 and E by S at position 42;
Q by N at position 40 and E by T at position 42;
E by N at position 41 and F by S at position 43;
E by N at position 41 and F by T at position 43;
E by N at position 42 and G by S at position 44;
E by N at position 42 and G by T at position 44;
F by N at position 43 and N by S at position 45;
F by N at position 43 and N by T at position 45;
G by N at position 44 and Q by S at position 46;
G by N at position 44 and Q by T at position 46;
N by N at position 45 and F by S at position 47;
N by N at position 45 and F by T at position 47;
Q by N at position 46 and Q by S at position 48;
Q by N at position 46 and Q by T at position 48;
F by N at position 47 and K by S at position 49;
F by N at position 47 and K by T at position 49;
Q by N at position 48 and A by S at position 50;
Q by N at position 48 and A by T at position 50;
K by N at position 49 and E by S at position 51;
K by N at position 49 and E by T at position 51;
A by N at position 50 and T by S at position 52;
A by N at position 50 and T by T at position 52;
S by N at position 68 and K by S at position 70;
S by N at position 68 and K by T at position 70;
K by N at position 70 and S by S at position 72;
K by N at position 70 and S by T at position 72;
A by N at position 75 and D by S at position 77;
A by N at position 75 and D by T at position 77;
D by N at position 77 and T by S at position 79;
D by N at position 77 and T by T at position 79;
I by N at position 100 and G by S at position 102;
I by N at position 100 and G by T at position 102;
Q by N at position 101 and V by S at position 103;
Q by N at position 101 and V by T at position 103;
G by N at position 102 and G by S at position 104;
G by N at position 102 and G by T at position 104;
V by N at position 103 and V by S at position 105;
V by N at position 103 and V by T at position 105;
G by N at position 104 and T by S at position 106;
G by N at position 104 and T by T at position 106;
V by N at position 105 and E by S at position 107;
V by N at position 105 and E by T at position 107;
T by N at position 106 and T by S at position 108;
T by N at position 106 and T by T at position 108;
E by N at position 107 and P by S at position 109;
E by N at position 107 and P by T at position 109;
T by N at position 108 and I by S at position 110;
T by N at position 108 and I by T at position 110;
K by N at position 134 and S by S at position 136;
K by N at position 134 and S by T at position 136;
S by N at position 154 and N by S at position 156;
S by N at position 154 and N by T at position 156;
T by N at position 155 and L by S at position 157;
T by N at position 155 and L by T at position 157;
N by N at position 156 and Q by S at position 158;
N by N at position 156 and Q by T at position 158;
L by N at position 157 and E by S at position 159;
L by N at position 157 and E by T at position 159;
Q by N at position 158 and S by S at position 160;
Q by N at position 158 and S by T at position 160;
E by N at position 159 and L by S at position 161;
E by N at position 159 and L by T at position 161;
S by N at position 160 and R by S at position 162;
S by N at position 160 and R by T at position 162;
L by N at position 161 and S by S at position 163;
L by N at position 161 and S by T at position 163;
R by N at position 162 and K by S at position 164;
R by N at position 162 and K by T at position 164;
S by N at position 163 and E by S at position 165; and/or
S by N at position 163 and E by T at position 165,
where residue 1 corresponds to residue 1 of the mature IFNα-2b or IFNα-2a protein set forth in SEQ ID NO:7 or IFN-α2a (CAA23805):

```
                                      (SEQ ID NO: 8)
Cys Asp Leu Pro Gln Thr His Ser Leu Gly Ser Arg

Arg Thr Leu Met Leu Leu Ala Gln Met Arg Lys Ile

Ser Leu Phe Ser Cys Leu Lys Asp Arg His Asp Phe

Gly Phe Pro Gln Glu Glu Phe Gly Asn Gln Phe Gln

Lys Ala Glu Thr Ile Pro Val Leu His Glu Met Ile

Gln Gln Ile Phe Asn Leu Phe Ser Thr Lys Asp Ser

Ser Ala Ala Trp Asp Glu Thr Leu Leu Asp Lys Phe

Tyr Thr Glu Leu Tyr Gln Gln Leu Asn Asp Leu Glu

Ala Cys Val Ile Gln Gly Val Gly Val Thr Glu Thr

Pro Leu Met Lys Glu Asp Ser Ile Leu Ala Val Arg

Lys Tyr Phe Gln Arg Ile Thr Leu Tyr Leu Lys Glu

Lys Lys Tyr Ser Pro Cys Ala Trp Glu Val Val Arg

Ala Glu Ile Met Arg Ser Phe Ser Leu Ser Thr Asn

Leu Gln Glu Ser Leu Arg Ser Lys Glu,
``` respectively. In particular embodiments, the IFNα-2b or IFNα-2a mutant protein has increased resistance to proteolysis compared to unmodified IFNα-2b or IFNα-2a, and is selected from among proteins comprising one, or two, or three, or four, or five or more sets of duo-amino acid replacements in SEQ ID NO:7 corresponding to:

Q by N at position 5 and H by S at position 7;
P by N at position 39 and E by S at position 41;
P by N at position 39 and E by T at position 41;
Q by N at position 40 and E by S at position 42;
Q by N at position 40 and E by T at position 42;
E by N at position 41 and F by S at position 43;
E by N at position 41 and F by T at position 43;
F by N at position 43 and N by S at position 45;
G by N at position 44 and Q by T at position 46;
N by N at position 45 and F by S at position 47;
N by N at position 45 and F by T at position 47;
Q by N at position 46 and Q by S at position 48;
F by N at position 47 and K by S at position 49;
F by N at position 47 and K by T at position 49;
I by N at position 100 and G by S at position 102;
I by N at position 100 and G by T at position 102;
V by N at position 105 and E by S at position 107;
V by N at position 105 and E by T at position 107;
T by N at position 106 and T by S at position 108;
T by N at position 106 and T by T at position 108;
E by N at position 107 and P by S at position 109;
E by N at position 107 and P by T at position 109;
L by N at position 157 and E by S at position 159;
L by N at position 157 and E by T at position 159;
E by N at position 159 and L by S at position 161; and
E by N at position 159 and L by T at position 161.

In certain provided herein are IFNα-2b and IFNα-2a mutant proteins comprising one or more pseudo-wild type mutations at amino acid positions of IFNα-2b or IFNα-2a corresponding to SEQ ID NO:7 or SEQ ID NO: 8. Such pseudo-wild type mutations include 1, or 2, or 3, or 4, or 5, or more mutations at amino acid residues selected from the group consisting of 9, 10, 17, 20, 24, 25, 35, 37, 41, 52, 54, 56, 57, 58, 60, 63, 64, 65, 76, 89, and 90. The mutations can be either one or more of insertions, deletions and/or replacements of the native amino acid residue(s). In one embodiment, the pseudo-wild type replacements are mutations with alanine at each position. In another embodiment, the pseudo-wild type replacements are one or more mutations in SEQ ID NO:7 corresponding to:

L by A at position 9, L by A at position 17;
Q by A at position 20, I by A at position 24;
S by A at position 25, D by A at position 35;
G by A at position 37, E by A at position 41;
T by A at position 52, P by A at position 54;
L by A at position 56, H by A at position 57;
E by A at position 58, I by A at position 60;
I by A at position 63, F by A at position 64;
N by A at position 65, W by A at position 76, and/or
Y by A at position 89, and Q by A at position 90.

In certain embodiments, the constructs described herein utilize an interferon showing a reduced activity (e.g., a decreased antiviral activity). In certain embodiments such interferons can comprise mutations at amino acid positions of IFNα-2b corresponding, amino acid residues: 2, 7, 8, 11, 13, 15, 16, 23, 26, 28, 29, 30, 31, 32, 33, 53, 69, 91, 93, 98, and/or 101 or to SEQ ID NO:7. Accordingly, in particular embodiments where it is desired to decrease the anti-viral activity of IFN-2b or IFN-2a, either one, or two, or three, or 4, or 5 or more of insertions, deletions and/or replacements of the native amino acid residue(s) can be carried out at one or more of amino acid positions of IFN-2b or IFN-2a corresponding to SEQ ID NO: 7, amino acid residues: 2, 7, 8, 11, 13, 15, 16, 23, 26, 28, 29, 30, 31, 32, 33, 53, 69, 91, 93, 98, and/or 101.

In certain embodiments, the modified IFNα cytokines are selected from among:

(a) a modified IFNα-2a that is human and is selected from among proteins comprising one, two, three, four, or 5 or more single amino acid replacements in SEQ ID NO:8, corresponding to amino acid positions: 41, 58, 78, 107, 117, 125, 133, and/or 159;

(b) a modified IFNα-c that is human and is selected from among proteins comprising one, two, three, four, or five or more single amino acid replacements in Genbank P01566, sequence:

(SEQ ID NO: 9)
Cys Asp Leu Pro Gln Thr His Ser Leu Gly Asn Arg

Arg Ala Leu Ile Leu Leu Gly Gln Met Gly Arg Ile

Ser Pro Phe Ser Cys Leu Lys Asp Arg His Asp Phe

Arg Ile Pro Gln Glu Glu Phe Asp Gly Asn Gln Phe

Gln Lys Ala Gln Ala Ile Ser Val Leu His Glu Met

Ile Gln Gln Thr Phe Asn Leu Phe Ser Thr Glu Asp

Ser Ser Ala Ala Trp Glu Gln Ser Leu Leu Glu Lys

Phe Ser Thr Glu Leu Tyr Gln Gln Leu Asn Asp Leu

Glu Ala Cys Val Ile Gln Glu Val Gly Val Glu Glu

Thr Pro Leu Met Asn Glu Asp Ser Ile Leu Ala Val

Arg Lys Tyr Phe Gln Arg Ile Thr Leu Tyr Leu Ile

Glu Arg Lys Tyr Ser Pro Cys Ala Trp Glu Val Val

Arg Ala Glu Ile Met Arg Ser Leu Ser Phe Ser Thr

Asn Leu Gln Lys Arg Leu Arg Arg Lys Asp corresponding to amino acid positions: 41, 59, 79, 108, 118, 126, 134, and/or 160;

(c) a modified IFNα-2c cytokine that is human and is selected from among cytokines comprising one, two, three, four, or five or more amino acid replacements in the sequence:

(SEQ ID NO: 10)
Cys Asp Leu Pro Gln Thr His Ser Leu Gly Ser Arg

Arg Thr Leu Met Leu Leu Ala Gln Met Arg Arg Ile

Ser Leu Phe Ser Cys Leu Lys Asp Arg Arg Asp Phe

Gly Phe Pro Gln Glu Glu Phe Gly Asn Gln Phe Gln

Lys Ala Glu Thr Ile Pro Val Leu His Glu Met Ile

Gln Gln Ile Phe Asn Leu Phe Ser Thr Lys Asp Ser

Ser Ala Ala Trp Asp Glu Thr Leu Leu Asp Lys Phe

Tyr Thr Glu Leu Tyr Gln Gln Leu Asn Asp Leu Glu

Ala Cys Val Ile Gln Gly Val Gly Val Thr Glu Thr

Pro Leu Met Lys Glu Asp Ser Ile Leu Ala Val Arg

Lys Tyr Phe Gln Arg Ile Thr Leu Tyr Leu Lys Glu

Lys Lys Tyr Ser Pro Cys Ala Trp Glu Val Val Arg

Ala Glu Ile Met Arg Ser Phe Ser Leu Ser Thr Asn

Leu Gln Glu Ser Leu Arg Ser Lys Glu corresponding to amino acid positions: 41, 58, 78, 107, 117, 125, 133, and/or 159;

(d) an IFNα-d modified protein that is human and is selected from among proteins comprising one, or two, or three, or four, or five or more single amino acid replacements in Genbank AAB59403 sequence:

(SEQ ID NO: 11)
Cys Asp Leu Pro Glu Thr His Ser Leu Asp Asn Arg

Arg Thr Leu Met Leu Leu Ala Gln Met Ser Arg Ile

Ser Pro Ser Ser Cys Leu Met Asp Arg His Asp Phe

Gly Phe Pro Gln Glu Glu Phe Asp Gly Asn Gln Phe

Gln Lys Ala Pro Ala Ile Ser Val Leu His Glu Leu

Ile Gln Gln Ile Phe Asn Leu Phe Thr Thr Lys Asp

Ser Ser Ala Ala Trp Asp Glu Asp Leu Leu Asp Lys

Phe Cys Thr Glu Leu Tyr Gln Gln Leu Asn Asp Leu

Glu Ala Cys Val Met Gln Glu Glu Arg Val Gly Glu

Thr Pro Leu Met Asn Ala Asp Ser Ile Leu Ala Val

Lys Lys Tyr Phe Arg Arg Ile Thr Leu Tyr Leu Thr

Glu Lys Lys Tyr Ser Pro Cys Ala Trp Glu Val Val

Arg Ala Glu Ile Met Arg Ser Leu Ser Leu Ser Thr

Asn Leu Gln Glu Arg Leu Arg Arg Lys Glu corresponding to amino acid positions: 41, 59, 79, 108, 118, 126, 134, and/or 160;

(e) an IFNα-5 modified protein that is human and is selected from among proteins comprising one, or two, or three, or four, or five or more single amino acid replacements in Genbank CAA26702 sequence:

(SEQ ID NO: 12)
Cys Asp Leu Pro Gln Thr His Ser Leu Ser Asn Arg

Arg Thr Leu Met Ile Met Ala Gln Met Gly Arg Ile

Ser Pro Phe Ser Cys Leu Lys Asp Arg His Asp Phe

Gly Phe Pro Gln Glu Glu Phe Asp Gly Asn Gln Phe

Gln Lys Ala Gln Ala Ile Ser Val Leu His Glu Met

Ile Gln Gln Thr Phe Asn Leu Phe Ser Thr Lys Asp

Ser Ser Ala Thr Trp Asp Glu Thr Leu Leu Asp Lys

Phe Tyr Thr Glu Leu Tyr Gln Gln Leu Asn Asp Leu

Glu Ala Cys Met Met Gln Glu Val Gly Val Glu Asp

Thr Pro Leu Met Asn Val Asp Ser Ile Leu Thr Val

Arg Lys Tyr Phe Gln Arg Ile Thr Leu Tyr Leu Thr

Glu Lys Lys Tyr Ser Pro Cys Ala Trp Glu Val Val

-continued

Arg Ala Glu Ile Met Arg Ser Phe Ser Leu Ser Ala

Asn Leu Gln Glu Arg Leu Arg Arg Lys Glu corresponding to amino acid positions: 41, 59, 79, 108, 118, 126, 134, and/or 160;

(f) an IFNα-6 modified protein that is human and is selected from among proteins comprising one, or two, or three, or four, or five or more single amino acid replacements in Genbank CAA26704 sequence:

(SEQ ID NO: 13)

Cys Asp Leu Pro Gln Thr His Ser Leu Gly His Arg

Arg Thr Met Met Leu Leu Ala Gln Met Arg Arg Ile

Ser Leu Phe Ser Cys Leu Lys Asp Arg His Asp Phe

Arg Phe Pro Gln Glu Glu Phe Asp Gly Asn Gln Phe

Gln Lys Ala Glu Ala Ile Ser Val Leu His Glu Val

Ile Gln Gln Thr Phe Asn Leu Phe Ser Thr Lys Asp

Ser Ser Val Ala Trp Asp Glu Arg Leu Leu Asp Lys

Leu Tyr Thr Glu Leu Tyr Gln Gln Leu Asn Asp Leu

Glu Ala Cys Val Met Gln Glu Val Trp Val Gly Gly

Thr Pro Leu Met Asn Glu Asp Ser Ile Leu Ala Val

Arg Lys Tyr Phe Gln Arg Ile Thr Leu Tyr Leu Thr

Glu Lys Lys Tyr Ser Pro Cys Ala Trp Glu Val Val

Arg Ala Glu Ile Met Arg Ser Phe Ser Ser Ser Arg

Asn Leu Gln Glu Arg Leu Arg Arg Lys Glu corresponding to amino acid positions: 41, 59, 79, 108, 118, 126, 134, and/or 160;

(g) an IFNα-4 modified protein that is human and is selected from among proteins comprising one, or two, or three, or four, or five or more single amino acid replacements in Genbank NP_066546 sequence:

(SEQ ID NO: 14)

Cys Asp Leu Pro Gln Thr His Ser Leu Gly Asn Arg

Arg Ala Leu Ile Leu Leu Ala Gln Met Gly Arg Ile

Ser His Phe Ser Cys Leu Lys Asp Arg His Asp Phe

Gly Phe Pro Glu Glu Glu Phe Asp Gly His Gln Phe

Gln Lys Ala Gln Ala Ile Ser Val Leu His Glu Met

Ile Gln Gln Thr Phe Asn Leu Phe Ser Thr Glu Asp

Ser Ser Ala Ala Trp Glu Gln Ser Leu Leu Glu Lys

Phe Ser Thr Glu Leu Tyr Gln Gln Leu Asn Asp Leu

Glu Ala Cys Val Ile Gln Glu Val Gly Val Glu Glu

Thr Pro Leu Met Asn Glu Asp Ser Ile Leu Ala Val

Arg Lys Tyr Phe Gln Arg Ile Thr Leu Tyr Leu Thr

Glu Lys Lys Tyr Ser Pro Cys Ala Trp Glu Val Val

Arg Ala Glu Ile Met Arg Ser Leu Ser Phe Ser Thr

Asn Leu Gln Lys Arg Leu Arg Arg Lys Asp corresponding to amino acid positions: 41, 59, 79, 108, 118, 126, 134, and/or 160;

(h) an IFNα-4b modified protein that is human and is selected from among proteins comprising one, or two, or three, or four, or five or more single amino acid replacements in Genbank CAA26701 sequence:

(SEQ ID NO: 15)
Cys Asp Leu Pro Gln Thr His Ser Leu Gly Asn Arg

Arg Ala Leu Ile Leu Leu Ala Gln Met Gly Arg Ile

Ser His Phe Ser Cys Leu Lys Asp Arg His Asp Phe

Gly Phe Pro Glu Glu Glu Phe Asp Gly His Gln Phe

Gln Lys Thr Gln Ala Ile Ser Val Leu His Glu Met

Ile Gln Gln Thr Phe Asn Leu Phe Ser Thr Glu Asp

Ser Ser Ala Ala Trp Glu Gln Ser Leu Leu Glu Lys

Phe Ser Thr Glu Leu Tyr Gln Gln Leu Asn Asp Leu

Glu Ala Cys Val Ile Gln Glu Val Gly Val Glu Glu

Thr Pro Leu Met Asn Val Asp Ser Ile Leu Ala Val

Arg Lys Tyr Phe Gln Arg Ile Thr Leu Tyr Leu Thr

Glu Lys Lys Tyr Ser Pro Cys Ala Trp Glu Val Val

Arg Ala Glu Ile Met Arg Ser Leu Ser Phe Ser Thr

Asn Leu Gln Lys Arg Leu Arg Arg Lys Asp corresponding to amino acid positions: 41, 59, 79, 108, 118, 126, 134, and/or 160;

(i) the IFNα-I modified protein that is human and is selected from among proteins comprising one, or two, or three, or four, or five or more single amino acid replacements in Genbank AAA52725 sequence:

(SEQ ID NO: 16)
Cys Asp Leu Pro Gln Thr His Ser Leu Gly Asn Arg

Arg Ala Leu Ile Leu Leu Ala Gln Met Gly Arg Ile

Ser Pro Phe Ser Cys Leu Lys Asp Arg His Asp Phe

Gly Leu Pro Gln Glu Glu Phe Asp Gly Asn Gln Phe

Gln Lys Thr Gln Ala Ile Ser Val Leu His Glu Met

Ile Gln Gln Thr Phe Asn Leu Phe Ser Thr Glu Asp

Ser Ser Ala Ala Trp Glu Gln Ser Leu Leu Glu Lys

Phe Ser Thr Glu Leu Tyr Gln Gln Leu Asn Asn Leu

Glu Ala Cys Val Ile Gln Glu Val Gly Met Glu Glu

Thr Pro Leu Met Asn Glu Asp Ser Ile Leu Ala Val

Arg Lys Tyr Phe Gln Arg Ile Thr Leu Tyr Leu Thr

Glu Lys Lys Tyr Ser Pro Cys Ala Trp Glu Val Val

Arg Ala Glu Ile Met Arg Ser Leu Ser Phe Ser Thr

Asn Leu Gln Lys Ile Leu Arg Arg Lys Asp corresponding to amino acid positions: 41, 59, 79, 108, 118, 126, 134, and/or 160;

(j) an IFNα-J modified protein that is human and is selected from among proteins comprising one, or two, or three, or four, or five or more single amino acid replacements in Genbank CAA23792 sequence:

(SEQ ID NO: 17)
Cys Asp Leu Pro Gln Thr His Ser Leu Arg Asn Arg

Arg Ala Leu Ile Leu Leu Ala Gln Met Gly Arg Ile

Ser Pro Phe Ser Cys Leu Lys Asp Arg His Glu Phe

Arg Phe Pro Glu Glu Glu Phe Asp Gly His Gln Phe

Gln Lys Thr Gln Ala Ile Ser Val Leu His Glu Met

Ile Gln Gln Thr Phe Asn Leu Phe Ser Thr Glu Asp

Ser Ser Ala Ala Trp Glu Gln Ser Leu Leu Glu Lys

Phe Ser Thr Glu Leu Tyr Gln Gln Leu Asn Asp Leu

Glu Ala Cys Val Ile Gln Glu Val Gly Val Glu Glu

Thr Pro Leu Met Asn Glu Asp Phe Ile Leu Ala Val

Arg Lys Tyr Phe Gln Arg Ile Thr Leu Tyr Leu Met

Glu Lys Lys Tyr Ser Pro Cys Ala Trp Glu Val Val

Arg Ala Glu Ile Met Arg Ser Phe Ser Phe Ser Thr

Asn Leu Lys Lys Gly Leu Arg Arg Lys Asp corresponding to amino acid positions: 41, 59, 79, 108, 118, 126, 134, and/or 160;

(k) an IFNα-H modified protein that is human and is selected from among proteins comprising one, or two, or three, or four, or five or more single amino acid (SEQ ID NO: 18)
Cys Asn Leu Ser Gln Thr His Ser Leu Asn Asn Arg Arg Thr Leu Met Leu Met Ala Gln Met Arg Arg Ile Ser Pro Phe Ser Cys Leu Lys Asp Arg His Asp Phe Glu Phe Pro Gln Glu Glu Phe Asp Gly Asn Gln Phe Gln Lys Ala Gln Ala Ile Ser Val Leu His Glu Met Met Gln Gln Thr Phe Asn Leu Phe Ser Thr Lys Asn Ser Ser Ala Ala Trp Asp Glu Thr Leu Leu Glu Lys Phe Tyr Ile Glu Leu Phe Gln Gln Met Asn Asp Leu Glu Ala Cys Val Ile Gln Glu Val Gly Val Glu Glu Thr Pro Leu Met Asn Glu Asp Ser Ile Leu Ala Val Lys Lys Tyr Phe Gln Arg Ile Thr Leu Tyr Leu Met Glu Lys Lys Tyr Ser Pro Cys Ala Trp Glu Val Val Arg Ala Glu Ile Met Arg Ser Leu Ser Phe Ser Thr Asn Leu Gln Lys Arg Leu Arg Arg Lys Asp corresponding to amino acid positions: 41, 59, 79, 108, 118, 126, 134, and/or 160;

(l) an IFNα-F modified protein that is human and is selected from among proteins comprising one, or two, or three, or four, or five or more single amino acid replacements in Genbank AAA52718 sequence:

(SEQ ID NO: 19)
```
Cys Asp Leu Pro Gln Thr His Ser Leu Gly Asn Arg
Arg Ala Leu Ile Leu Leu Ala Gln Met Gly Arg Ile
Ser Pro Phe Ser Cys Leu Lys Asp Arg His Asp Phe
Gly Phe Pro Gln Glu Glu Phe Asp Gly Asn Gln Phe
Gln Lys Ala Gln Ala Ile Ser Val Leu His Glu Met
Ile Gln Gln Thr Phe Asn Leu Phe Ser Thr Lys Asp
Ser Ser Ala Thr Trp Glu Gln Ser Leu Leu Glu Lys
Phe Ser Thr Glu Leu Asn Gln Gln Leu Asn Asp Leu
Glu Ala Cys Val Ile Gln Glu Val Gly Val Glu Glu
Thr Pro Leu Met Asn Val Asp Ser Ile Leu Ala Val
Lys Lys Tyr Phe Gln Arg Ile Thr Leu Tyr Leu Thr
Glu Lys Lys Tyr Ser Pro Cys Ala Trp Glu Val Val
Arg Ala Glu Ile Met Arg Ser Phe Ser Leu Ser Lys
Ile Phe Gln Glu Arg Leu Arg Arg Lys Glu
```
corresponding to amino acid positions: 41, 59, 79, 108, 118, 126, 134, and/or 160;

(m) an IFNα-8 modified protein that is human and is selected from among proteins comprising one, or two, or three, or four, or five or more single amino acid replacements in Genbank CAA26903, sequence:

(SEQ ID NO: 20)
```
Cys Asp Leu Pro Gln Thr His Ser Leu Gly Asn Arg
Arg Ala Leu Ile Leu Leu Ala Gln Met Arg Arg Ile
Ser Pro Phe Ser Cys Leu Lys Asp Arg His Asp Phe
Glu Phe Pro Gln Glu Glu Phe Asp Asp Lys Gln Phe
Gln Lys Ala Gln Ala Ile Ser Val Leu His Glu Met
Ile Gln Gln Thr Phe Asn Leu Phe Ser Thr Lys Asp
Ser Ser Ala Ala Leu Asp Glu Thr Leu Leu Asp Glu
Phe Tyr Ile Glu Leu Asp Gln Gln Leu Asn Asp Leu
Glu Ser Cys Val Met Gln Glu Val Gly Val Ile Glu
Ser Pro Leu Met Tyr Glu Asp Ser Ile Leu Ala Val
Arg Lys Tyr Phe Gln Arg Ile Thr Leu Tyr Leu Thr
Glu Lys Lys Tyr Ser Ser Cys Ala Trp Glu Val Val
Arg Ala Glu Ile Met Arg Ser Phe Ser Leu Ser Ile
Asn Leu Gln Lys Arg Leu Lys Ser Lys Glu
```
corresponding to amino acid positions: 41, 59, 79, 108, 118, 126, 134, and/or 160; and/or (n) an IFNα-consensus modified protein sequence that is human and is selected from among proteins that contain one, or two, or three, or four, or five or more single amino acid replacements in the consensus sequence:

(SEQ ID NO: 21)
```
Cys Asp Leu Pro Gln Thr His Ser Leu Gly Asn Arg
Arg Ala Leu Ile Leu Leu Ala Gln Met Arg Arg Ile
Ser Pro Phe Ser Cys Leu Lys Asp Arg His Asp Phe
Gly Pro Gln Glu Glu Phe Asp Gly Asn Gln Phe Gln
Lys Ala Gln Ala Ile Ser Val Leu His Glu Met Ile
Gln Gln Thr Phe Asn Leu Phe Ser Thr Lys Asp Ser
Ser Ala Ala Trp Asp Glu Ser Leu Leu Glu Lys Phe
Tyr Thr Glu Leu Tyr Gln Gln Leu Asn Asp Leu Glu
Ala Cys Val Ile Gln Glu Val Gly Val Glu Glu Thr
Pro Leu Met Asn Val Asp Ser Ile Leu Ala Val Lys
Lys Tyr Phe Gln Arg Ile Thr Leu Tyr Leu Thr Glu
Lys Lys Tyr Ser Pro Cys Ala Trp Glu Val Val Arg
Ala Glu Ile Met Arg Ser Phe Ser Leu Ser Thr Asn
Leu Gln Glu Arg Leu Arg Arg Lys Glu
```
corresponding to amino acid positions: 41, 58, 78, 107, 117, 125, 133, and/or 159.

Also contemplated are modified IFNβ cytokines, comprising mutations at one, or two, or three, or four, or five or more amino acid residues of IFNβ(GENBANK AAC41702) sequence:

(SEQ ID NO: 22)
```
Met porated herein by reference for the substitutions set for in FIGS. 12a through 12T therein.

In various embodiments proteinase resistant modified interferon-beta polypeptides as described in U.S. Pat. No. 8,052,964 B2 are also contemplated. Certain illustrative modified IFN-β molecules differ from an unmodified IFN beta by two amino acid substitutions where the unmodified IFN beta cytokine comprises the amino acid sequence of IFN-β (Genbank AAC41702, SEQ ID NO:22) and the two amino acid substitutions are selected from the group consisting of substitution of the 5th and 6th positions in SEQ ID NO:22, with aspartic acid and glutamine, respectively; or substitution of the 5th and 6th positions in SEQ ID NO:22, with glutamine; or substitution of the 5th and 6th positions in SEQ ID NO:22, with asparagine and glutamine, respectively; or substitution of the 6th and 36th positions in SEQ ID NO:22, with glutamine and isoleucine, respectively; or substitution of the 6th and 86th positions in SEQ ID NO:22, with glutamine where the two amino acid substitutions confer increased resistance to proteolysis over the unmodified IFN beta.

In certain embodiments the use of an interferon gamma (designated IFNγ or IFN-γ), a truncated IFN-γ, or a mutant IFN-γ is contemplated.

Interferon-gamma (IFNγ) is a cytokine produced by T-lymphocytes and natural killer cells and exists as a homodimer of two noncovalently bound polypeptide subunits. The mature form of each dimer comprises 143 amino acid residues (shown in SEQ ID NO:23):

DPYVKEAENL KKYFNAGHSD VADNGTLFLG ILKNWKEESD RKIMQSQIVS
FYFKLFKNFK DDQSIQKSVE TIKEDMNVKF FNSNKKKRDDF EKLTNYSVT
DLNVQRKAIH ELIQVMAELS PAAKTGKRKR SQMLFQGRRAS Q (SEQ ID NO:23)

Each subunit has two potential N-glycosylation sites (Aggarwal et al. (1992) *Human Cytokines*, Blackwell Scientific Publications) at positions 25 and 97. Depending on the degree of glycosylation the molecular weight of IFNG in dimer form is 34-50 kDa (Farrar et al. (1993) *Ann. Rev. Immunol,* 11: 571-611).

The primary sequence of wildtype human IFNG (huIFNγG) was reported by Gray et al. (1982) *Nature* 298: 859-863), Taya et al. (1982) *EMBO J.* 1: 953-958; Devos et al. (1982) *Nucleic Acids Res.* 10: 2487-2501; and Rinderknecht et al. (1984) *J. Biol. Chem.* 259: 6790-6797), and in EP 77670, EP 89676 and EP 110044. The 3D structure of huIFNG was reported by Ealick et al. (1991) *Science* 252: 698-702, 1991).

Various naturally-occurring or mutated forms of the IFNG subunit polypeptides have been reported, including one comprising a Cys-Tyr-Cys N-terminal amino acid sequence (positions (−3)-(−1) relative to SEQ ID NO:23), one comprising an N-terminal methionine (position −1 relative to SEQ ID NO:23), and various C-terminally truncated forms comprising 127-134 amino acid residues. It is known that 1-15 amino acid residues may be deleted from the C-terminus without abolishing IFNγ activity of the molecule. Furthermore, heterogeneity of the huIFNγ C-terminus was described by Pan et al. (1987) *Eur. J. Biochem.* 166: 145-149.

HuIFNγ muteins are reported by Slodowski et al. (1991) *Eur. J Biochem.* 202:1133-1140, 1991, Luk et al. (1990) *J Biol. Chem.* 265: 13314-13319, Seelig et al., (1988) *Biochemistry* 27: 1981-1987, Trousdale et al. (1985) *Invest. Ophthalmol. Vis. Sci.* 26: 1244-1251, and in EP 146354.

WO 1992/008737 discloses IFNγ variants comprising an added methionine in the N-terminal end of the full (residues 1-143) or partial (residues 1-132) amino acid sequence of wildtype human IFNG. EP 219 781 discloses partial huIFNγ sequences comprising amino 10 acid residues 3-124 (of SEQ ID NO:23)). U.S. Pat. No. 4,832,959 discloses partial huIFNG sequences comprising residues 1-127, 5-146 and 5-127 of an amino acid sequence that compared to SEQ ID NO 2 has three additional N-terminal amino acid residues (CYC). U.S. Pat. No. 5,004,689 discloses a DNA sequence encoding huIFNG without the 3 N-terminal amino acid residues CYC and its expression in *E. coli*. EP 446582 discloses *E. coli* produced rhuIFNG free of an 15 N-terminal methionine. U.S. Pat. No. 6,120,762 discloses a peptide fragment of huIFNγ comprising residues 95-134 thereof (relative to SEQ ID NO:23).

In various embodiments where interferon gamma is utilized in the constructs described herein the interferon gamma component(s) of the construct can be any polypeptide with IFNγ activity, and thus be derived from any origin, e.g. a non-human mammalian origin. However, in various embodiments, it is preferred that the parent polypeptide is huIFNγ, e.g., with the amino acid sequence shown in SEQ ID NO:23, or a variant or fragment thereof.

Examples of variants of hIFNγ that can be incorporated in the constructs contemplated herein described above, and include, but are not limited to, e.g. huIFNγ with the N-terminal addition CYC, the cysteine modified variants described in U.S. Pat. No. 6,046,034, and the like. Specific examples of fragments are those described above, and include, but are not limited to huIFNγ C-terminally truncated with 1-15 amino acid residues, e.g. with 1, 2, 3, 4, 5, 6, 7, 8, 9, 10, 11, 12, 13, 14, or 15 amino acid residues, and/or N-terminally truncated with 1-3 amino acid residues. In one illustrative, but non-limiting embodiment, the interferon comprises a truncated interferon consisting of the amino acid sequence:

(SEQ ID NO: 24)
DPYVKEAENL KKYFNAGHSD VADNGTLFLG ILKNWEEESD

RKIMQSQIVS FYFKLFKNFK DDQSIQKSVE TIKEDMNVKF

FNSNKKKRDD FEKLTNYSVT DLNVQRKAIH ELIQVMAELS

PAAKTGKRKR SQM

In certain embodiments the use of chemically modified interferon is also contemplated. For example, in certain embodiments, the interferon is chemically modified to increase serum half-life. Thus, for example, (2-sulfo-9-fluorenylmethoxycarbonyl)$_7$-interferon-α2 undergoes time-dependent spontaneous hydrolysis, generating active interferon (see, e.g., Shechter et al. (2001) *Proc. Natl. Acad. Sci., USA,* 98(3): 1212-1217). Other modifications, include for example, N-terminal modifications in including, but not limited to the addition of PEG, protecting groups, and the like. U.S. Pat. No. 5,824,784, for example, described N-terminally chemically modified interferon.

The foregoing interferons and antibodies are intended to be illustrative and not limiting. Using the teaching provided herein, other suitable modified interferons (e.g., modified IFN-α, IFNβ, IFN-γ, etc.) and constructs can readily be identified and produced.

Attachment of the Targeting Moiety (e.g, Anti-CD20 Antibody) to the Interferon (e.g., IFNα14).

In various embodiments, the targeting moiety (e.g., an anti-CD20 antibody) and the interferon can be joined together in any order. Thus, for example, the antibody can be joined to either the amino or carboxy terminal of the interferon. The antibody can also be joined to an internal region of the interferon, or conversely, the interferon can be joined to an internal location or to any terminus of the antibody, as long as the attachment does not interfere with binding of the antibody to that target marker (e.g., CD20).

The antibody and the interferon (e.g., IFN-α, IFNβ, etc.) can be attached by any of a number of means well known to those of skill in the art. In certain embodiments, the interferon is conjugated, either directly or through a linker (spacer), to the antibody. In certain embodiments, however, it is preferable to recombinantly express the construct as a fusion protein (e.g., with a single chain antibody, or with one chain of a multi-chain antibody).

Chemical Conjugation of the Targeting Moiety to the Interferon.

In certain embodiments, the targeting moiety (e.g., an anti-CD20 antibody) is chemically conjugated to the interferon (e.g., IFN-α, IFNβ, mutIFNα, etc.) molecule. Means of chemically conjugating molecules are well known to those of skill.

The procedure for conjugating two molecules varies according to the chemical structure of the agent. Polypeptides typically contain variety of functional groups; e.g., carboxylic acid (COOH) or free amine (—NH$_2$) groups that are available for reaction with a suitable functional group on the other peptide, or on a linker to join the molecules thereto.

Alternatively, the antibody and/or the IFN-α can be derivatized to expose or attach additional reactive functional groups. The derivatization can involve attachment of any of a number of linker molecules such as those available from Pierce Chemical Company, Rockford Illinois.

A "linker", as used herein, typically refers to a molecule that is used to join the antibody to the interferon. In various embodiments, the linker is capable of forming covalent bonds to both the antibody and to the interferon. Suitable linkers are well known to those of skill in the art and include, but are not limited to, straight or branched-chain carbon linkers, heterocyclic carbon linkers, or peptide linkers. In certain embodiments, the linker(s) can be joined to the constituent amino acids of the antibody and/or the interferon through their side groups (e.g., through a disulfide linkage to cysteine). In certain preferred embodiments, the linkers are joined to the alpha carbon amino and/or carboxyl groups of the terminal amino acids of the antibody and/or the interferon.

A bifunctional linker having one functional group reactive with a group on the antibody and another group reactive on the interferon, can be used to form the desired conjugate. Alternatively, derivatization can involve chemical treatment of the targeting moiety. Procedures for generation of, for example, free sulfhydryl groups on polypeptides, such as antibodies or antibody fragments, are known (See U.S. Pat. No. 4,659,839).

Many procedures and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075. In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine, Academic Press*, pp. 168-190 (1982); Waldmann (1991) *Science,* 252: 1657; U.S. Pat. Nos. 4,545,985 and 4,894,443, and the like.

Production of Fusion Proteins.

In certain embodiments, a chimeric targeting moiety-interferon fusion protein is synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins or encoding one chain of the antibody attached to an interferon can be prepared by any suitable method, including, for example, cloning and restriction of appropriate sequences or direct chemical synthesis by methods such as the phosphotriester method of Narang et al. (1979)*Meth. Enzymol.* 68: 90-99; the phosphodiester method of Brown et al. (1979)*Meth. Enzymol.* 68: 109-151; the diethylphosphoramidite method of Beaucage et al. (1981) *Tetra. Lett.,* 22: 1859-1862); the solid support method of U.S. Pat. No. 4,458,066, and the like.

Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is limited to sequences of about 300 bases, longer sequences may be obtained by the ligation of shorter sequences.

Alternatively, subsequences can be cloned and the appropriate subsequences cleaved using appropriate restriction enzymes. The fragments can then be ligated to produce the desired DNA sequence.

In certain embodiments, DNA encoding fusion proteins can be cloned using DNA amplification methods such as polymerase chain reaction (PCR). Thus, for example, the gene for IFN-α is PCR amplified, using a sense primer containing the restriction site for, e.g., NdeI and an antisense primer containing the restriction site for HindIII. This can produce a nucleic acid encoding the mature IFN-α sequence and having terminal restriction sites. An antibody having "complementary" restriction sites can similarly be cloned and then ligated to the IFN-α and/or to a linker attached to the IFN-α. Ligation of the nucleic acid sequences and insertion into a vector produces a vector encoding IFN-α joined to the desired antibody.

While the two molecules can be directly joined together, one of skill will appreciate that the molecules can be separated by a single amino acid (e.g., Gly, Pro, etc.) or a peptide spacer consisting of one or more amino acids. Generally, the spacer will have no specific biological activity other than to join the proteins or to preserve some minimum distance or other spatial relationship between them. In certain embodiments, however, the constituent amino acids of the spacer can be selected to influence some property of the molecule such as the folding, net charge, or hydrophobicity.

Accordingly, in certain embodiments, it is desirable to use a linker that is resistant to proteolysis. Certain suitable linkers are linkers that are not or that do not comprise the (Gly4Ser)3 (SEQ ID NO:25) linker. Certain suitable linkers are peptide linkers that are 30 or fewer amino acids, 29 or fewer amino acids, 28 or fewer amino acids, 27 or fewer amino acids, 26 or fewer amino acids, 25 or fewer amino acids, 24 or fewer amino acids, 23 or fewer amino acids, 22 or fewer amino acids, 21 or fewer amino acids, 20 or fewer amino acids, 19 or fewer amino acids, 18 or fewer amino acids, 17 or fewer amino acids, 16 or fewer amino acids, 15 or fewer amino acids, 14 or fewer amino acids, 13 or fewer amino acids, 12 or fewer amino acids, 11 or fewer amino acids, 10 or fewer amino acids, or 9 or fewer amino acids, or 8 or fewer amino acids, or 7 or fewer amino acids, or 6 or fewer amino acids, or 5 or fewer amino acids, or 4 or fewer amino acids, or 3 or fewer, or 2 or fewer amino acids in length, or is a single amino acid.

Certain illustrative linkers suited for use in the targeted interferons used in the methods described herein are shown in Table 5.

TABLE 5

Illustrative linkers.

| Linker Seq | SEQ ID NO |
|---|---|
| GGG | |
| GGS | |
| GGGGS | 26 |
| SGGGGS | 27 |
| GGGGSGGGGS | 28 |
| A EAAAK A | 29 |
| A EAAAK EAAAK A | 30 |
| A EAAAK EAAAK EAAAK A | 31 |
| A EAAAK EAAAK EAAAK EAAAK A | 32 |
| A EAAAK EAAAK EAAAK EAAAK EAAAK A | 33 |
| AEAAAKEAAAKAG | 34 |
| AEAAAKEAAAKAGS | 35 |
| GGGGG | 36 |
| GGAGG | 37 |
| GGGGGGGG | 38 |
| GAGAGAGAGA | 39 |
| RPLSYRPPFPFGFPSVRP | 40 |
| YPRSIYIRRRHPSPSLTT | 41 |
| TPSHLSHILPSFGLPTFN | 42 |
| RPVSPFTFPRLSNSWLPA | 43 |
| SPAAHFPRSIPRPGPIRT | 44 |
| APGPSAPSHRSLPSRAFG | 45 |
| PRNSIHFLHPLLVAPLGA | 46 |
| MPSLSGVLQVRYLSPPDL | 47 |
| SPQYPSPLTLTLPPHPSL | 48 |
| NPSLNPPSYLHRAPSRIS | 49 |
| LPWRTSLLPSLPLRRRP | 50 |
| PPLFAKGPVGLLSRSFPP | 51 |
| VPPAPVVSLRSAHARPPY | 52 |
| LRPTPPRVRSYTCCPTP | 53 |

TABLE 5-continued

Illustrative linkers.

| Linker Seq | SEQ ID NO |
|---|---|
| PNVAHVLPLLTVPWDNLR | 54 |
| CNPLLPLCARSPAVRTFP | 55 |
| LGTPTPTPTPTGEF | 56 |
| EDFTRGKL | 57 |
| L EAAAR EAAAR EAAAR EAAAR | 58 |
| L EAAAR EAAAR EAAAR | 59 |
| L EAAAR EAAAR | 60 |
| L EAAAR | 61 |
| EAAAR EAAAR EAAAR EAAAR | 62 |
| EAAAR EAAAR EAAAR | 63 |
| EAAAR EAAAR | 64 |
| EAAAR | 65 |
| LTEEQQEGGG | 66 |
| TEEQQEGGG | 67 |
| LAKLKQKTEQLQDRIAGGG | 68 |
| LELKTPLGDTTHTCPRCPEPKSCDTPPPCPRCPEPKSCDTPP PCPRCPEPKSCDTPPPCPRCPGG | 69 |
| LEPKSSDKTHTSPPSPGG | 70 |

The nucleic acid sequences encoding the fusion proteins can be expressed in a variety of host cells, including E. coli, other bacterial hosts, yeast, and various higher eukaryotic cells such as the COS, CHO and HeLa cells lines and myeloma cell lines. The recombinant protein gene is typically operably linked to appropriate expression control sequences for each host. For E. coli this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for E. coli and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification, Springer-Verlag, N.Y.: Deutscher* (1990) *Methods in Enzymology* Vol. 182*: Guide to Protein Purification.*, Academic Press, Inc. N.Y., and the like). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the fusion protein (e.g., anti-CCD20-IFN-α14) may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see, e.g., Debinski et al. (1993) *J Biol. Chem.*, 268: 14065-14070; Kreitman and Pastan (1993) *Bioconjug. Chem.*, 4: 581-585; and Buchner, et al. (1992) *Anal. Biochem.*, 205: 263-270). Debinski et al., for example, describe the denaturation and reduction of inclusion body proteins in guanidine-DTE. The protein is then refolded in a redox buffer containing oxidized glutathione and L-arginine.

In certain embodiments a transient expression system can be used to express the chimeric constructs described herein. Although many cell lines potentially can be used, one cell line that works well for transient expression is 293T. For transient expression of 293T on Day 0, 9 million cells in 25 ml are seeded for each 150 mm tissue culture plate. A 1 mg/ml of PEI (Polyethylenimine) is made using sterile water. For the expression of a complete antibody or antibody fusion protein, 25 μg each of H and L (50 ug total) is used per plate. A volume of 5 ml is used for transfection of each 150 mm plate. The DNA is mixed with DMEM, the PEI is then added and the mixture is incubated at room temperature for 10 mins. 1.75 μg PEI is used for each ug of DNA. For transfection, the old medium is removed, discarded and replaced with 20 ml of fresh medium (Iscoves+5% calf serum). The transfection mix is added and the plate is swirled. On Day 2, the medium is replaced with 30 ml of Iscoves medium containing 1% FBS (fetal bovine serum) to minimize the amount of bovine Ig present. Supernatants are collected from the cells on Days 4, 6 and 13 by removing the medium and replacing it with 30 ml of fresh Iscover containing 1% FBS.

One of skill would recognize these expression methods are illustrative and not limiting. Modifications can be made to the fusion proteins described herein without diminishing their activity/efficacy. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

Other modifications can be made to increase serum half-life and/or bioavailability. Such modifications include but are not limited to the incorporation of D amino acids (especially in the linker), the use of non-naturally occurring amino acids, pegylation of the fusion protein, and the like.
Other Multi-Valent Targeting Moieties.

In certain embodiments a targeting moiety comprising a targeted interferon used in the methods described herein comprises a multivalent, trivalent, quadravalent, pentavalent or greater targeting moiety to target the interferon to a target cell.

For example, multivalent anti-CD20 moieties can be produced by any of a number of methods. For example, linkers having three, four, or more reactive sites can be reacted with anti-CD20 antibodies to form a trimer or greater conjugate.

In certain embodiments, phage display, yeast display, bacterial display, or other display systems can be used to express and display multiple copies (e.g., at least 3, at least 4, at least 5, at least 6 copies, etc.) of a targeting antibody and thereby effectively provide a multivalent targeting moiety.

In certain embodiments the use of diabodies and triabodies (e.g., comprising two domains that bind CD20 or one domain that binds CD20 and another domain that binds, for example, another cancer marker on the same cancer. Typically, diabodies comprise a heavy (VH) chain variable domain connected to a light chain variable domain (VL) on the same polypeptide chain (VH-VL) connected by a peptide linker that is too short to allow pairing between the two domains on the same chain. This forces pairing with the complementary domains of another chain and promotes the assembly of a dimeric molecule with two functional antigen binding sites (see, e.g., Holliger et al. (1993) *Proc. Nal. Acad. Sci.*, 90: 6444-6448). In certain embodiments to construct bispecific diabodies the V-domains of antibody A and antibody B are fused to create the two chains VHA-VLB, VHB-VLA. Each chain is inactive in binding to antigen but recreates the functional antigen binding sites of antibodies A and B on pairing with the other chain.

The foregoing antibodies, interferons, and linkers that comprise a targeted interferon are illustrative and non-limiting. Using the teachings provided herein numerous other targeted interferons will be available to one of skill in the art.
Adoptive Cell Therapies.

As explained above, it was discovered that use of a targeted interferon that is targeted to (directed to) the same cancer as an adoptive cell therapy (ACT) can enhance the efficacy of the adoptive cell therapy. Without being bound to a particular theory it is believed the use of a targeted interferon with an adoptive cell therapy can improve T cell recognition of tumor cells, and/or cytotoxicity, and/or activation and survival of an adoptive T cell therapeutic as compared to the use of the adoptive T cell therapeutic in the absence of said targeted interferon.

In certain embodiments, the targeted interferon is administered to a subject prior to the adoptive T cell therapy. This can effectively can prime tumor cells for CAR T (or other adoptive T cell) therapy. In certain embodiments the targeted interferon is administered on conjunction with the adoptive T cell therapy.

Adoptive cell therapy is an emerging therapeutic platform used to induce tumor regression. In addition to virus-specific T cells, two major T-cell sources are typically used to confer these therapeutic properties: (1) tumor-infiltrating lymphocytes (TILs) isolated, activated and expanded ex vivo; (2) peripheral blood T lymphocytes engineered to express conventional alpha/beta T-cell receptors (TCRs) or tumor-recognizing chimeric antigen receptors (CARs). Clinical cell doses of these autologous tumor-reactive lymphocytes can routinely be manufactured and infused after suitable release testing using methods well known to those of skill in the art (see, e.g., Rosenberg et al. (2008) *Nat. Rev. Canc.* 8: 299-308; Restifo et al. (2012) *Nat. Rev. Immunol.* 12: 269-281; Humphries (2013) *Nature,* 504: S13-S15; Maus et al. (2014) *Annu. Rev. Immunol.* 32: 189-225; Yee (2014) *Immunol. Rev.* 257: 250-263; Davila et al. (2012) *Oncoimmunology,* 1: 1577-1583; and the like).
Tumor Infiltrating Lymphocytes (TILs)

Tumor infiltrating lymphocytes (TILs) typically comprise a preparation of cells, consisting of autologous tumor infiltrating lymphocytes, that are manipulated in vitro and, upon administration in vivo, re-infiltrate the tumor to initiate tumor cell lysis. In vitro, therapeutic tumor-infiltrating lymphocytes (TILs) are isolated from tumor tissue and cultured with lymphokines such as interleukin-2; the therapeutic TILs are then infused into the patient, where, after re-infiltration of the tumor, they can induce lysis of tumor cells and tumor regression. The use of therapeutic TILs is considered a form of adoptive immunotherapy.

Infusion of ex vivo-expanded TILs has proven to be a successful treatment regimen for refractory metastatic melanoma (Dudley et al. (2002) Science, 298: 850-854; Dudley et al. (2008) J Cin. Oncol. 26: 5233-5239). The manufacture of tumor antigen-specific lymphocytes used in adoptive cell transfer is typically initiated from tumor fragments or single-cell enzymatic digests of resected tumor specimen. In one illustrative, but non-limiting embodiment, a microculture derived from a single tumor fragment or a plurality (e.g., $10^6$) of viable cells derived from enzymatic digestion are placed into one well of a 24-well plate with high dose interleukin-2 (IL-2). Growth medium is typically changed within 1 week. Confluent wells are subsequently split into daughter wells and maintained as independent TIL cultures for generally ~2 weeks. Cultures are subsequently fed twice per week and maintained at, e.g., 0.8-1.6×$10^6$ cells/mL in flasks. A standard TIL culture typically generates about 5×$10^7$ cells from each original well after 3 to 5 weeks of time. When tumor-reactive TIL cultures are expanded to the minimal requirement of, e.g., 3×$10^7$ cells, independent TIL activity and specificity are determined by measuring interferon-gamma secretion by enzyme-linked immunosorbent assay post stimulation with tumor cells. Active individual TIL cultures are then expanded to therapeutic relevant numbers by using a rapid expansion protocol (see, e.g., Riddell et al. (1990) J Immunol. Meth. 128: 189-201). In one illustrative, but non-limiting embodiment, during the rapid expansion phase, ~$10^6$ TIL effector cells are combined with about 2×$10^8$ irradiated, allogeneic healthy donor peripheral blood mononuclear cell (PBMC) feeder cells in presence of anti-CD3 OKT-3 monoclonal antibody (mAb) and high dose IL-2 in tissue culture flasks. Cell density is determined on day 6 of culture and thereafter to maintain a density of about $10^6$/mL by splitting TIL cultures into flasks or culture bags. IL-2 (e.g., 6000 U/mL) is used throughout the process to promote cell expansion. Within 2 weeks of time since the start of the rapid expansion protocol, cells are harvested, washed, formulated and cryopreserved. The whole manufacture process typically takes about 6-8 weeks (see, e.g., Topalian et al. (1987) J Immunol. Meth. 102: 127-141; Dudley et al. (2003) J Immunother. 26: 332-342). Products meeting standard quality control tests are used for infusion into the patient.

T Cell Receptor Transgenic T Cell (e.g., T Cells Expressing an Exogenous T Cell Receptor (TCR))

The genetic modification of peripheral blood lymphocytes to endow these readily accessible cells with antitumor activity is an attractive approach in the treatment of various cancers. The power and promise of TCR and CAR-T therapy have been demonstrated by encouraging outcomes in patients treated with NY-ESO-1 TCR (see, e.g., Robbins et al. (2011) J Cin. Oncol. 29: 917-924; Hunder et al. (20008) N. Engl. J Med. 358: 2698-2703) and CD19-CAR T cells (see, e.g., Brentjens et al. (2013) Sci. Transl. Med. 5: 177ra38; Grupp et al. (2013) N. Engl. J Med. 368: 1509-1518; Davila et al. (2014) Sci. Transl. Med. 6: 224ra25; Kochenderfer et al. (2014) J Clin. Oncol. 33(6): 540-549). Many ongoing clinical trials utilized genetically modified T cells, and numerous recent papers have reported their clinical success (see, e.g., Aranda et al. (2014) Oncoimmunology, 3: e28344).

One key tool for this genetic modification methodology is the development of RNA vectors expressing TCRs and CARs. T cell receptors (TCRs) can be cloned from the rare occurring patient tumor-reactive T-cell clones (see, e.g., Johnson et al. (2006) J Immunol. 177: 6548-6559), from humanized murine models (see, e.g., Parkhurst et al. (2009) Clin. Cancer Res. 15: 169-180; Cohen et al. (2005) J Immunol. 175: 5799-5808)27,28 or using phage display or yeast display technology (see, e.g., Li et al. (2005) Nat. Biotechnol. 23: 349-354; Varela-Rohena et al. (2008) Nat. Med. 14: 1390-1395).

In one illustrative, but non-limiting embodiment, the manufacture of T cells genetically engineered to express specific TCRs is initiated from Ficoll-purified PBMCs. T cells from PBMCs are activated with OKT-3 antibodies, transduced with a retroviral vector expressing a tumor antigen-specific TCR and cultured for 2 weeks (see, e.g., Morgan et al. (2006) Science, 314: 126-129). Large-scale transduction and expansion under cGMP has been established that is applicable to CAR-T and TCR-T cell manufacturing (see, e.g., Hollyman et al. (2009) J. Immunother. 32: 169-180). The process is initiated from the selection and activation of T cells from patient apheresis products using Dynabeads CD3/CD28. CD3+CD28+ T cells are enriched using a magnetic particle concentrator, and are cultured at, e.g. $10^6$ cells/mL. The activated T cells are transduced with retroviral vectors in RetroNectin-coated cell bags. The retroviral vector-transduced T cells are inoculated in a WAVE bioreactor on day 6 to day 8, and expanded with a continuous perfusion regime. By the end of the production run, the beads are removed with the same magnetic bead concentrator and the cells are formulated for infusion either fresh or frozen. The process typically takes about 2 weeks. This semi-closed large-scale manufacturing platform successfully supports several ongoing clinical trials (see, e.g., 21,23,39,40) and can be easily adapted for other treatments involving the transduction and expansion of autologous or donor T cells.

Efforts have been made to define which T-cell subsets are best suited for use in adoptive therapy to generate cell products enriched for these subsets (see, e.g., Riddell et al. (2014) Cancer J 20: 141-144). In animal models, T-cell transfer studies have shown that effector cells from TEM rapidly undergo apoptosis following adoptive transfer and do not persist beyond 7-14 days, whereas a subset of transferred CD8+TE/CM can reacquire memory cell markers, and persist for years (see, e.g., Wang et al. (2012) J Immunother. 35: 689-701). Consequently, a clinical CD8+ TCM purification, transduction and expansion platform has been developed that incorporates clinical scale polyclonal CD8+ TCM isolation from leukapheresis products, T-cell activation using anti-CD3/CD28 beads without exogenous feeder cells, lentiviral transduction and cell expansion in IL-2/IL-15 (Id.). This process is performed with minimal open processing steps and reproducibly yields cryopreserved cell products in excess of $10^9$ cells within 35 days.

Chimeric Antigen Receptor T Cells (CAR-Ts)

For chimeric antigen receptor T cells (CAR-Ts), tumor recognition is mediated by the single-chain variable fragment derived from a monoclonal antibody or humanized Fab. The rationale and strategy of TCR and CAR design have been comprehensively reviewed (see, e.g., Suerth et al. (2012) Curr. Opin. Immunol. 24: 598-608; Sadelain et al. (2013) Cancer Discov. 3: 388-398; and the like). CAR-T cell therapy is a cellular immunotherapy that involves administration to a mammal having cancer (e.g., a cancer patient) genetically engineered cells (e.g., T cells, a natural killer (NK) cells, a cytotoxic T lymphocytes (CTLs), regulatory T cells, and the like) that express a chimeric antigen receptor (CAR) and that that act on tumor cells (that interact with the CAR) and cause apoptosis of the tumor cells.

Typically, the genetically engineered cells are prepared by expressing on a cell (e.g., a T cell) a CAR having variable regions of an antibody (VL and VH) combined with a CD3 chain (intracellular domain) using gene transfer techniques. CAR is a general term for a chimeric protein in which a light chain (VL) and a heavy chain (VH) of a variable region of a monoclonal antibody specific for a tumor antigen (e.g., an anti-CD19 antibody) are linked in series, which are then linked to a T-cell receptor (TCR) chain at the C-terminal side. More details of CAR-T cell therapy are described, inter alia, by Nakazawa et al. (2013) *Shinshu Med. J* 61(4):197-203.

In certain embodiments the chimeric antigen receptor (CAR) comprises an extracellular and intracellular domain. The extracellular domain comprises a target-specific binding element otherwise referred to as an antigen binding moiety that specifically binds to a cancer cell marker (e.g., CD19, CD20, Tn-MUC, and other markers as described above).

In various embodiments the intracellular domain or otherwise the cytoplasmic domain comprises, one or more costimulatory signaling region(s), and in various embodiments, a zeta chain portion. The costimulatory signaling region refers to a portion of the CAR comprising the intracellular domain of a costimulatory molecule. In various embodiments costimulatory molecules are cell surface molecules other than antigen receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. In various embodiments the spacer domain may comprise up to 300 amino acids, or in various embodiments about 10 to about 100 amino acids, and in certain embodiments about 25 to about 50 amino acids.

CAR Antigen Binding Moiety

In various embodiments the chimeric antigen receptor constructs will comprises a target-specific binding element otherwise referred to as an antigen binding moiety that specifically binds to a cancer marker as described herein. In certain embodiments, the target-specific binding element otherwise referred to as an antigen binding moiety specifically binds to a cancer cell marker (e.g., CD19, CD20, Tn-MUC, and other markers as described above (e.g., a marker shown in Table 1 and/or Table 2).

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

In various embodiments the transmembrane domain can be derived either from a natural or from a synthetic source. Where the source is natural, the domain may be derived from any membrane-bound or transmembrane protein. Illustrative, but non-limiting, examples of transmembrane regions of particular use in the CAR constructs contemplated here can be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively, the transmembrane domain can be synthetic, in which case it can comprise predominantly hydrophobic residues such as leucine and valine. In certain embodiments aa triplet of phenylalanine, tryptophan and valine will be found at each end of a synthetic transmembrane domain. Optionally, a short oligo- or polypeptide linker, e.g., between 2 and about 10 amino acids in length may form the linkage between the transmembrane domain and the cytoplasmic signaling domain of the CAR. In certain embodiments a glycine-serine doublet provides a particularly suitable linker.

In certain embodiment, the transmembrane domain of the CAR comprises a CD8 transmembrane domain. In one illustrative, but non-limiting, embodiment, the CD8 transmembrane domain comprises or consists of the amino acid sequence Ile Trp Ala Pro Leu Ala Gly Thr Cys Gly Val Leu Leu Leu Ser Leu Val Ile Thr Leu Tyr Cys (SEQ ID NO:71). In certain illustrative, but non-limiting embodiments the CD8 transmembrane domain can be encoded by the nucleic acid sequence

```
                                    (SEQ ID NO: 72)
TGTGGGGTCC TTCTCCTGTC ACTGGTTATC ACCCTTTACT GC
ATCTACATCT GGGCGCCCTT GGCCGGGACT.
```

In certain embodiments the transmembrane domain of the CAR can comprise or consist of the CD8a hinge domain. In one illustrative, but non-limiting, embodiment, the CD8a hinge domain comprises or consists of the amino acid sequence Thr Thr Thr Pro Ala Pro Arg Pro Pro Thr Pro Ala Pro Thr Ile Ala Ser Gln Pro Leu Ser Leu Arg Pro Glu Ala Cys Arg Pro Ala Ala Gly Gly Ala Val His Thr Arg Gly Leu Asp Phe Ala Cys Asp Ile Tyr (SEQ ID NO:73). In certain illustrative, but non-limiting embodiments the CD8a hinge domain can be encoded by the nucleic acid sequence

```
                                    (SEQ ID NO: 74)
ACCACGACGC CAGCGCCGCG ACCACCAACA CCGGCGCCCA

CCATCGCGTC GCAGCCCCTG TCCCTGCGCC CAGAGGCGTG

CCGGCCAGCG GCGGGGGGCG CAGTGCACAC GAGGGGGCTG

GACTTCGCCT GTGAT.
```

Cytoplasmic Domain

The cytoplasmic domain or otherwise the intracellular signaling domain of the CAR is responsible for activation of at least one of the normal effector functions of the immune cell in which the CAR has been placed. The term "effector function" refers to a specialized function of a cell. An effector function of a T cell, for example, may be cytolytic activity, or helper activity including the secretion of cytokines. Thus, the term "intracellular signaling domain" refers to the portion of a protein that transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion can be used in place of the intact chain as long as it transduces the effector function signal. The term intracellular signaling domain is thus meant to include any truncated portion of the intracellular signaling domain sufficient to transduce the effector function signal.

Illustrative, but non-limiting examples of intracellular signaling domains for use in the CAR can include a cytoplasmic sequence of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are often insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs that are known as immunoreceptor tyrosine-based activation motifs or ITAMs.

Illustrative, but non-limiting examples of ITAM containing primary cytoplasmic signaling sequences that are of particular use in the CARs contemplated herein invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In one illustrative, but non-limiting embodiment, the cytoplasmic domain of the CAR can be designed to comprise the CD3-zeta signaling domain by itself or combined with any other desired cytoplasmic domain(s) useful in the context of the CAR. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include, but are not limited to, CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. In one illustrative embodiment, the co-stimulatory signaling element comprises 4-1BB.

The cytoplasmic signaling sequences within the cytoplasmic signaling portion of the CAR can be linked to each other in a random or specified order. Optionally, a short oligo- or polypeptide linker, e.g., between 2 and about 10 amino acids in length can form the linkage. In certain embodiments a glycine-serine doublet provides a particularly suitable linker.

In one illustrative but non-limiting embodiment, the cytoplasmic domain is designed to comprise the signaling domain of CD3-zeta and the signaling domain of CD28. In another embodiment, the cytoplasmic domain is designed to comprise the signaling domain of CD3-zeta and the signaling domain of 4-1BB. In yet another embodiment, the cytoplasmic domain is designed to comprise the signaling domain of CD3-zeta and the signaling domain of CD28 and 4-1BB.

In one embodiment, the cytoplasmic domain in the CAR of the invention is designed to comprise the signaling domain of 4-1BB and the signaling domain of CD3-zeta, wherein the signaling domain of 4-1BB comprises or consists of the amino acid sequence Lys Arg Gly Arg Lys Lys Leu Leu Tyr Ile Phe Lys Gln Pro Phe Met Arg Pro Val Gln Thr Thr Gln Glu Glu Asp Gly Cys Ser Cys Arg Phe Pro Glu Glu Glu Glu Gly gly cys Glu Leu (SEQ ID NO:75) and/or the signaling domain of CD3-zeta comprises or consists of the amino acid sequence Arg Val Lys Phe Ser Arg Ser Ala Asp Ala Pro Ala Tyr Lys Gln Gly Gln Asn Gln Leu Tyr Asn Glu Leu Asn Leu Gly ARg Arg Glu Glu Tyr Asp Val Leu Asp Lys Arg Arg Gly Arg Asp Pro Glu Met Gly Gly Lys Pro Arg Arg Lys Asn Pro Gln Glu Gly Leu Tyr Asn Glu Leu Gln Lys Asp Lys Met Ala glu Ala Tyr Ser Glu Ile Gly Met Lys Gly Glu Arg Arg Arg Gly Lys Gly His Asp Gly Leu Tyr Gln Gly Leu Ser Thr Ala Thr Lys Asp Thr Tyr Asp Ala Leu His Met Gln Ala Leu Pro Pro Arg (SEQ ID NO:76.

In one illustrative, but non-limiting embodiment, the signaling domain of 4-1BB is encoded by a nucleic acid sequence that comprises or consists of the sequence

```
                                      (SEQ ID NO: 77)
AAACGGGGCA GAAAGAAACT CCTGTATATA TTCAAACAAC

CATTTATGAG ACCAGTACAA ACTACTCAAG AGGAAGATGG

CTGTAGCTGC CGATTTCCAG AAGAAGAAGA AGGAGGATGT

GAACTG.
```

In one illustrative, but non-limiting embodiment, the signaling domain of CD3-zeta is encoded by a nucleic acid that comprises or consists of the sequence

```
                                      (SEQ ID NO: 78)
AGAGTGAAGT TCAGCAGGAG CGCAGACGCC CCCGCGTACA

AGCAGGGCCA GAACCAGCTC TATAACGAGC TCAATCTAGG

ACGAAGAGAG GAGTACGATG TTTTGGACAA GAGACGTGGC

CGGGACCCTG AGATGGGGGG AAAGCCGAGA AGGAAGAACC

CTCAGGAAGG CCTGTACAAT GAACTGCAGA AAGATAAGAT

GGCGGAGGCC TACAGTGAGA TTGGGATGAA AGGCGAGCGC.
```

The foregoing embodiments are illustrative and non-limiting. Using the teachings provided herein numerous CARs directed against CD146 (aka Muc18 or MCAM) will be available to one of skill in the art.

Vectors

In various embodiments a DNA construct comprising sequences of a CAR as described herein is provided. In certain embodiments the CAR comprising an antigen binding moiety that specifically binds to a cancer marker ((e.g., CD19, CD20, Tn-MUC, and other markers as described above) where the nucleic acid sequence of the antigen binding moiety is operably linked to the nucleic acid sequence of an intracellular domain. An exemplary intracellular domain that can be used in the CAR of the invention includes but is not limited to the intracellular domain of CD3-zeta, CD28, 4-1BB, and the like. In some instances, the CAR can comprise any combination of CD3-zeta, CD28, 4-1BB, and the like.

In one embodiment, the CAR of the invention comprises an antibody as described above in single chain form (e.g., scFv), a human CD8 hinge and transmembrane domain, and human 4-1BB and CD3zeta signaling domains.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

In certain embodiments vectors are provided in which a nucleic acid sequence encoding a CAR as described herein is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs can be achieved by operably linking a nucleic acid encoding the CAR polypeptide or portions thereof to a promoter and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs described herein can also be used for nucleic acid immunization and gene therapy, using standard gene delivery protocols. Methods for gene delivery are known in the art (see, e.g., U.S. Pat. Nos. 5,399,346, 5,580,859, and 5,589,466). In certain embodiments gene therapy vectors are provided.

The nucleic acid encoding the CAR can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

In certain embodiments the expression vector may be provided to a cell in the form of a viral vector. Viral vector technology is well known in the art and is described, for example, in Sambrook et al. (2001) Molecular Cloning: A Laboratory Manual, Cold Spring Harbor Laboratory, New York), and in other virology and molecular biology manuals. Viruses that are useful as vectors include, but are not limited to, retroviruses, adenoviruses, adeno-associated viruses, herpes viruses, and lentiviruses (including self-inactivating lentivirus vectors). In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1alpha (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Moreover, the constructs are not be limited to the use of constitutive promoters and inducible and/or tissue-specific promoters are also contemplated. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In certain embodiments, in order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes can be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al. (2000) *FEBSLetts.* 479: 79-82). Suitable expression systems are well known and may be prepared using known techniques or obtained commercially. In general, the construct with the minimal 5' flanking region showing the highest level of expression of reporter gene is identified as the promoter. Such promoter regions can be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art (see, e.g., Sambrook et al. (2001) Molecular Cloning: A Laboratory Manual, Cold Spring Harbor Laboratory, New York). One illustrative, but non-limiting method for the introduction of a polynucleotide into a host cell is calcium phosphate transfection.

Biological methods for introducing a polynucleotide of interest into a host cell can include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like (see, e.g., U.S. Pat. Nos. 5,350,674 and 5,585,362, and the like).

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An illustrative colloidal system for use as a delivery vehicle in vitro and in vivo is a liposome (e.g., an artificial membrane vesicle).

In the case where a non-viral delivery system is utilized, one illustrative delivery vehicle is a lipid and/or a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

In various embodiments lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform can be used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al. (1991) *Glycobiology* 5: 505-510). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Sources of Immune Cells

In certain embodiments prior to expansion and genetic modification of the immune cells (e.g. T cells) described herein, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as FICOLL™ separation. In one illustrative embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed, and the cells directly resuspended in culture media.

In another illustrative embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28-conjugated beads, such as DYNABEADS® M-450 CD3/CD28 T, for a time period sufficient for positive selection of the desired T cells. In one illustrative embodiment, the time period is about 30 minutes. In certain illustrative embodiments, the time period ranges from 30 minutes to 36 hours or longer and all integer values there between. In certain embodiments the time period is at least 1, 2, 3, 4, 5, or 6 hours. In yet another embodiment, the time period is 10 to 24 hours. In one embodiment, the incubation time period is 24 hours. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells that typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one illustrative embodiment, a concentration of 1 billion cells/ml is used. In another embodiment, greater than 100 million cells/ml is used. In another illustrative embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In another embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In another embodiment, the concentration used can be from about $1\times10^5$/ml to $1\times10^6$/ml, and any integer value in between.

In certain embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C., e.g., at a rate of 1° C. per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, the T cells may be expanded, frozen, and used at a later time. In certain embodiments, samples are collected from a patient shortly after diagnosis of a particular disease (e.g., a cancer such as mesothelioma) as described herein but prior to any treatments. In a further embodiment, the cells are isolated from a blood sample or an apheresis from a subject prior to any number of relevant treatment modalities, including but not limited chemotherapy, surgery, and/or radiotherapy.

In certain embodiments T cells are obtained from a subject directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable CAR (e.g., a CAR described herein) or TCR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Publication No: 2006/0121005.

In various embodiments the T cells are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For costimulation of an accessory molecule on the surface of the T cells, a ligand that binds the accessory molecule can be used. For example, a population of T cells can be contacted with an anti-CD3 antibody and an anti-CD28 antibody, under conditions appropriate for stimulating proliferation of the T cells. To stimulate proliferation of either CD4$^+$ T cells or CD8$^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (see, e.g., Berg et al. (1998) *Transplant Proc.* 30(8):3975-3977, 1998; Haanen et al. (1999) *J Exp. Med.* 190(9): 1319-1328; Garland et al. (1999) *J Immunol Meth.* 227(1-2):53-63, and the like).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent that will bind to the agents (see, e.g., U.S. Patent Pub. Nos. 2004/0101519 and 2006/0034810 for artificial antigen presenting cells (aAPCs) that are contemplated for use in activating and expanding T cells in the present invention).

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof, and both agents are co-immobilized to the same bead in equivalent molecular amounts. In one embodiment, a 1:1 ratio of each antibody bound to the beads for CD4+ T cell expansion and T cell growth is used. In certain embodiments, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect, more anti-CD28 antibody is bound to the particles than anti-CD3 antibody, i.e., the ratio of CD3:CD28 is less than one. In certain embodiments, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

In certain embodiments ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable. In particular, ratios will vary depending on particle size and on cell size and type.

In certain embodiments the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, 10 to 10 T cells) and beads (for example, DYNABEADS® M-450 CD3/CD28 T paramagnetic beads at a ratio of 1:1) are combined in a buffer, e.g., PBS (without divalent cations such as, calcium and magnesium).

Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one illustrative embodiment, the mixture may be cultured for several hours (about 3 hours) to about 14 days or any hourly integer value in between. In another embodiment, the mixture may be cultured for 21 days. In one embodiment the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-$\gamma$., IL-4, IL-7, GM-CSF, IL-10, IL-12, IL-15, TGF-$\beta$, and TNF-$\alpha$ or any other additives for the growth of cells known to the skilled artisan. Other additives for the growth of cells include, but are not limited to, surfactant, plasmanate, and reducing agents such as N-acetyl-cysteine and 2-mercaptoethanol. In certain embodiments media can include RPMI 1640, AIM-V, DMEM, MEM, $\alpha$-MEM, F-12, X-Vivo 15, X-Vivo 20, and the like. Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, can be included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population ($T_C$, CD8$^+$). Ex vivo expansion of T cells by stimulating CD3 and CD28 receptors produces a population of T cells that prior to about days 8-9 consists predominately of TH cells, while after about days 8-9, the population of T cells comprises an increasingly greater population of Tc cells. Accordingly, depending on the purpose of treatment, infusing a subject with a T cell population comprising predominately of TH cells may be advantageous. Similarly, if an antigen-specific subset of T-cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

EXAMPLES

The following examples are offered to illustrate, but not to limit the claimed invention.

Example 1

Activity of Anti-CD19 CAR T Cells Against B Cell Lymphoma is Enhanced by Antibody-Targeted Interferon-Alpha An important emerging form of immunotherapy targeting B cell malignancies is chimeric antigen receptor (CAR) T cell therapy. Despite encouraging response rates of anti-CD19 CAR T cell therapy in B cell lymphomas, limited durability of response necessitates further study to potentiate CAR T cell efficacy. Antibody-targeted interferon (IFN) therapy is a novel approach in immunotherapy. Given the ability of IFNs to promote T cell activities including recognition of tumor cells, cytotoxicity, activation and survival, we asked whether antibody-targeted IFN could enhance the antitumor effects of anti-CD19 CAR T cells. We produced an anti-CD20-IFN fusion protein containing the potent type I IFN isoform alpha14 (α4), and demonstrated its ability to suppress proliferation and induce apoptosis of human B cell lymphomas. Indeed, with the combination of anti-CD20-hIFNα14 and CAR T cells, we found enhanced cell killing among B cell lymphoma lines. Importantly, in all cell lines pretreated with anti-CD20-hIFNα14, the cytokine production by CAR T cells was markedly increased regardless of the degree of cell killing. Thus, several activities of CD19 CART cells were enhanced in the presence of anti-CD20-hIFNα14. These data suggest that antibody-targeted IFN may be an important novel approach to improving the efficacy of CAR T cell therapy.

Materials and Methods

Cell Lines

Raji, Daudi, DEL, Granta-519, Jeko-1, OCI-Ly2, OCI-Ly19, and RS-27 cell lines were obtained and cultured as previously described (Andorsky and others 2011). OVCAR-3 was a gift from Dr. Gottfried Konecny (UCLA). Unless otherwise specified, tumor cells were cultured in RPMI 1640 medium (ThermoFisher Scientific, Waltham, MA) plus 10% heat-inactivated fetal calf serum (FCS; Omega Scientific, Tarzana, CA), 100 units/mL penicillin/streptomycin, 2 mmol/L L-glutamine, and 50 µmol/L β-mercaptoethanol ("RPMI complete medium"; all supplements from ThermoFisher Scientific), at 37° C. in 5% CO2. OVCAR-3 was grown in RPMI supplemented with 20% fetal bovine serum (FBS) (Atlanta Biologics, Lawrenceville, GA)+0.01 mg/mL bovine insulin (Sigma-Aldrich, St. Louis, MO).

Construction of Expression Vectors

The DNA sequence for human interferon α14 (Genbank accession #NP002163.2) optimized for expression in Chinese Hamster Ovary (CHO) cells was synthesized by DNA 2.0 with a BamHI restriction site (GGATCC) added 5' of the mature protein sequence, and an XbaI site (TCTAGA) added 3' of the termination sequence. The hIFNα14 gene was cloned into the anti-huCD20 or anti-huCD138 expression vectors (Xuan and others 2010; Yoo and others 2015) as a BamHI/XbaI cassette.

Protein Production and Purification

Protein production and purification were done using protein A Sepharose as previously described except the bound protein was eluted with 0.1 M arginine pH 2.5 (Trinh and others 2013). Recombinant hIFNα14 reference standard was purchased from PBL InterferonSource (Piscataway, NJ). Rituximab was obtained from Genentech (South San Francisco, CA).

Determination of Binding to CD20

Daudi cells were harvested by washing once in PBS+2% bovine serum albumin (FACS buffer), and incubated on ice as follows 1) unstained, 2) 15 µg/mL mouse anti-human IgG1 Fd (Hamilton and Morrison 1993)+4 µL anti-mouse kappa phycoerythrin (PE) (Invitrogen/ThermoFisher Scientific), 3) 10 µg/mL rituximab+15 µg/mL mouse anti-human IgG1 Fd+4 µL anti-mouse kappa PE, or 4) 10 µg/mL anti-huCD20-hIFNα14+15 µg/mL mouse anti-human IgG1 Fd+4 µL anti-mouse kappa PE. Each sample was incubated for 1 hour and washed twice with FACS buffer before the next incubation. All samples stained with anti-mouse kappa PE were incubated for 30 minutes. Samples were run on a FACSCalibur flow cytometer (BD Biosciences, San Jose, CA) and analyzed using FlowJo software (Tree Star Inc., Ashland, OR).

Flow Cytometry for Cell Surface Markers

Lymphoma cells were added to 6-well plates with medium or graded concentrations of rituximab (10 or 1 nM), anti-huCD20-hIFNα14 (10 or 1 nM), or rhIFNα14 (20 or 2 nM) and incubated for 24 or 48 hours. Equimolar amounts of antibody and an equivalent rhIFNα14 dose (assuming 2 moles of IFN for every mole of fusion protein) were used. Cells were then stained with anti-human PD-L1/B7-H1 PE (clone MIH1) or anti-human CD19 PE (clone HIB19) (eBioscience/ThermoFisher Scientific) or appropriate isotype controls from BD Biosciences and analyzed using a BD FACSVerse flow cytometer (BD Biosciences) with FCS Express software (De Novo Software, Los Angeles, CA).

Metabolic Activity Assay

Daudi cells in RPMI complete medium were plated in triplicate in 96-well flat bottom plates. Antibodies were added in RPMI complete medium to wells in triplicate starting at 0.5 nM and serially diluted 1:5. Cells alone plus RPMI complete medium served as the no treatment control. Cells were incubated at 37° C. for 72 hours prior to performing the MTS assay (Promega, Madison, WI) according to the manufacturer's protocol. Absorbance was measured at 490 nm using a Synergy HT Multi-Detection Microplate Reader (BioTek Instruments, Inc., Winooski, VT). Data were analyzed by non-linear regression using Prism (GraphPad Software, Inc., La Jolla, CA) with the log [inhibitor] vs. the response with a variable slope with the $IC_{50}$ calculated. Data are expressed as the percentage of maximum metabolic activity of untreated cells. OVCAR-3 cells were assayed similarly, using RPMI 1640 medium+20% FBS+0.01 mg/mL bovine insulin (Sigma-Aldrich) and 1:10 antibody dilutions were made starting at 50 nM. The bioactivity of the antibodies was plotted adjusting for the fact that there are two IFNs per antibody molecule.

Apoptosis Assay

Tumor cells were seeded in a 24-well plate in RPMI complete medium. Medium or graded concentrations of rituximab (10, 1, or 0.1 nM), anti-CD20-hIFNα14 (10, 1, or 0.1 nM) or rhIFNα14 (2 or 0.2 nM) were added at a final volume of 1 mL/well and incubated for 72 hours. Apoptosis was assessed by Annexin V-fluorescein isothiocyanate (FITC)/propidium iodide (PI) staining per manufacturer's protocol (Roche Applied Science, Indianapolis, IN) and stained cells were analyzed using a BD FACSCalibur flow cytometer (BD Biosciences) and FCS Express version 5 software (De Novo Software). Data are displayed as mean±SD for triplicate values of % Annexin V-positive cells.

Proliferation Assay

Human lymphoma cell lines were incubated in 96-well U-bottom plates (Nunc, Rochester, NY) with medium, rituximab, anti-CD20-hIFNα14, or rhIFNα14 (starting at 10 nM or 1 nM and serially diluted 10-fold) for 72 hours. DEL, a CD19-negative cell line, was used as a negative control for the tumor mixture assay. Equimolar amounts of antibody and an equivalent rhIFNα14 dose (assuming 2 moles of IFN for every mole of fusion protein) was used to compare to anti-CD20-hIFNα14 and plotted accordingly for direct comparison. Cells were pulsed with 1 µCi/well 3[H]-thymidine (PerkinElmer, Waltham, MA) and harvested 8 hours later. Incorporated radioactivity (counts per minute) was measured using a β-liquid scintillation analyzer (PerkinElmer) and percent proliferation was calculated as [cpm(expt)/cpm (untreated)]*100 and shown as mean+SD of quadruplicate values. Dose response curves were generated using non-linear regression analysis using Prism (Graphpad software).

Preparation of Chimeric Antigen Receptor T Cells

Primary Human T Cells

Peripheral blood mononuclear cells (PBMC) were isolated from blood from anonymous donors through Ficoll-Paque Plus (GE Healthcare Life Sciences, Marlborough, MA) density gradient separation. Dynabeads® Human T-Activator CD3/CD28 beads (ThermoFisher Scientific) were then used to activate T lymphocytes for 72 hours. After 72 hours, T cells were harvested for bead removal through a magnetic column system, and immediately incubated with lentiviral vectors for transduction (De Oliveira and others 2013). A portion of the activated T cells harvested were set aside and designated Mock (non-transduced) T cells to be used as an experimental control. All cells were cultured in RPMI 1640 plus 10% FBS (R10) with 10 ng/mL of rhIL-2 (R&D Systems, Minneapolis, MN) 24 hours after lentiviral transduction, for up to 21 days.

Lentiviral Vector Construct and Production

The lentiviral vector used has been described previously (De Oliveira and others 2013; Kowolik and others 2006; Larson and others 2017). In brief, the third-generation self-inactivating lentiviral vector utilized the pCCL-c backbone (Dull and others 1998) and contained the MND LTR U3 (MNDU3) (Challita and others 1995) promoter to deliver a single chain variable fragment (scFv) specific for CD19 connected to CD28 co-stimulatory moiety and the intracellular domain of the human CD3ζ T cell intracellular domain (Cooper and others 2003). Lentiviral supernatant was created through triple transfection of 293T cells with gag/pol plasmid, VSV-G envelope plasmid, and the anti-CD19 CAR plasmid. High-titer vectors were produced by tangential flow filtration (Cooper and others 2011). Vector titer determination to define vector transduction units per volume (TU/mL) was performed through transduction of HT-29 cells with three independent dilutions of $10^{-1}$ vector, harvested after 72 hours for ddPCR of the extracted DNA (Cooper and others 2011). For all determinations of vector copy number, the HIV-1 ψ region of the vector provirus was detected.

T Cell Lentiviral Transduction and Culture

After removal of immunomagnetic beads, 0.4-0.5×$10^6$ T cells/well of a non-tissue-culture-treated plate were incubated for 24 hours in R10 medium with 1-1.5×$10^8$ TU/mL of lentiviral vector, in wells coated with RetroNectin (Clontech T100B). Cells were then removed and cultured in R10 with 10 ng/mL of rhIL-2 (R&D Systems) (De Oliveira and others 2013; Larson and others 2017). For the cytotoxicity assays, cells were used 14-21 days after transduction.

Cytotoxicity Assays

Tumor Mixture Assay

CD19-negative and CD19-positive human lymphoma cells were harvested, washed in 1×PBS and stained with 0.25 µM or 5 µM carboxyfluorescein succinimidyl ester (CFSE, ThermoFisher Scientific), respectively for 10 minutes in a 37° C. water bath. After incubation 5 mL of FCS was added and cells centrifuged at 400×g for 7 minutes. Supernatant was removed and cells were washed 2 times with RPMI complete medium. Stained CD19-negative and -positive cell lines (targets) were mixed at an approximate 1:1 ratio, and plated in 96-well U-bottom plates at 10,000 cells/well. Day 14 post-transduction effectors (CD19 CAR or Mock T cells) were harvested, washed and added at 125:1, 25:1, 5:1, or 1:1 effector:target (E:T) ratios. Plates were incubated for 2 hours at 37° C. in a 5% CO2 humidified incubator. Cells were then stained with PI and analyzed immediately using a FACSVerse flow cytometer (BD Biosciences) and FCS Express (De Novo Software).

$$\text{Percent specific lysis} = 100 * (1 - (\text{controlCFSE}_{low}/\text{controlCFSE}_{high})/(\text{exptCFSE}_{low}/\text{exptCFSE}_{high})).$$

Fusion Protein Plus CAR T Cell Killing Assay

Human lymphoma cells were pretreated with either medium or graded concentrations of rituximab (10, 1, or 0.1 nM) or anti-CD20-hIFNα14 (10, 1, or 0.1 nM) for 18-24 hours and incubated at 37° C. in a 5% CO2 humidified incubator. After incubation, cells were harvested and washed twice in cold 1×PBS and kept on ice. Cell pellets were stained with 5 µM CFSE for 10 minutes in a 37° C. water bath. After staining, 5 mL of FCS was added and cells centrifuged for 7 minutes at 400×g. Supernatants were removed and cells were washed twice in killing assay complete medium (RPMI complete medium plus 1 mM sodium pyruvate, 10 mM HEPES, and 1×MEM NEAA; ThermoFisher Scientific). 10,000 target cells/well were plated onto 96-well U-bottom plates. Medium or graded concentrations of rituximab or anti-CD20-hIFNα14 were added back at the pretreatment concentrations to the appropriate wells for 30 minutes before CD19 CAR or Mock T cells (effectors) were harvested and added at the designated E:T ratios. For the experiments in which soluble fusion protein was not added back, CD19 CAR or Mock T cells were harvested and added at the designated E:T ratios with no additional treatment. Plates were spun at 200×g for 3 minutes and co-cultured at 37° C. for 24 hours. After incubation, plates were spun at 400×g for 5 minutes and supernatant collected for multiplex cytokine ELISAs and/or cells were transferred to V-bottom plates and spun at 400×g for 5 minutes and cell pellets washed twice in 200 µL/well of 1×PBS. Cells were stained with LIVE/DEAD far red fixable dead cell stain (ThermoFisher Scientific) per manufacturer's protocol and fixed using 1-2% paraformaldehyde and transferred to cluster tubes (Corning, ThermoFisher Scientific). CountBright beads (ThermoFisher Scientific) were added (25 µL/tube) and 9,000-12,000 beads were acquired using a FACSVerse flow cytometer (BD Biosciences) in triplicate. Data were analyzed using FlowJo software (Tree Star Inc.) and percent total killing calculated as [% dead target cells with treatment]−[% dead target cells without treatment].

Cytokine Multiplex Immunoassay

Supernatants from the cell killing assays as described above were collected and analyzed for IFNγ, IL-2, IL-4, IL-6, IL-10 and TNFα by Ciraplex™ cytokine immunoassay kit (Aushon BioSystems, Billerica, MA) following the manufacturer's protocol at the indicated E:T ratios. Recombinant proteins were used to generate a standard curve and pg/mL concentrations graphed as mean±SD of duplicate samples.

Statistical Analysis

Apoptosis data were analyzed using the unpaired, two-tailed Student's t test. Cell killing and cytokine secretion assays were analyzed using an unpaired t test with the Holm-Sidak correction method with Prism (Graphpad software). A p value less than 0.05 was considered statistically significant.

Results

Production and Characterization of Anti-CD20-hIFN014 Fusion Protein

Figure 2:
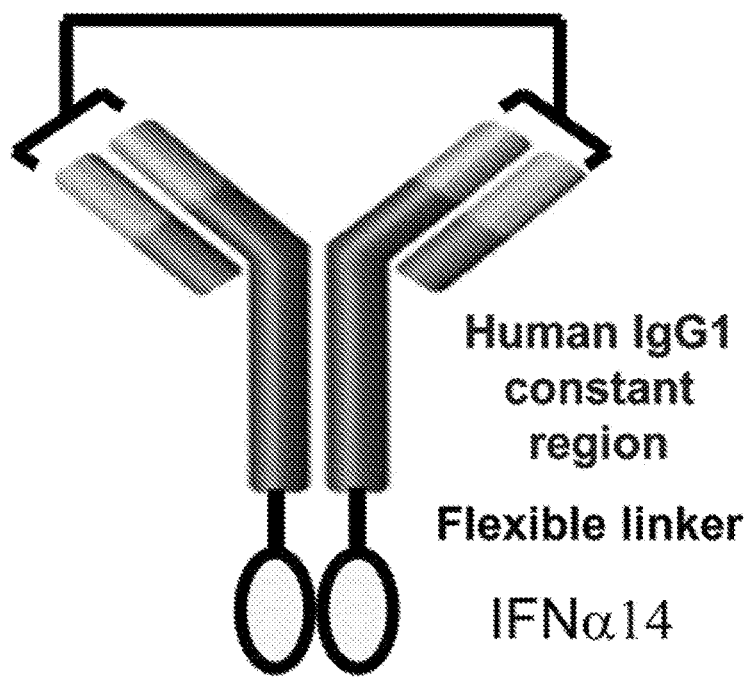
FIG. 2, panels A-D, illustrates the characterization of anti-CD20-hIFNα14 fusion protein. Panel A) Diagram of the fusion protein in which hIFNα14 was joined to the C-terminus of human γ1 heavy chains specific for CD20. The heavy chains were expressed with the appropriate light chain to generate the antigen-specific fusion protein. Panel B) Anti-CD20-hIFNα14 retains the ability to bind to CD20 similar to rituximab. Daudi tumor cells were treated with medium, rituximab or anti-CD20-hIFNα14 fusion protein and analyzed by flow cytometry using FlowJosoftware. Panel C) Anti-CD20-hIFNα14 retains IFN activity and shows superior growth inhibition with antigen specific targeting. OVCAR-3 (CD20-negative) or Daudi (CD20-positive) cells were treated with graded concentrations of recombinant IFNα14 (rhIFNα14), anti-CD20 (rituximab), non-targeted IgG1-hIFNα14 (anti-CD138-hIFNα14), or anti-CD20-hIFNα14 and incubated for 72 hours before an MTS assay was performed to measure percent proliferation. Data are shown as percent proliferation of the mean±SD of triplicates. Panel D) Anti-CD20-hIFNα14 induces more apoptosis than rituximab. Tumor cells were treated with medium or graded concentrations of rituximab, anti-CD20-hIFNα14, or rhIFNα14 as indicated and incubated for 72 hours. Apoptosis was assessed by Annexin V-FITC/PI staining and analyzed by flow cytometry. Data are displayed as mean±SD for triplicate values of % Annexin V-positive cells. Rit=rituximab and FP=anti-CD20-hIFNα14. * $p<0.005$ comparing Rit and FP.
Figure 2:
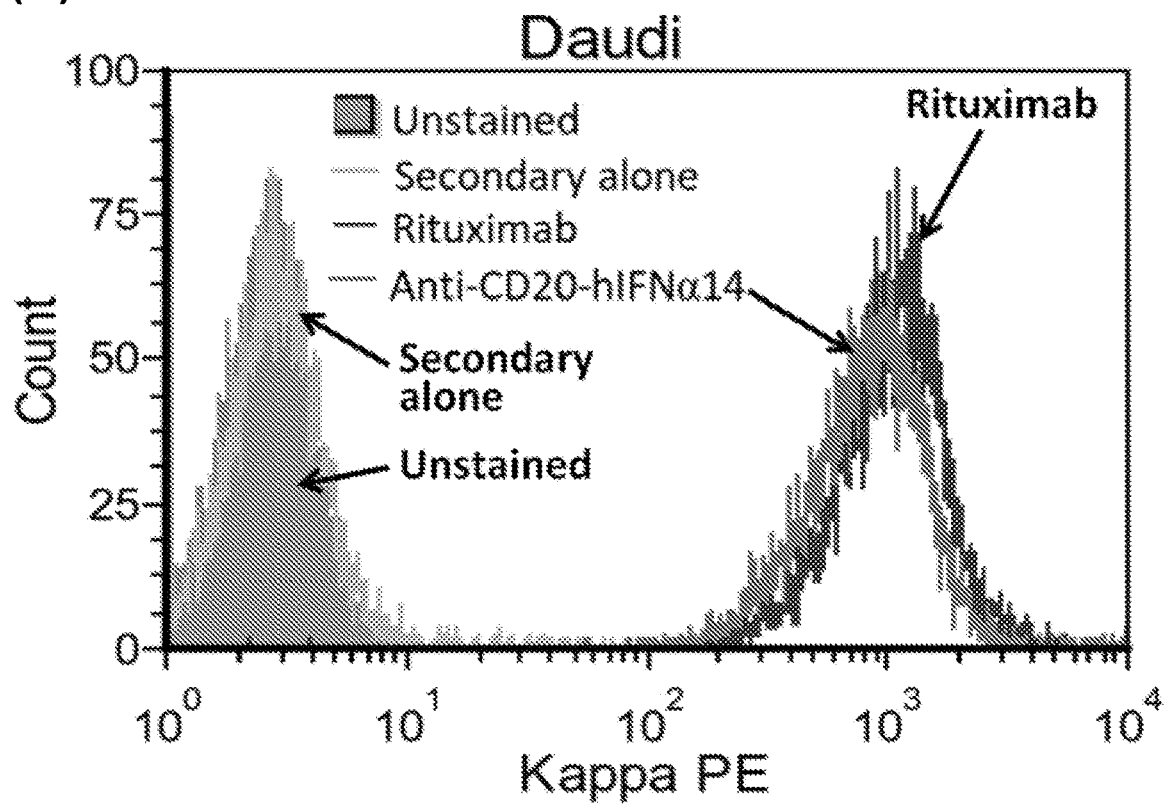

Anti-CD20-hIFNα4 consists of IFNα14 genetically fused by a SGGGGS linker to the end of the $C_H3$ domain of human IgG1 containing the V regions of the anti-CD20 antibody, rituximab (Xuan and others 2010) (FIG. 2, panel A). As a non-CD20 targeting control, IFNα14 was similarly fused to an anti-CD138 antibody (Yoo and others 2015).

Anti-CD20-hIFNα4 and rituximab showed similar binding to CD20-expressing Daudi cells (FIG. 2, panel B). Treatment of lymphoma cells with anti-CD20-hIFNα14 had minimal effect on the expression of CD19, with only slight downregulation amongst several cell lines tested including Daudi, Raji, Granta-519, Jeko-1, and OCI-Ly2 (data not shown). There was no upregulation in PD-L1 expression under these same conditions (data not shown). The CD20-negative cell line, OVCAR-3 was used to evaluate the anti-proliferative activity of the untargeted IFNα14 in the fusion protein. Anti-CD20-hIFNα14 retained IFNα14 activity with an IC50 of 115.2 μM, but is attenuated when compared to rhIFNα14 with an IC50 of 3.7 μM (FIG. 2, panel C, left panel). However, with Daudi, an IFNα-sensitive CD20-positive cell line, anti-CD20-hIFNα14 showed superior growth inhibition compared to rhIFNα14 (IC50 of 0.47 μM compared to IC50 of 1.17 μM) (FIG. 2, panel C, right panel). A non-targeted control fusion protein anti-CD138-hIFNα14 showed less activity (IC50 of 2.95 μM) compared to targeted anti-CD20-hIFNα14. Anti-CD20 (rituximab) did not inhibit the proliferation of Daudi under these conditions. Thus anti-CD20-hIFNα14 has potent anti-proliferative activity which is enhanced by targeting to the target cell surface.

Anti-CD20-hIFN14 Induces Increased Apoptosis Among B Cell Lymphoma Cell Lines Compared to Rituximab To evaluate whether anti-CD20-hIFNα14 was more effective in promoting apoptosis compared to equimolar concentrations of rituximab or equivalent concentrations of rhIFNα14, a panel of cell lines including OCI-Ly19, Daudi, Jeko-1, and OCI-Ly2 was incubated with graded concentrations of anti-CD20-hIFNα14, rituximab, or rhIFNα14. At all concentrations anti-CD20-hIFNα14 was more effective in causing apoptosis compared to rituximab with p<0.005 for all cell lines (FIG. 2, panel D). Even with its attenuated IFNα bioactivity, anti-CD20-hIFNα14 had comparable or improved effectiveness in causing apoptosis compared to rhIFNα14, except for OCI-Ly2 where rhIFNα14 was superior.

Anti-CD20-hIFNα14 Inhibits Proliferation of CD20-Positive Lymphoma Cell Lines

Figure 3:
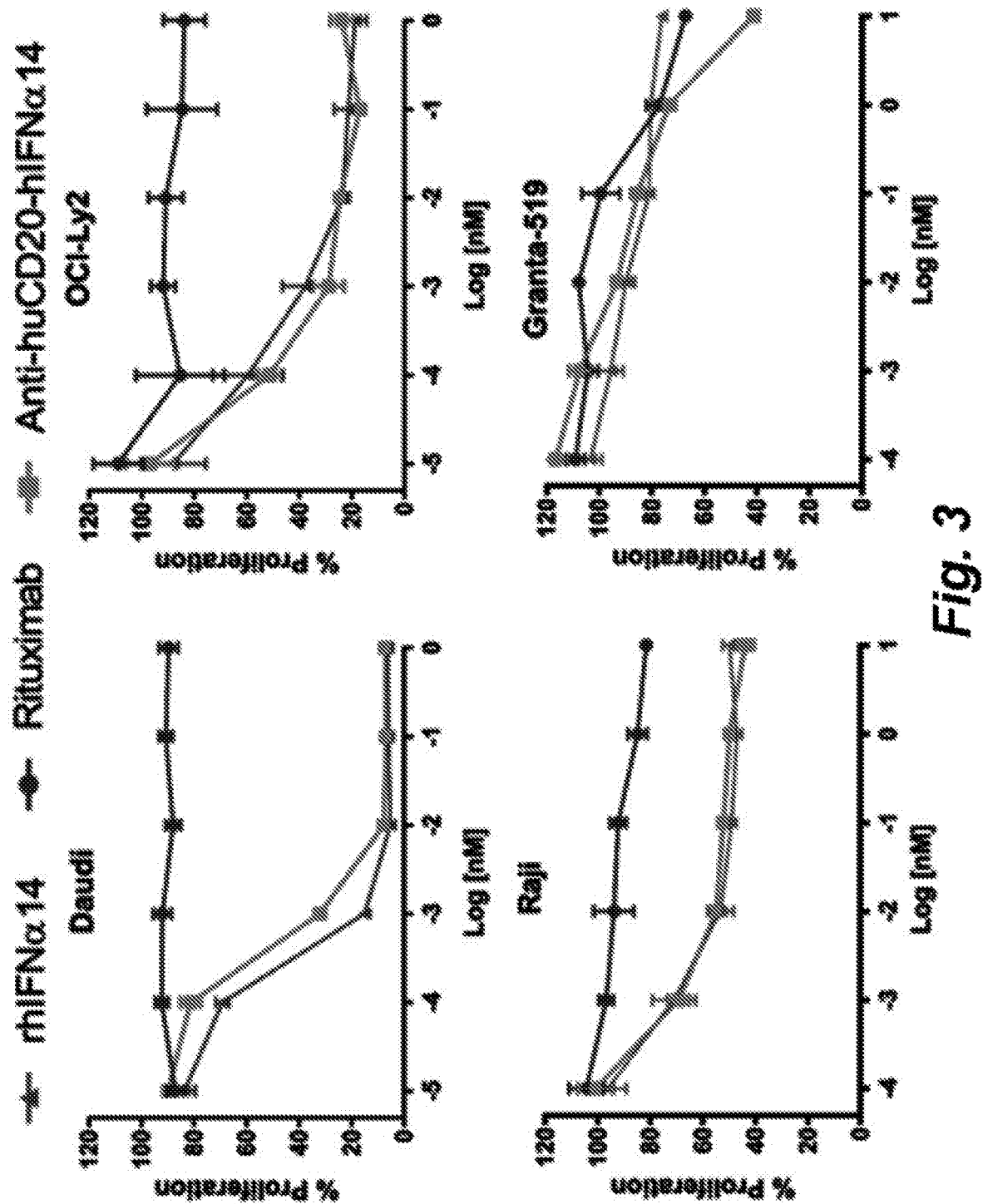
FIG. 3 shows that anti-CD20-hIFNα14 potently inhibits the proliferation of human B cell lymphomas over rituximab. Tumor cells were treated with medium, rituximab, anti-CD20-hIFNα14, or rhIFNα14 as shown and incubated for 72 hours or 24 hours (DEL). Cells were pulsed with 3[H]-thymidine and incorporated radioactivity (counts per minute) was measured using a β-liquid scintillation analyzer. Percent proliferation was calculated and shown as mean±SD of quadruplicate values.

We then examined the growth inhibitory properties of anti-CD20-hIFNα14 against CD20-positive human B cell lymphoma lines representing different histologies. This panel included Burkitt lymphomas (Daudi, Raji), germinal center B cell (GCB) DLBCLs (OCI-Ly2, OCI-Ly19), mantle cell lymphomas (MCL) (Jeko-1, Granta-519), and an early passage DLBCL established in our laboratory (RS-27) (FIG. 3). Anti-CD20-hIFNα14 was more effective than rituximab at inhibiting the proliferation of all cell lines and similar to rhIFNα14. The CD20-negative anaplastic large cell lymphoma cell line (DEL), used as a negative control in the tumor mixture assay, showed no difference in percent proliferation when incubated with anti-CD20-hIFNα14 or rituximab. Given the activities of anti-CD20-hIFNα14, we hypothesized that CD19 CAR T cells may have enhanced killing when given in combination with anti-CD20-hIFNα14.

Anti-CD19 CAR T Cells Specifically Lyse CD19-Positive Lymphoma Cells

Figure 4:
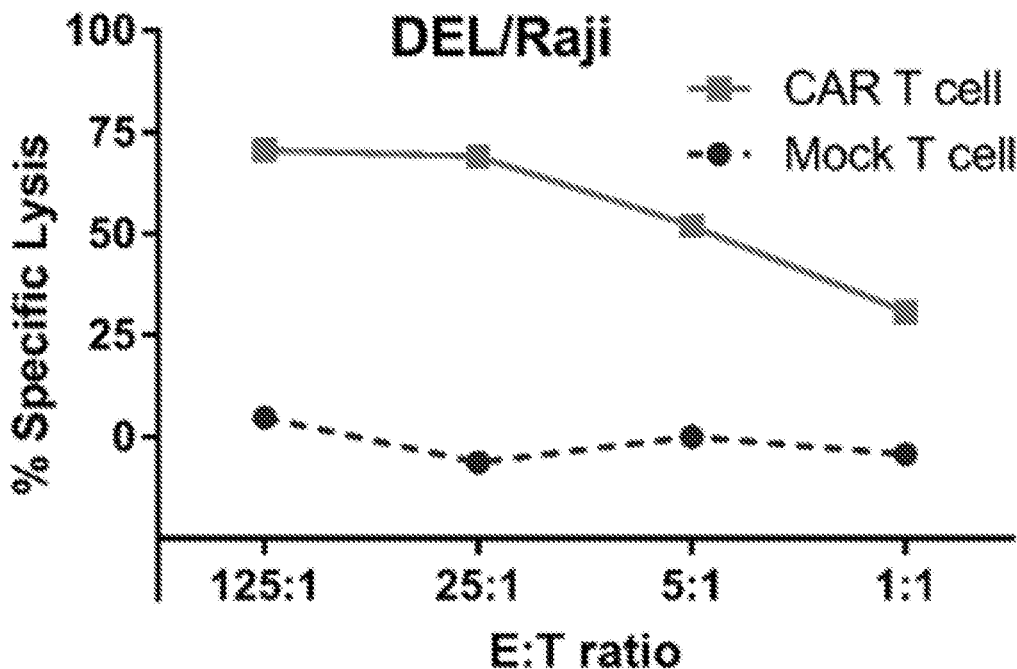
FIG. 4 shows the cytolytic activity of CD19 CAR T cells against lymphoma cells. Mixtures of DEL (CD19−, CFSE low) and Raji (CD19+, CFSE high) tumor cells (targets) were plated with day 14 post-transduction CD19 CAR or Mock T cells (effectors) at the designated effector:target (E:T) ratios. Plates were incubated for 2 hours at 37° C. and then cells were stained with PI and analyzed immediately by flow cytometry and shown on the right in histograms as % gated of M1 or M2 and on left as % specific lysis. Tumor mixture cells alone with no added effector cells is shown below the % specific lysis graph.
Figure 4:
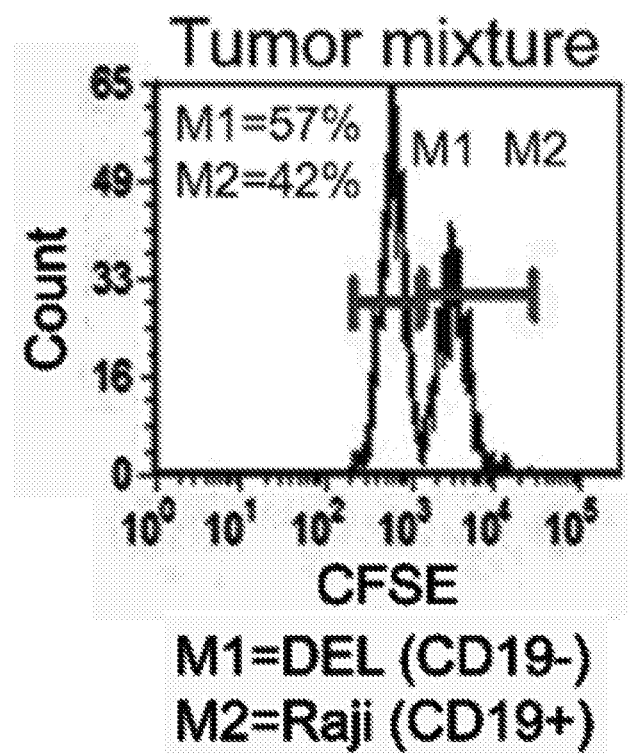

CD19 CAR T cells were produced as described (see Methods section). CD19 transduction of CAR T cells was verified by flow cytometry and ranged from 45-77%. Vector copy number ranged from 1.30-1.78 copies/cell. Initial cell killing experiments of CD19 CAR and Mock T cells utilized a tumor cell mixture of CD19-negative (DEL) and CD19-positive (Raji) cell lines. DEL and Raji cells were mixed at equivalent ratios and incubated with effector:target (E:T) ratios of 125:1, 25:1, 5:1 and 1:1 with either CD19 CAR or Mock T cells. Specific lysis was seen with CD19 CART cells but not Mock T cells for all E:T ratios. Thus, CD19 CAR T cells demonstrated antigen-specific killing of the CD19-positive cell line in an E:T dose dependent manner. Mock T cells did not kill either cell line (FIG. 4). Several other paired CD19-negative and CD19-positive cell lines (SUP-M2/RS-27, DEL/Granta-519, H929/RS-27) showed similar specific lysis (data not shown), thereby confirming the CD19 CAR T cell specificity and dose-dependence.

Figure 5:
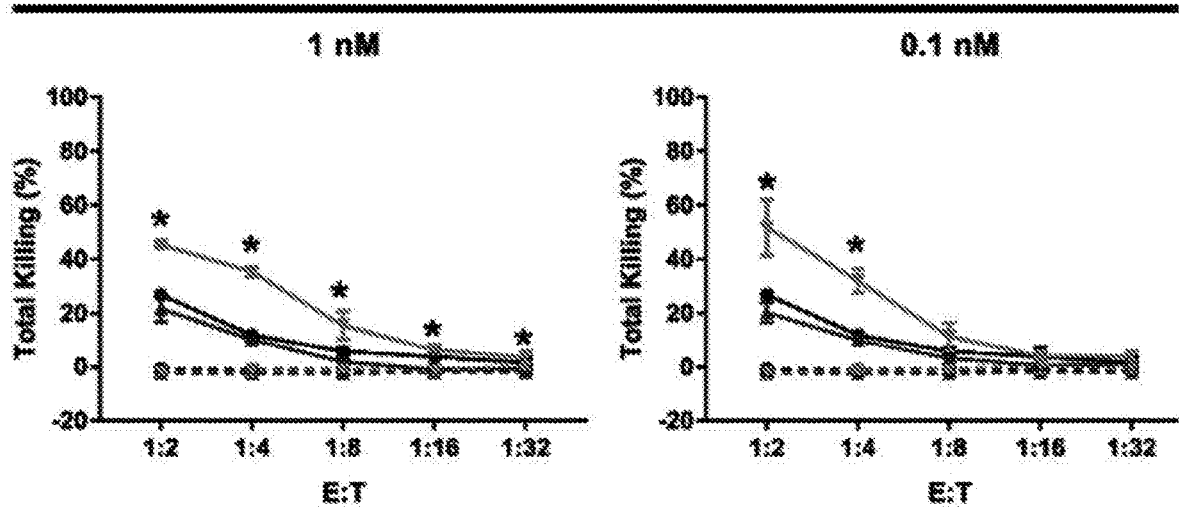
FIG. 5 shows that anti-CD20-hIFNα14 in combination with CD19 CAR T cells enhances cell killing compared to rituximab. Human lymphoma cell lines were pretreated with medium or with the indicated concentrations of rituximab or anti-CD20-hIFNα14 fusion protein for 18-24 hours. Cells were CFSE stained and plated in triplicate. Medium, rituximab or anti-CD20-hIFNα14 at the same pretreatment concentrations were added back to the appropriate wells and incubated for 30 minutes before CD19 CAR or Mock T cells were added at the designated E:T ratios and co-cultured for 24 hours. Cells were analyzed by flow cytometry and % total killing calculated. *$p<0.05$ when comparing rituximab and anti-CD20-hIFNα14 treated cell lines in combination with CD19 CAR T cells.
Figure 5:
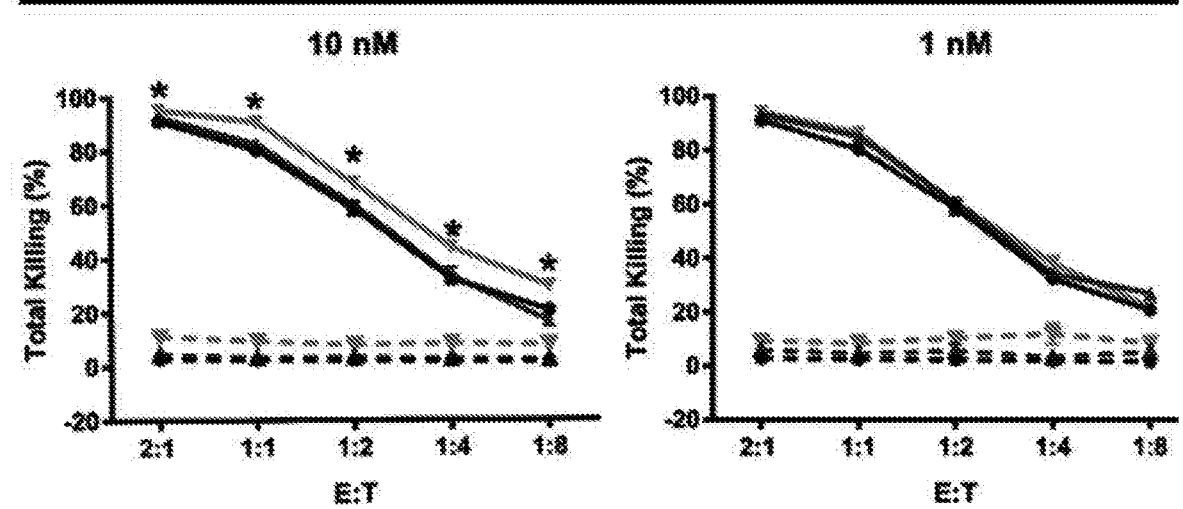

Anti-CD20-hIFNα14 Plus CAR T Cells Demonstrate Enhanced Cell Killing in Cytotoxicity Assays We next evaluated whether anti-CD20-hIFNα14 could enhance the cytotoxic effects of CD19 CART cells against the lymphoma cell line panel described above. Tumor cells were pretreated with medium alone (no treatment), anti-CD20-hIFNα14, or rituximab at equimolar concentrations for 18-24 hours and labeled with CFSE as described above. The CFSE-labeled tumor cells were then plated with medium, anti-CD20-hIFNα14, or rituximab at the equivalent pretreatment concentrations and CD19 CAR or Mock T cells added in varying E:T ratios and co-cultured for 24 hours. Combination of anti-CD20-hIFNα14 plus CD19 CAR T cells resulted in enhanced cell killing in the majority of the cell lines tested compared to rituximab or untreated cells (FIG. 5). Anti-CD20-hIFNα14 treated Daudi cells plus CD19 CAR T cells showed marked enhancement (nearly double) of cell killing at both 1 nM and 0.1 nM (p<0.05). The fusion protein treated combination group also showed significant total cell killing compared to rituximab or untreated cells in the OCI-Ly19 cell line, particularly at 10 nM treatment (p<0.05). At all E:T ratios, fusion protein pretreatment resulted in statistically significant increased total cell killing of the Granta-519 cell line at 1 nM and OCI-Ly2 at 10 nM (p<0.05). Pretreatment of the RS-27 cell line with anti-CD20-hIFNα14 at lower E:T ratios showed modest yet statistically significant increased cell killing with anti-CD20-hIFNα14 plus CAR T cells when compared to rituximab plus CAR T cells. The fusion protein pretreatment did not show significantly enhanced cell killing at any of the concentrations tested in Jeko-1. Higher concentrations of fusion protein did not necessarily lead to higher levels of cytotoxicity (for example Granta-519 at 10 nM). When tumor cells were treated with Mock T cells, only background levels of cell killing were noted. Overall, the addition of anti-CD20-hIFNα14 increased the tumor cell killing by effector CAR T cells even in these short-term overnight co-cultures.

Figure 6:
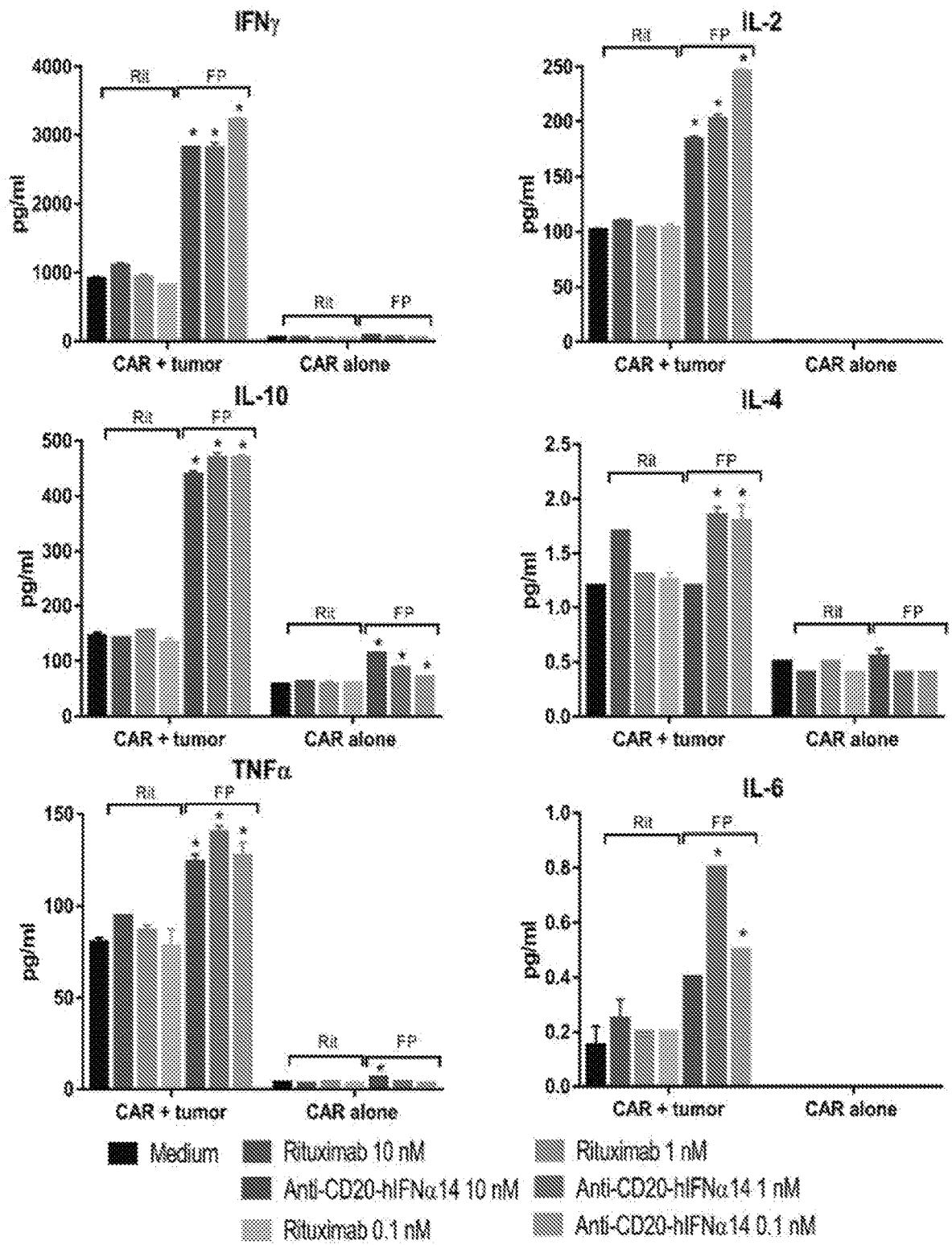
FIG. 6 shows that the combination of anti-CD20-hIFNα14 plus CD19 CAR T cells results in substantially increased cytokine production by effector T cells targeting OCI-Ly2 lymphoma cells. Supernatants from the 24 hour co-culture of the cell killing assay, as previously described, were collected and analyzed for IFNγ, IL-2, TNFα, IL-10, IL-4, and IL-6 by CIRAPLEX™ cytokine immunoassay kit. The tumor cells were treated at the indicated concentrations of rituximab or anti-CD20-hIFNα14 and CD19 CAR T cells added at an E:T ratio of 1:3. Recombinant cytokines were used to generate a standard curve and pg/mL concentrations graphed as mean±SD of duplicate samples. *p<0.05 when comparing rituximab and anti-CD20-hIFNα14 combination treatment. Rit=rituximab and FP=anti-CD20-hIFNα14.

Anti-CD20-hIFNα14 Treatment of Lymphoma Cells Causes Increased Cytokine Secretion by CD19 CAR T Cells To further explore the effects of anti-CD20-hIFNα14 on the response of CD19 CAR T cells to lymphoma cells, we evaluated the supernatants from the CAR and Mock tumor cell killing assays for cytokines including IFNγ, IL-2, TNFα, IL-10, IL-4, and IL-6. With the OCI-Ly2 cell line, despite only modest enhancement of cell killing by CAR T cells at 10 nM of anti-CD20-hIFNα14 and no enhancement at 1 nM and 0.1 nM (data not shown), there was a substantial increase in the release of cytokines compared to rituximab and no treatment, p<0.05 (FIG. 6). Overall, cytokine production did not appear to be dependent on the dose of anti-CD20-hIFNα14 and in some cases the lowest dose resulted in the largest enhancement of cytokine secretion. CD19 CAR T cells in the absence of tumor cells but with added rituximab or anti-CD20-hIFNα14 showed only background levels of cytokines. Mock T cells combined with anti-CD20-hIFNα14 showed only minimal increases in cytokine secretion (data not shown). Target lymphoma cells without the addition of T cells, but treated with rituximab or anti-CD20-hIFNα14 fusion protein secreted negligible amounts of cytokines (data not shown).

Figure 7:
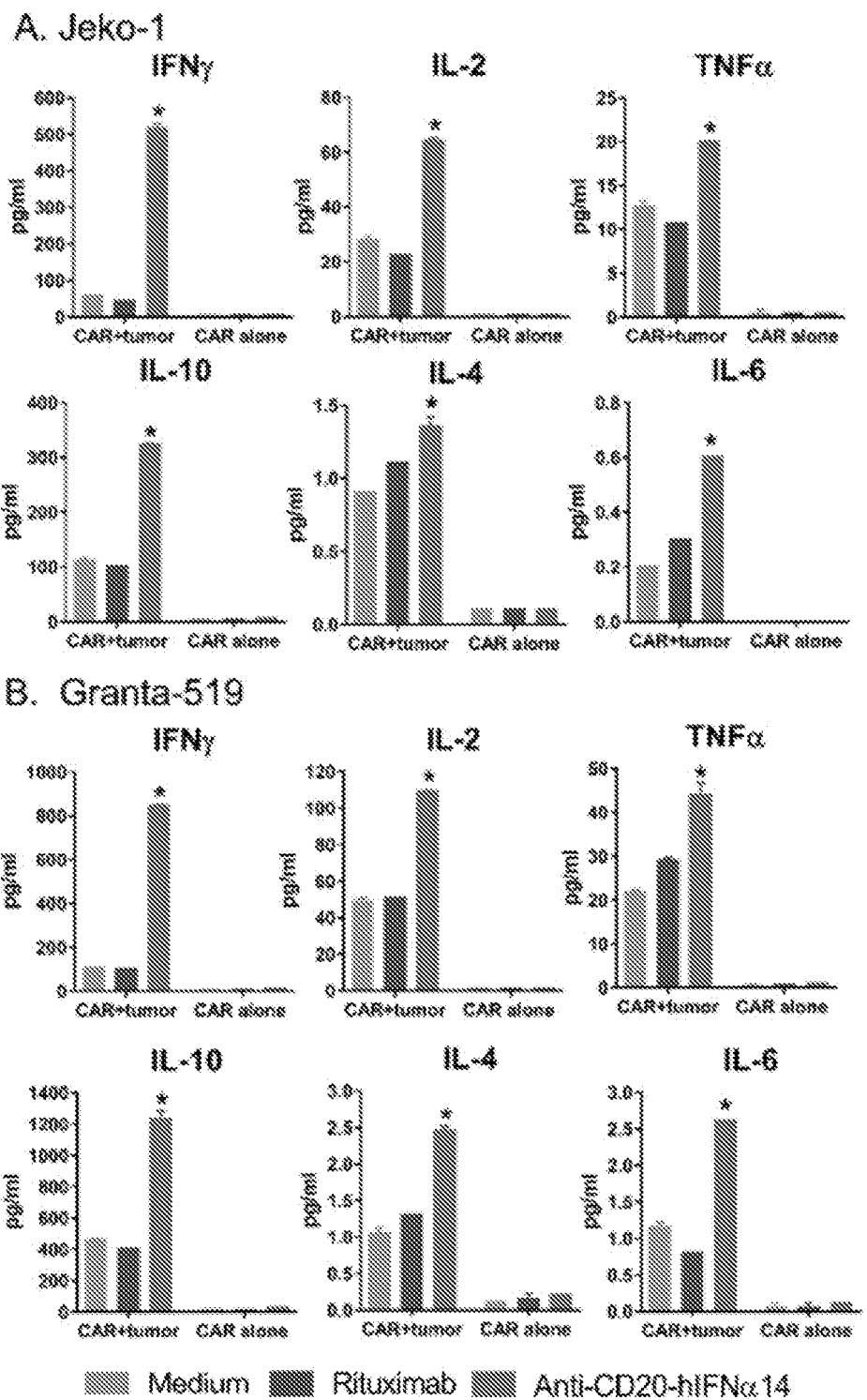
FIG. 7, panels A-E, shows that anti-CD20-hIFNα14-treated tumor cells in combination with CD19 CAR T cells elicit increased cytokine production compared to rituximab when targeting multiple B cell lymphomas. Assays were carried out as described in FIG. 6. Tumor cells were treated with medium or the indicated concentrations of rituximab or anti-CD20-hIFNα14: Panel A) Jeko-1 with 0.1 nM and E:T 1:1, Panel B) Granta-519 with 10 nM and E:T 2:1, Panel C) RS-27 with 0.1 nM and E:T 1:1, Panel D) Daudi with 0.1 nM and E:T 1:2, and Panel E) OCI-Ly19 with 1 nM and E:T 1:9. *p<0.05 when comparing rituximab and anti-CD20-hIFNα14 combination treatment.

Surprisingly, even amongst the cell lines that did not show enhanced killing, there was a significant increase in cytokine production by the CAR T cells when comparing anti-CD20-hIFNα14 treatment to rituximab or tumor alone. For all of the cell lines tested, anti-CD20-hIFNα14 plus CD19 CAR T cell combination therapy showed a significant increase in IFNγ, IL-2, and IL-10 production compared to rituximab or untreated cells. Among the fusion protein plus CAR T cell treated cell lines, 66% showed a significant increase in TNFα and 50% showed a significant increase in IL-4 and IL-6 (FIG. 7). Thus, anti-CD20-hIFNα14 uniformly increased cytokine release by CD19 CAR T cells, regardless of whether there was enhanced cell killing.

Figure 8:
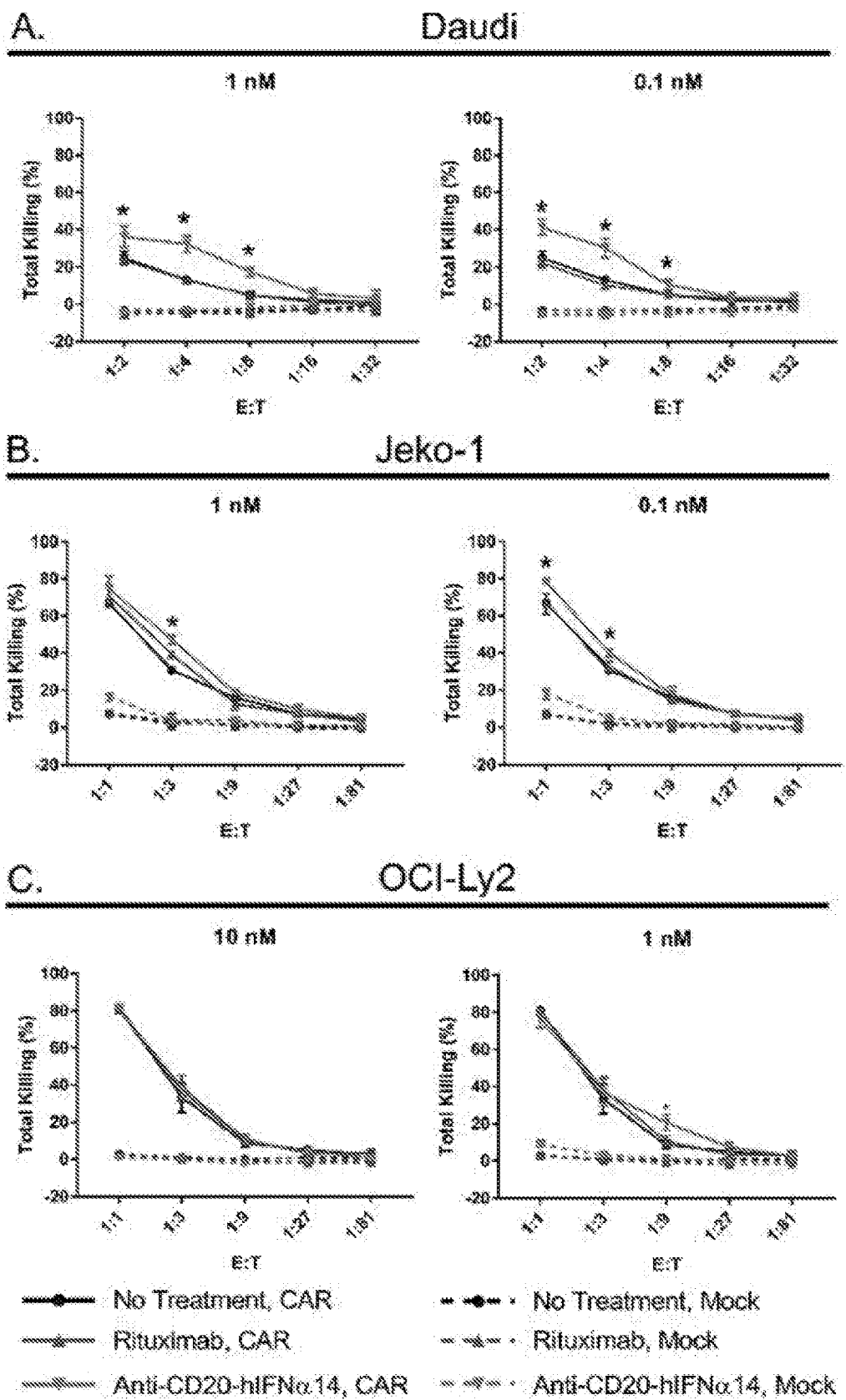
FIG. 8, panels A-F, shows that anti-CD20-hIFNα14 pretreatment only of lymphoma cells in combination with CD19 CAR T cells shows enhanced cell killing and increased cytokine production when compared to rituximab. Panels A-C) Assays were carried out as described in FIG. 5 with the exception that medium was added back to the wells instead of pretreatment concentrations of rituximab or anti-CD20-hIFNα14. Assays for cytokine production were carried out as described in FIG. 6 for panel D) Jeko-1 with 0.1 nM and E:T 1:1, panel E) OCI-Ly2 with 10 nM and E:T 1:1, and panel F) Daudi with 0.1 nM and E:T 1:2. *p<0.05 when comparing rituximab and anti-CD20-hIFNα14 combination treatment.

Limited Anti-CD20-hIFN014 Exposure Shows Enhanced CAR T Cell Killing and Increased Cytokine Production Similar to Prolonged Co-Culture In order to replicate in vivo conditions where anti-CD20-hIFNα14 targets to tumor cells and unbound fusion protein clears, we performed in vitro assays with anti-CD20-hIFNα14 pretreatment without adding anti-CD20-hIFNα14 back to the co-culture. Daudi, Jeko-1, and OCI-Ly2 tumor cells were treated with medium, anti-CD20-hIFNα14, or rituximab at the indicated concentrations for 18-24 hours and then co-cultured with CAR or Mock T cells as above without adding soluble fusion protein. Under these conditions effector CAR T cells would only be influenced by cell-bound fusion protein or antibody. Similar to the experiments in which soluble fusion protein was added to the co-culture, enhanced cell killing was seen with the anti-CD20-hIFNα14 plus CAR T cell combination (FIG. 8). Markedly increased cytokine production was also observed independent of the degree of cytotoxicity (FIG. 8).

Discussion

There is great unmet need for improving the ability of adoptively transferred T cells to infiltrate into cancers and then achieve optimal tumor-killing potency. Many patients' cancers resist infiltration by T cells, and in others the cells become inactivated or weakened upon reaching the tumor microenvironment. While CAR T cell therapy has been shown to be effective in several types of lymphomas and leukemias, most patients do not achieve durable remissions or cures with CAR T cell therapy alone (Abramson and others 2017; Neelapu and others 2017). Potential explanations for the unsustained responses may include loss of CD19 expression, CAR T cell exhaustion/target cell expression of PD-L1, lack of proliferation or survival, and poor trafficking of CAR T cells to the tumor site. Among the successive generations of CAR T cells, the first generation CAR T cells failed to induce adequate cytokine production and T cell expansion, resulting in suboptimal antitumor effects. The second generation CAR T cells, with the addition of a co-stimulatory molecule to the CD3ζ signaling domain, resulted in increased cytokine production and improved tumor regression (Kershaw and others 2013; Slaney and others 2014). Cytokine production appears to be necessary for optimal antitumor effects of CAR T cells. Thus by combining antibody-IFN fusion protein therapy with CAR T cells, therapeutic efficacy may be improved.

There are several strategies that have been proposed for boosting ACT in cancer, but none have the unique properties of antibody-IFN fusion proteins. Specifically, anti-CD20-hIFN fusion proteins and CD19 CAR T cells utilize a two-pronged attack against lymphoma cells with both CD19 and CD20 lymphoma-associated antigens being targeted. Antibody-IFN fusion proteins can localize to all sites of tumor in the body, thus permitting potentiation of ACT. By treating the patient with antibody-IFN fusion proteins, the IFN reaching the tumor sites can result in immunologic reactions that could be expected to weaken the tumor cells by inhibiting their growth, altering their expression of cell surface molecules thereby making them more recognizable to T cells (eg: adhesion, costimulation and HLA molecules), inducing local production of other cytokines and chemokines that promote T cell infiltration into tumors, and activating T cells that localize to the tumor site to attain more potent cytolytic functions.

We showed that pretreatment of lymphoma cells with anti-CD20-hIFNα14 can lead to sensitization for CAR T cell lysis and enhanced cytokine production. Interestingly and more biologically relevant, similar results were obtained when anti-CD20-hIFNα14 pretreated lymphoma cells (performed for Daudi, Jeko-1, and OCI-Ly2) were co-cultured with CAR T cells only without further addition of anti-CD20-hIFNα14. This indicates that tumor cell bound anti-CD20-hIFNα14 is responsible for enhancing CAR T cell effector functions. The observed enhanced tumor cell killing and increased cytokine production by CAR T cells, coupled with the known ability of IFNs to promote T cell infiltration and activation within tumors suggests that this combined approach may contribute to a significant improvement in CAR T cell efficacy (Zitvogel and others 2015).

With the combination of anti-CD20-hIFNα14 and CAR T cells we have found significant direct killing, but in a greater proportion of cell lines with differing histologies including Burkitt, GCB DLBCL, and MCL lines, we have found a substantial enhancement in cytokine release with the combination therapy. Cytokine release syndrome (CRS) is a well-documented side effect of CAR T cell therapy, characterized by secretion of large quantities of cytokines (including IL-6, TNFα, and IFNγ) and is associated with T cell activation (Davila and others 2014). The condition seems to correlate with tumor type and burden, genetic polymorphisms, and perhaps certain vector constructs (Lee and others 2014; Xu and Tang 2014). With CRS, there is infiltration and recruitment of T cells to the tumor bed. Whether this increase in cytokines correlates with efficacy remains unanswered. However, extrapolating from the acute lymphoblastic leukemia experience it appears that higher CRS grades are associated with greater CAR T cell expansion and persistence in responders (Mueller and others; Porter and others 2015). In patients where CRS is symptomatic, the condition can be addressed by supportive care, corticosteroids, and anti-IL-6 therapy, tocilizumab. We have shown a significant increase in cytokine release when tumor cells are pretreated with anti-CD20-hIFNα14 compared to when tumor cells are treated only with CAR T cells alone, which may correlate with enhanced T cell activation and efficacy in vivo.

We observed improvement in CAR T cell activity in direct killing and cytokine production in the presence of anti-CD20-hIFNα14. However, the limitations of these in vitro experiments include a brief co-culture of fusion protein, CAR T cells, and target cells, and thus may underestimate the effects of combination therapy. Even though this in vitro system does not represent the intact tumor microenvironment, we were still able to show enhanced direct killing of target cells and a clear escalation in cytokine release by CAR T cells with combination therapy. Even in the absence of enhanced cell killing there was increased cytokine production, thereby suggesting the potential for even greater cytotoxicity and activation of T cells. Future in vivo studies with antibody-targeted IFN therapy plus CD19 CAR T cells in syngeneic lymphoma/leukemia models are thus indicated in order to further explore the potential of this combination therapeutic approach. CAR T cells are at the forefront of cancer immunotherapy, but obtaining a high frequency of durable remissions and cures remains a challenge. These experiments highlight how antibody-targeted IFN can sensitize tumor cells for lysis and augment CAR T cell activation and cytokine production. Thus, combining antibody-targeted IFN with CAR T cells or other forms of ACT appears to be a promising new approach for treating patients with B cell lymphomas and other cancers.

REFERENCES

Abramson J S, Palomba M, Gordon L I, Lunning M A, Amason J E, Wang M, Forero A, Maloney D G, Albertson T, Garcia J, Li D, Xie B, Siddiqi T. 2017. High Durable C R Rates in Relapsed/Refractory (R/R) Aggressive B-NHL Treated with the CD19-Directed CAR T Cell Product JCAR017 (TRANSCEND NHL 001): Defined Composition Allows for Dose-Finding and Definition of Pivotal Cohort Andorsky D J, Yamada R E, Said J, Pinkus G S, Betting D J, Timmerman J M. 2011. Programmed Death Ligand 1 Is Expressed by Non-Hodgkin Lymphomas and Inhibits the Activity of Tumor-Associated T Cells. Clinical Cancer Research 17(13):4232-4244.

Anz D, Rapp M, Eiber S, Koelzer V H, Thaler R, Haubner S, Knott M, Nagel S, Golic M, Wiedemann G M, Bauernfeind F, Wurzenberger C, Hornung V, Scholz C, Mayr D, Rothenfusser S, Endres S, Bourquin C. 2015. Suppression of intratumoral CCL22 by type i interferon inhibits migration of regulatory T cells and blocks cancer progression. Cancer Res 75(21):4483-93.

Bacher N, Raker V, Hofmann C, Graulich E, Schwenk M, Baumgrass R, Bopp T, Zechner U, Merten L, Becker C, Steinbrink K. 2013. Interferon-alpha suppresses cAMP to disarm human regulatory T cells. Cancer Res 73(18):5647-56.

Borden E C, Lindner D, Dreicer R, Hussein M, Peereboom D. 2000. Second-generation interferons for cancer: clinical targets. Semin Cancer Biol 10(2):125-44.

Brentjens R J, Davila M L, Riviere I, Park J, Wang X, Cowell L G, Bartido S, Stefanski J, Taylor C, Olszewska M, Borquez-Ojeda O, Qu J, Wasielewska T, He Q, Bernal Y, Rijo I V, Hedvat C, Kobos R, Curran K, Steinherz P, Jurcic J, Rosenblat T, Maslak P, Frattini M, Sadelain M. 2013. CD19-targeted T cells rapidly induce molecular remissions in adults with chemotherapy-refractory acute lymphoblastic leukemia. Sci Transl Med 5(177):177ra38.

Challita P M, Skelton D, el-Khoueiry A, Yu X J, Weinberg K, Kohn D B. 1995. Multiple modifications in cis elements of the long terminal repeat of retroviral vectors lead to increased expression and decreased DNA methylation in embryonic carcinoma cells. *J Virol* 69(2):748-55.

Cooper A R, Patel S, Senadheera S, Plath K, Kohn D B, Hollis R P. 2011. Highly efficient large-scale lentiviral vector concentration by tandem tangential flow filtration. J Virol Methods 177(1):1-9.

Cooper L J, Topp M S, Serrano L M, Gonzalez S, Chang W C, Naranjo A, Wright C, Popplewell L, Raubitschek A, Forman S J, Jensen M C. 2003. T-cell clones can be rendered specific for CD19: toward the selective augmentation of the graft-versus-B-lineage leukemia effect. Blood 101(4):1637-44.

Crouse J, Bedenikovic G, Wiesel M, Ibberson M, Xenarios I, Von Laer D, Kalinke U, Vivier E, Jonjic S, Oxenius A. 2014. Type I interferons protect T cells against N K cell attack mediated by the activating receptor NCR1. Immunity 40(6):961-73.

Davila M L, Riviere I, Wang X, Bartido S, Park J, Curran K, Chung S S, Stefanski J, Borquez-Ojeda O, Olszewska M, Qu J, Wasielewska T, He Q, Fink M, Shinglot H, Youssif M, Satter M, Wang Y, Hosey J, Quintanilla H, Halton E, Bernal Y, Bouhassira D C, Arcila M E, Gonen M, Roboz G J, Maslak P, Douer D, Frattini M G, Giralt S, Sadelain M, Brentjens R. 2014. Efficacy and toxicity management of 19-28z CAR T cell therapy in B cell acute lymphoblastic leukemia. Sci Transl Med 6(224):224ra25.

De Oliveira S N, Ryan C, Giannoni F, Hardee C L, Tremcinska I, Katebian B, Wherley J, Sahaghian A, Tu A, Grogan T, Elashoff D, Cooper L J, Hollis R P, Kohn D B. 2013. Modification of hematopoietic stem/progenitor cells with CD19-specific chimeric antigen receptors as a novel approach for cancer immunotherapy. Hum Gene Ther 24(10):824-839.

Dull T, Zufferey R, Kelly M, Mandel R J, Nguyen M, Trono D, Naldim L. 1998. A third-generation lentivirus vector with a conditional packaging system. J Virol 72(11):8463-8471.

Hamilton R G, Morrison S L. 1993. Epitope mapping of human immunoglobulin-specific murine monoclonal antibodies with domain-switched, deleted and point-mutated chimeric antibodies. *J Immunol Methods* 158 (1):107-122.

Kershaw et al. (2013) *Nat. Rev Cancer.* 13(8): 525-541.

Kochenderfer J N, Dudley M E, Kassim S H, Somerville R P, Carpenter R O, Stetler-Stevenson M, Yang J C, Phan G Q, Hughes M S, Sherry R M, Raffeld M, Feldman S, Lu L, Li Y F, Ngo L T, Goy A, Feldman T, Spaner D E, Wang M L, Chen C C, Kranick S M, Nath A, Nathan D A, Morton K E, Toomey M A, Rosenberg S A. 2015. Chemotherapy-refractory diffuse large B-cell lymphoma and indolent B-cell malignancies can be effectively treated with autologous T cells expressing an anti-CD19 chimeric antigen receptor. J Clin Oncol 33(6):540-9.

Kowolik C M, Topp M S, Gonzalez S, Pfeiffer T, Olivares S, Gonzalez N, Smith D D, Forman S J, Jensen M C, Cooper U. 2006. CD28 costimulation provided through a CD19-specific chimeric antigen receptor enhances in vivo persistence and antitumor efficacy of adoptively transferred T cells. *Cancer Res* 66(22):10995-1004.

Larson S M, Truscott L C, Chiou T T, Patel A, Kao R, Tu A, Tyagi T, Lu X, Elashoff D, De Oliveira S N. 2017. Pre-clinical development of gene modification of haematopoietic stem cells with chimeric antigen receptors for cancer immunotherapy. Hum Vaccin Immunother 13(5):1094-1104.

Lavoie T B, Kalie E, Crisafulli-Cabatu S, Abramovich R, DiGioia G, Moolchan K, Pestka S, Schreiber G. 2011. Binding and activity of all human alpha interferon subtypes. Cytokine 56(2):282-9.

Lee D W, Gardner R, Porter D L, Louis C U, Ahmed N, Jensen M, Grupp S A, Mackall C L. 2014. Current concepts in the diagnosis and management of cytokine release syndrome. Blood 124(2):188-95.

Mueller K T, Waldron E, Grupp S A, Levine J, Laetsch T W, Pulsipher M A, Boyer M, August K, Hamilton J, Awasthi R, Sickert D, Chakraborty A, Levine B L, June C H, Tomassian L, Leung M, Taran T, Wood P, Maude S. CTL019 Clinical Pharmacology and Biopharmaceutics in Pediatric Patients with Relapsed or Refractory (R/R) Acute Lymphoblastic Leukemia (ALL). Clinical Lymphoma, Myeloma and Leukemia 17:S261-S262.

Neelapu S S, Locke F L, Bartlett N L, Lekakis L J, Miklos D B, Jacobson C A, Braunschweig I, Oluwole O O, Siddiqi T, Lin Y, Timmerman J M, Stiff P J, Friedberg J W, Flinn I W, Goy A, Hill B T, Smith M R, Deol A, Farooq U, McSweeney P, Munoz J, Avivi I, Castro J E, Westin J R, Chavez J C, Ghobadi A, Komanduri K V, Levy R, Jacobsen E D, Witzig T E, Reagan P, Bot A, Rossi J, Navale L, Jiang Y, Aycock J, Elias M, Chang D, Wiezorek J, Go W Y. 2017. Axicabtagene Ciloleucel CAR T-Cell Therapy in Refractory Large B-Cell Lymphoma. New England Journal of Medicine 0(0):null.

Papewalis C, Jacobs B, Wuttke M, Ullrich E, Baehring T, Fenk R, Willenberg H S, Schinner S, Cohnen M, Seissler J, Zacharowski K, Scherbaum W A, Schott M. 2008. IFN-alpha skews monocytes into CD56+-expressing dendritic cells with potent functional activities in vitro and in vivo. J Immunol 180(3):1462-70.

Parker B S, Rautela J, Hertzog P J. 2016. Antitumour actions of interferons: implications for cancer therapy. *Nat Rev Cancer* 16(3):131-44.

Porter D L, Hwang W T, Frey N V, Lacey S F, Shaw P A, Loren A W, Bagg A, Marcucci K T, Shen A, Gonzalez V, Ambrose D, Grupp S A, Chew A, Zheng Z, Milone M C, Levine B L, Melenhorst J J, June C H. 2015. Chimeric antigen receptor T cells persist and induce sustained remissions in relapsed refractory chronic lymphocytic leukemia. Sci Transl Med 7(303): 303ra139.

Schuster S J, Bishop M R, Tam C, Waller E K, Borchmann P, McGuirk J, Jager U, Jaglowski S, Andreadis C, Westin H J, Fleury I, Bachanova V, Foley S R, Ho P J, Mielke S, Holte H, Anak O, Pacaud L, Awasthi R, Tai F, Salles G, Maziarz R. 2017. GLOBAL PIVOTAL PHASE 2 TRIAL OF THE CD19-TARGETED THERAPY CTL019 IN ADULT PATIENTS WITH RELAPSED OR REFRACTORY (R/R) DIFFUSE LARGE B-CELL LYMPHOMA (DLBCL)—AN INTERIM ANALYSIS. Hematological Oncology 35:27-27.

Slaney C Y, Kershaw M H, Darcy P K. 2014. Trafficking of T cells into tumors. Cancer Res 74(24):7168-74.

Trinh K R, Vasuthasawat A, Steward K K, Yamada R E, Timmerman J M, Morrison S L. 2013. Anti-CD20-interferon-beta fusion protein therapy of murine B-cell lymphomas. J Immunother 36(5):305-18.

Turtle C J, Hanafi L A, Berger C, Hudecek M, Pender B, Robinson E, Hawkins R, Chaney C, Cherian S, Chen X, Soma L, Wood B, Li D, Heimfeld S, Riddell S R, Maloney D G. 2016. Immunotherapy of non-Hodgkin's lymphoma with a defined ratio of CD8+ and CD4+ CD19-specific chimeric antigen receptor-modified T cells. Sci Transl Med 8(355):355ra116.

Xu H C, Grusdat M, Pandyra A A, Polz R, Huang J, Sharma P, Deenen R, Kohrer K, Rahbar R, Diefenbach A, Gibbert K, Lohning M, Hocker L, Waibler Z, Haussinger D, Mak T W, Ohashi P S, Lang K S, Lang P A. 2014. Type I interferon protects antiviral CD8+ T cells from NK cell cytotoxicity. Immunity 40(6):949-60.

Xu X J, Tang Y M. 2014. Cytokine release syndrome in cancer immunotherapy with chimeric antigen receptor engineered T cells. Cancer Lett 343(2):172-8.

Xuan C, Steward K K, Timmerman J M, Morrison S L. 2010. Targeted delivery of interferon-alpha via fusion to anti-CD20 results in potent antitumor activity against B-cell lymphoma. Blood 115(14):2864-71.

Yoo E M, Trinh K R, Tran D, Vasuthasawat A, Zhang J, Hoang B, Lichtenstein A, Morrison S L. 2015. Anti-CD138-Targeted Interferon Is a Potent Therapeutic Against Multiple Myeloma. Journal of Interferon and Cytokine Research 35(4):281-291.

Young P A, Dang N H, Nastoupil L, Minning D, Gresser M J, Timmerman J M. 2016. Antibody-interferon-alpha fusion protein (IGN002) for the treatment of b-cell non-Hodgkin lymphomas: A phase 1, first-in-human, dose-escalation trial. J Clin Oncol 34, 2016 (suppl; abstr TPS3109).

Young P A, Morrison S L, Timmerman J M. 2014. Antibody-cytokine fusion proteins for treatment of cancer: engineering cytokines for improved efficacy and safety. Semin Oncol 41(5):623-36.

Zitvogel L, Galluzzi L, Kepp O, Smyth M J, Kroemer G. 2015. Type I interferons in anticancer immunity. Nat Rev Immunol 15(7):405-14.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING

<160> NUMBER OF SEQ ID NOS: 78

<210> SEQ ID NO 1
<211> LENGTH: 6
<212> TYPE: PRT
<213> ORGANISM: Artificial
<220> FEATURE:
<223> OTHER INFORMATION: Peptide linker

<400> SEQUENCE: 1

Ser Gly Gly Gly Gly Ser
1               5

<210> SEQ ID NO 2
<211> LENGTH: 15
<212> TYPE: PRT
<213> ORGANISM: Artificial
<220> FEATURE:
<223> OTHER INFORMATION: Peptide linker

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 12
<212> TYPE: PRT
<213> ORGANISM: Artificial
<220> FEATURE:
<223> OTHER INFORMATION: Peptide linker

<400> SEQUENCE: 3

Ala Glu Ala Ala Ala Lys Glu Ala Ala Ala Lys Ala
1               5                   10

<210> SEQ ID NO 4
<211> LENGTH: 184
<212> TYPE: PRT
<213> ORGANISM: Artificial
<220> FEATURE:
<223> OTHER INFORMATION: Peptide linker

<400> SEQUENCE: 4

Met Gly Lys Met Ala Ser Leu Phe Ala Thr Phe Leu Val Val Leu Val
1               5                   10                  15

Ser Leu Ser Leu Ala Ser Glu Ser Ser Ala Cys Asp Leu Pro Gln Thr
                20                  25                  30

His Ser Leu Gly Ser Arg Arg Thr Leu Met Leu Leu Ala Gln Met Arg
            35                  40                  45

Arg Ile Ser Leu Phe Ser Cys Leu Lys Asp Arg His Asp Phe Gly Phe
        50                  55                  60

Pro Gln Glu Glu Phe Gly Asn Gln Phe Gln Lys Ala Glu Thr Ile Pro
65                  70                  75                  80

Val Leu His Glu Met Ile Gln Gln Ile Phe Asn Leu Phe Ser Thr Lys
                85                  90                  95

Asp Ser Ser Ala Ala Trp Asp Glu Thr Leu Leu Asp Lys Phe Tyr Thr
                100                 105                 110

Glu Leu Tyr Gln Gln Leu Asn Asp Leu Glu Ala Cys Val Ile Gln Gly
            115                 120                 125

Val Gly Val Thr Glu Thr Pro Leu Met Lys Glu Asp Ser Ile Leu Ala
        130                 135                 140

Val Arg Lys Tyr Phe Gln Arg Ile Thr Leu Tyr Leu Lys Glu Lys Lys

```
145                 150                 155                 160

Tyr Ser Pro Cys Ala Trp Glu Val Val Arg Ala Glu Ile Met Arg Ser
                165                 170                 175

Phe Ser Leu Ser Thr Asn Leu Gln
            180

<210> SEQ ID NO 5
<211> LENGTH: 183
<212> TYPE: PRT
<213> ORGANISM: Artificial
<220> FEATURE:
<223> OTHER INFORMATION: Peptide linker

<400> SEQUENCE: 5

Met Gly Lys Met Ala Ser Leu Phe Ala Thr Phe Leu Val Val Leu Val
1               5                   10                  15

Ser Leu Ser Leu Ala Ser Glu Ser Ser Ala Cys Asp Leu Pro Gln Thr
            20                  25                  30

His Ser Leu Gly Ser Arg Arg Thr Leu Met Leu Leu Ala Gln Met Arg
        35                  40                  45

Arg Ile Ser Leu Phe Ser Cys Leu Lys Asp Arg His Asp Phe Gly Phe
    50                  55                  60

Pro Gln Glu Glu Phe Gly Asn Gln Phe Gln Lys Ala Glu Thr Ile Pro
65                  70                  75                  80

Val Leu His Glu Met Ile Gln Gln Ile Phe Asn Leu Phe Ser Thr Lys
                85                  90                  95

Asp Ser Ser Ala Ala Trp Asp Glu Thr Leu Leu Asp Lys Phe Tyr Thr
            100                 105                 110

Glu Leu Tyr Gln Gln Leu Asn Asp Leu Glu Ala Cys Val Ile Gln Gly
        115                 120                 125

Val Gly Val Thr Glu Thr Pro Leu Met Lys Glu Asp Ser Ile Leu Ala
    130                 135                 140

Val Arg Lys Tyr Phe Gln Arg Ile Thr Leu Tyr Leu Lys Glu Lys Lys
145                 150                 155                 160

Tyr Ser Pro Cys Ala Trp Glu Val Val Arg Ala Glu Ile Met Arg Ser
                165                 170                 175

Phe Ser Leu Ser Thr Asn Leu
            180

<210> SEQ ID NO 6
<211> LENGTH: 182
<212> TYPE: PRT
<213> ORGANISM: Artificial
<220> FEATURE:
<223> OTHER INFORMATION: Peptide linker

<400> SEQUENCE: 6

Met Gly Lys Met Ala Ser Leu Phe Ala Thr Phe Leu Val Val Leu Val
1               5                   10                  15

Ser Leu Ser Leu Ala Ser Glu Ser Ser Ala Cys Asp Leu Pro Gln Thr
            20                  25                  30

His Ser Leu Gly Ser Arg Arg Thr Leu Met Leu Leu Ala Gln Met Arg
        35                  40                  45

Arg Ile Ser Leu Phe Ser Cys Leu Lys Asp Arg His Asp Phe Gly Phe
    50                  55                  60

Pro Gln Glu Glu Phe Gly Asn Gln Phe Gln Lys Ala Glu Thr Ile Pro
65                  70                  75                  80
```

```
Val Leu His Glu Met Ile Gln Gln Ile Phe Asn Leu Phe Ser Thr Lys
                85                  90                  95

Asp Ser Ser Ala Ala Trp Asp Glu Thr Leu Leu Asp Lys Phe Tyr Thr
            100                 105                 110

Glu Leu Tyr Gln Gln Leu Asn Asp Leu Glu Ala Cys Val Ile Gln Gly
        115                 120                 125

Val Gly Val Thr Glu Thr Pro Leu Met Lys Glu Asp Ser Ile Leu Ala
    130                 135                 140

Val Arg Lys Tyr Phe Gln Arg Ile Thr Leu Tyr Leu Lys Glu Lys Lys
145                 150                 155                 160

Tyr Ser Pro Cys Ala Trp Glu Val Val Arg Ala Glu Ile Met Arg Ser
                165                 170                 175

Phe Ser Leu Ser Thr Asn
            180

<210> SEQ ID NO 7
<211> LENGTH: 165
<212> TYPE: PRT
<213> ORGANISM: Artificial
<220> FEATURE:
<223> OTHER INFORMATION: Mutant interferon

<400> SEQUENCE: 7

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 8
<211> LENGTH: 165
<212> TYPE: PRT
<213> ORGANISM: Artificial
<220> FEATURE:
<223> OTHER INFORMATION: Mutant interferon

<400> SEQUENCE: 8

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30
```

```
Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
 50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 9
<211> LENGTH: 166
<212> TYPE: PRT
<213> ORGANISM: Artificial
<220> FEATURE:
<223> OTHER INFORMATION: Mutant interferon

<400> SEQUENCE: 9

Cys Asp Leu Pro Gln Thr His Ser Leu Gly Asn Arg Arg Ala Leu Ile
 1               5                  10                  15

Leu Leu Gly Gln Met Gly Arg Ile Ser Pro Phe Ser Cys Leu Lys Asp
                20                  25                  30

Arg His Asp Phe Arg Ile Pro Gln Glu Glu Phe Asp Gly Asn Gln Phe
            35                  40                  45

Gln Lys Ala Gln Ala Ile Ser Val Leu His Glu Met Ile Gln Gln Thr
 50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
                100                 105                 110

Asn Glu Asp Ser Ile Leu Ala Val Arg Lys Tyr Phe Gln Arg Ile Thr
            115                 120                 125

Leu Tyr Leu Ile Glu Arg Lys Tyr Ser Pro Cys Ala Trp Glu Val Val
                130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 10
<211> LENGTH: 165
<212> TYPE: PRT
<213> ORGANISM: Artificial
<220> FEATURE:
<223> OTHER INFORMATION: Mutant interferon
```

```
<400> SEQUENCE: 10

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg Arg Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 11
<211> LENGTH: 166
<212> TYPE: PRT
<213> ORGANISM: Artificial
<220> FEATURE:
<223> OTHER INFORMATION: Mutant interferon

<400> SEQUENCE: 11

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
130                 135                 140

Arg Ala Glu Ile Met Arg Ser Leu Ser Leu Ser Thr Asn Leu Gln Glu
145                 150                 155                 160

Arg Leu Arg Arg Lys Glu
                165
```

<210> SEQ ID NO 12
<211> LENGTH: 166
<212> TYPE: PRT
<213> ORGANISM: Homo sapiens

<400> SEQUENCE: 12

Cys Asp Leu Pro Gln Thr His Ser Leu Ser Asn Arg Arg Thr Leu Met
1               5                   10                  15

Ile Met Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Met Met Gln Glu Val Gly Val Glu Asp Thr Pro Leu Met
            100                 105                 110

Asn Val Asp Ser Ile Leu Thr Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Ala Asn Leu Gln Glu
145                 150                 155                 160

Arg Leu Arg Arg Lys Glu
                165

<210> SEQ ID NO 13
<211> LENGTH: 166
<212> TYPE: PRT
<213> ORGANISM: Homo sapiens

<400> SEQUENCE: 13

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn Gln Phe
        35                  40                  45

Gln Lys Ala Glu Ala Ile Ser Val Leu His Glu Val Ile Gln Gln Thr
    50                  55                  60

Phe Asn Leu Phe Ser Thr Lys Asp Ser Ser Val Ala Trp Asp Glu Arg
65                  70                  75                  80

Leu Leu Asp Lys Leu Tyr Thr Glu Leu Tyr Gln Gln Leu Asn Asp Leu
                85                  90                  95

Glu Ala Cys Val Met Gln Glu Val Trp Val Gly Gly Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Ser Ser Arg Asn Leu Gln Glu
145                 150                 155                 160

Arg Leu Arg Arg Lys Glu

-continued

```
                165
```

<210> SEQ ID NO 14
<211> LENGTH: 166
<212> TYPE: PRT
<213> ORGANISM: Homo sapiens

<400> SEQUENCE: 14

```
Cys Asp Leu Pro Gln Thr His Ser Leu Gly Asn Arg Arg Ala Leu Ile
1               5                   10                  15

Leu Leu Ala Gln Met Gly Arg Ile Ser His Phe Ser Cys Leu Lys Asp
            20                  25                  30

Arg His Asp Phe Gly Phe Pro Glu Glu Glu Phe Asp Gly His Gln Phe
        35                  40                  45

Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165
```

<210> SEQ ID NO 15
<211> LENGTH: 166
<212> TYPE: PRT
<213> ORGANISM: Homo sapiens

<400> SEQUENCE: 15

```
Cys Asp Leu Pro Gln Thr His Ser Leu Gly Asn Arg Arg Ala Leu Ile
1               5                   10                  15

Leu Leu Ala Gln Met Gly Arg Ile Ser His Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
```

```
145                 150                 155                 160
Arg Leu Arg Arg Lys Asp
                165
```

<210> SEQ ID NO 16
<211> LENGTH: 166
<212> TYPE: PRT
<213> ORGANISM: Homo sapiens

<400> SEQUENCE: 16

```
Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Leu Pro Gln Glu Glu Phe Asp Gly Asn Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asn Leu
                85                  90                  95

Glu Ala Cys Val Ile Gln Glu Val Gly Met Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Ile Leu Arg Arg Lys Asp
                165
```

<210> SEQ ID NO 17
<211> LENGTH: 166
<212> TYPE: PRT
<213> ORGANISM: Homo sapiens

<400> SEQUENCE: 17

```
Cys Asp Leu Pro Gln Thr His Ser Leu Arg Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Glu Phe Arg Phe Pro Glu Glu Glu Phe Asp Gly His Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Phe Ile Leu Ala Val Arg Lys Tyr Phe Gln Arg Ile Thr
        115                 120                 125

Leu Tyr Leu Met Glu Lys Lys Tyr Ser Pro Cys Ala Trp Glu Val Val
```

```
                130             135             140
Arg Ala Glu Ile Met Arg Ser Phe Ser Phe Ser Thr Asn Leu Lys Lys
145                 150                 155                 160

Gly Leu Arg Arg Lys Asp
                165

<210> SEQ ID NO 18
<211> LENGTH: 166
<212> TYPE: PRT
<213> ORGANISM: Homo sapiens

<400> SEQUENCE: 18

Cys Asn Leu Ser Gln Thr His Ser Leu Asn Asn Arg Arg Thr Leu Met
1               5                   10                  15

Leu Met Ala Gln Met Arg Arg Ile Ser Pro Phe Ser Cys Leu Lys Asp
                20                  25                  30

Arg His Asp Phe Glu Phe Pro Gln Glu Glu Phe Asp Gly Asn Gln Phe
                35                  40                  45

Gln Lys Ala Gln Ala Ile Ser Val Leu His Glu Met Met Gln Gln Thr
            50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Lys Lys Tyr Phe Gln Arg Ile Thr
        115                 120                 125

Leu Tyr Leu Met Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 19
<211> LENGTH: 166
<212> TYPE: PRT
<213> ORGANISM: Homo sapiens

<400> SEQUENCE: 19

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
                20                  25                  30

Arg His Asp Phe Gly Phe Pro Gln Glu Glu Phe Asp Gly Asn Gln Phe
                35                  40                  45

Gln Lys Ala Gln Ala Ile Ser Val Leu His Glu Met Ile Gln Gln Thr
            50                  55                  60

Phe Asn Leu Phe Ser Thr Lys Asp Ser Ser Ala Thr Trp Glu Gln Ser
65                  70                  75                  80

Leu Leu Glu Lys Phe Ser Thr Glu Leu Asn Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Lys Lys Tyr Phe Gln Arg Ile Thr
```

```
                115                 120                 125
Leu Tyr Leu Thr Glu Lys Lys Tyr Ser Pro Cys Ala Trp Glu Val Val
    130                 135                 140
Arg Ala Glu Ile Met Arg Ser Phe Ser Leu Ser Lys Ile Phe Gln Glu
145                 150                 155                 160
Arg Leu Arg Arg Lys Glu
                165

<210> SEQ ID NO 20
<211> LENGTH: 166
<212> TYPE: PRT
<213> ORGANISM: Homo sapiens

<400> SEQUENCE: 20

Cys Asp Leu Pro Gln Thr His Ser Leu Gly Asn Arg Arg Ala Leu Ile
1               5                   10                  15
Leu Leu Ala Gln Met Arg Arg Ile Ser Pro Phe Ser Cys Leu Lys Asp
                20                  25                  30
Arg His Asp Phe Glu Phe Pro Gln Glu Glu Phe Asp Asp Lys Gln Phe
            35                  40                  45
Gln Lys Ala Gln Ala Ile Ser Val Leu His Glu Met Ile Gln Gln Thr
    50                  55                  60
Phe Asn Leu Phe Ser Thr Lys Asp Ser Ser Ala Ala Leu Asp Glu Thr
65                  70                  75                  80
Leu Leu Asp Glu Phe Tyr Ile Glu Leu Asp Gln Gln Leu Asn Asp Leu
                85                  90                  95
Glu Ser Cys Val Met Gln Glu Val Gly Val Ile Glu Ser Pro Leu Met
            100                 105                 110
Tyr Glu Asp Ser Ile Leu Ala Val Arg Lys Tyr Phe Gln Arg Ile Thr
        115                 120                 125
Leu Tyr Leu Thr Glu Lys Lys Tyr Ser Ser Cys Ala Trp Glu Val Val
    130                 135                 140
Arg Ala Glu Ile Met Arg Ser Phe Ser Leu Ser Ile Asn Leu Gln Lys
145                 150                 155                 160
Arg Leu Lys Ser Lys Glu
                165

<210> SEQ ID NO 21
<211> LENGTH: 165
<212> TYPE: PRT
<213> ORGANISM: Homo sapiens

<400> SEQUENCE: 21

Cys Asp Leu Pro Gln Thr His Ser Leu Gly Asn Arg Arg Ala Leu Ile
1               5                   10                  15
Leu Leu Ala Gln Met Arg Arg Ile Ser Pro Phe Ser Cys Leu Lys Asp
                20                  25                  30
Arg His Asp Phe Gly Pro Gln Glu Glu Phe Asp Gly Asn Gln Phe Gln
            35                  40                  45
Lys Ala Gln Ala Ile Ser Val Leu His Glu Met Ile Gln Gln Thr Phe
    50                  55                  60
Asn Leu Phe Ser Thr Lys Asp Ser Ser Ala Ala Trp Asp Glu Ser Leu
65                  70                  75                  80
Leu Glu Lys Phe Tyr Thr Glu Leu Tyr Gln Gln Leu Asn Asp Leu Glu
                85                  90                  95
Ala Cys Val Ile Gln Glu Val Gly Val Glu Glu Thr Pro Leu Met Asn
```

```
            100                 105                 110
Val Asp Ser Ile Leu Ala Val Lys Lys Tyr Phe Gln Arg Ile Thr Leu
            115                 120                 125

Tyr Leu Thr Glu Lys Lys Tyr Ser Pro Cys Ala Trp Glu Val Val Arg
        130                 135                 140

Ala Glu Ile Met Arg Ser Phe Ser Leu Ser Thr Asn Leu Gln Glu Arg
145                 150                 155                 160

Leu Arg Arg Lys Glu
                165

<210> SEQ ID NO 22
<211> LENGTH: 166
<212> TYPE: PRT
<213> ORGANISM: Homo sapiens

<400> SEQUENCE: 22

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 23
<211> LENGTH: 142
<212> TYPE: PRT
<213> ORGANISM: Homo sapiens

<400> SEQUENCE: 23

Asp Pro Tyr Val Lys Glu Ala Glu Asn Leu Lys Lys Tyr Phe Asn Ala
1               5                   10                  15

Gly His Ser Asp Val Ala Asp Asn Gly Thr Leu Phe Leu Gly Ile Leu
            20                  25                  30

Lys Asn Trp Lys Glu Glu Ser Asp Arg Lys Ile Met Gln Ser Gln Ile
        35                  40                  45

Val Ser Phe Tyr Phe Lys Leu Phe Lys Asn Phe Lys Asp Asp Gln Ser
    50                  55                  60

Ile Gln Lys Ser Val Glu Thr Ile Lys Glu Asp Met Asn Val Lys Phe
65                  70                  75                  80

Phe Asn Ser Asn Lys Lys Lys Arg Asp Asp Phe Glu Lys Leu Thr Asn
```

85                  90                  95

Tyr Ser Val Thr Asp Leu Asn Val Gln Arg Lys Ala Ile His Glu Leu
                100                 105                 110

Ile Gln Val Met Ala Glu Leu Ser Pro Ala Ala Lys Thr Gly Lys Arg
            115                 120                 125

Lys Arg Ser Gln Met Leu Phe Gln Gly Arg Arg Ala Ser Gln
        130                 135                 140

<210> SEQ ID NO 24
<211> LENGTH: 133
<212> TYPE: PRT
<213> ORGANISM: Homo sapiens

<400> SEQUENCE: 24

Asp Pro Tyr Val Lys Glu Ala Glu Asn Leu Lys Lys Tyr Phe Asn Ala
1               5                   10                  15

Gly His Ser Asp Val Ala Asp Asn Gly Thr Leu Phe Leu Gly Ile Leu
            20                  25                  30

Lys Asn Trp Lys Glu Glu Ser Asp Arg Lys Ile Met Gln Ser Gln Ile
        35                  40                  45

Val Ser Phe Tyr Phe Lys Leu Phe Lys Asn Phe Lys Asp Asp Gln Ser
    50                  55                  60

Ile Gln Lys Ser Val Glu Thr Ile Lys Glu Asp Met Asn Val Lys Phe
65                  70                  75                  80

Phe Asn Ser Asn Lys Lys Lys Arg Asp Asp Phe Glu Lys Leu Thr Asn
                85                  90                  95

Tyr Ser Val Thr Asp Leu Asn Val Gln Arg Lys Ala Ile His Glu Leu
                100                 105                 110

Ile Gln Val Met Ala Glu Leu Ser Pro Ala Ala Lys Thr Gly Lys Arg
            115                 120                 125

Lys Arg Ser Gln Met
        130

<210> SEQ ID NO 25
<211> LENGTH: 15
<212> TYPE: PRT
<213> ORGANISM: Artificial
<220> FEATURE:
<223> OTHER INFORMATION: Peptide linker

<400> SEQUENCE: 25

Gly Gly Gly Gly Ser Gly Gly Gly Ser Gly Gly Gly Gly Ser
1               5                   10                  15

<210> SEQ ID NO 26
<211> LENGTH: 5
<212> TYPE: PRT
<213> ORGANISM: Artificial
<220> FEATURE:
<223> OTHER INFORMATION: Peptide linker

<400> SEQUENCE: 26

Gly Gly Gly Gly Ser
1               5

<210> SEQ ID NO 27
<211> LENGTH: 6
<212> TYPE: PRT
<213> ORGANISM: Artificial
<220> FEATURE:
<223> OTHER INFORMATION: Peptide linker

```
<400> SEQUENCE: 27

Ser Gly Gly Gly Gly Ser
1               5

<210> SEQ ID NO 28
<211> LENGTH: 10
<212> TYPE: PRT
<213> ORGANISM: Artificial
<220> FEATURE:
<223> OTHER INFORMATION: Peptide linker

<400> SEQUENCE: 28

Gly Gly Gly Gly Ser Gly Gly Gly Gly Ser
1               5                   10

<210> SEQ ID NO 29
<211> LENGTH: 7
<212> TYPE: PRT
<213> ORGANISM: Artificial
<220> FEATURE:
<223> OTHER INFORMATION: Peptide linker

<400> SEQUENCE: 29

Ala Glu Ala Ala Ala Lys Ala
1               5

<210> SEQ ID NO 30
<211> LENGTH: 12
<212> TYPE: PRT
<213> ORGANISM: Artificial
<220> FEATURE:
<223> OTHER INFORMATION: Peptide linker

<400> SEQUENCE: 30

Ala Glu Ala Ala Ala Lys Glu Ala Ala Ala Lys Ala
1               5                   10

<210> SEQ ID NO 31
<211> LENGTH: 17
<212> TYPE: PRT
<213> ORGANISM: Artificial
<220> FEATURE:
<223> OTHER INFORMATION: Peptide linker

<400> SEQUENCE: 31

Ala Glu Ala Ala Ala Lys Glu Ala Ala Ala Lys Glu Ala Ala Ala Lys
1               5                   10                  15

Ala

<210> SEQ ID NO 32
<211> LENGTH: 22
<212> TYPE: PRT
<213> ORGANISM: Artificial
<220> FEATURE:
<223> OTHER INFORMATION: Peptide linker

<400> SEQUENCE: 32

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 33
<211> LENGTH: 27
```

```
<212> TYPE: PRT
<213> ORGANISM: Artificial
<220> FEATURE:
<223> OTHER INFORMATION: Peptide linker

<400> SEQUENCE: 33

Ala Glu Ala Ala Ala Lys Glu Ala Ala Ala Lys Glu Ala Ala Ala Lys
1               5                   10                  15
Glu Ala Ala Ala Lys Glu Ala Ala Ala Lys Ala
            20                  25

<210> SEQ ID NO 34
<211> LENGTH: 13
<212> TYPE: PRT
<213> ORGANISM: Artificial
<220> FEATURE:
<223> OTHER INFORMATION: Peptide linker

<400> SEQUENCE: 34

Ala Glu Ala Ala Ala Lys Glu Ala Ala Ala Lys Ala Gly
1               5                   10

<210> SEQ ID NO 35
<211> LENGTH: 14
<212> TYPE: PRT
<213> ORGANISM: Artificial
<220> FEATURE:
<223> OTHER INFORMATION: Peptide linker

<400> SEQUENCE: 35

Ala Glu Ala Ala Ala Lys Glu Ala Ala Ala Lys Ala Gly Ser
1               5                   10

<210> SEQ ID NO 36
<211> LENGTH: 5
<212> TYPE: PRT
<213> ORGANISM: Artificial
<220> FEATURE:
<223> OTHER INFORMATION: Peptide linker

<400> SEQUENCE: 36

Gly Gly Gly Gly Gly
1               5

<210> SEQ ID NO 37
<211> LENGTH: 5
<212> TYPE: PRT
<213> ORGANISM: Artificial
<220> FEATURE:
<223> OTHER INFORMATION: Peptide linker

<400> SEQUENCE: 37

Gly Gly Ala Gly Gly
1               5

<210> SEQ ID NO 38
<211> LENGTH: 8
<212> TYPE: PRT
<213> ORGANISM: Artificial
<220> FEATURE:
<223> OTHER INFORMATION: Peptide linker

<400> SEQUENCE: 38

Gly Gly Gly Gly Gly Gly Gly Gly
1               5
```

```
<210> SEQ ID NO 39
<211> LENGTH: 10
<212> TYPE: PRT
<213> ORGANISM: Artificial
<220> FEATURE:
<223> OTHER INFORMATION: Peptide linker

<400> SEQUENCE: 39

Gly Ala Gly Ala Gly Ala Gly Ala Gly Ala
1               5                   10

<210> SEQ ID NO 40
<211> LENGTH: 18
<212> TYPE: PRT
<213> ORGANISM: Artificial
<220> FEATURE:
<223> OTHER INFORMATION: Peptide linker

<400> SEQUENCE: 40

Arg Pro Leu Ser Tyr Arg Pro Pro Phe Pro Phe Gly Phe Pro Ser Val
1               5                   10                  15

Arg Pro

<210> SEQ ID NO 41
<211> LENGTH: 18
<212> TYPE: PRT
<213> ORGANISM: Artificial
<220> FEATURE:
<223> OTHER INFORMATION: Peptide linker

<400> SEQUENCE: 41

Tyr Pro Arg Ser Ile Tyr Ile Arg Arg Arg His Pro Ser Pro Ser Leu
1               5                   10                  15

Thr Thr

<210> SEQ ID NO 42
<211> LENGTH: 18
<212> TYPE: PRT
<213> ORGANISM: Artificial
<220> FEATURE:
<223> OTHER INFORMATION: Peptide linker

<400> SEQUENCE: 42

Thr Pro Ser His Leu Ser His Ile Leu Pro Ser Phe Gly Leu Pro Thr
1               5                   10                  15

Phe Asn

<210> SEQ ID NO 43
<211> LENGTH: 18
<212> TYPE: PRT
<213> ORGANISM: Artificial
<220> FEATURE:
<223> OTHER INFORMATION: Peptide linker

<400> SEQUENCE: 43

Arg Pro Val Ser Pro Phe Thr Phe Pro Arg Leu Ser Asn Ser Trp Leu
1               5                   10                  15

Pro Ala

<210> SEQ ID NO 44
<211> LENGTH: 18
<212> TYPE: PRT
<213> ORGANISM: Artificial
<220> FEATURE:
<223> OTHER INFORMATION: Peptide linker
```

<400> SEQUENCE: 44

Ser Pro Ala Ala His Phe Pro Arg Ser Ile Pro Arg Pro Gly Pro Ile
1               5                   10                  15

Arg Thr

<210> SEQ ID NO 45
<211> LENGTH: 18
<212> TYPE: PRT
<213> ORGANISM: Artificial
<220> FEATURE:
<223> OTHER INFORMATION: Peptide linker

<400> SEQUENCE: 45

Ala Pro Gly Pro Ser Ala Pro Ser His Arg Ser Leu Pro Ser Arg Ala
1               5                   10                  15

Phe Gly

<210> SEQ ID NO 46
<211> LENGTH: 18
<212> TYPE: PRT
<213> ORGANISM: Artificial
<220> FEATURE:
<223> OTHER INFORMATION: Peptide linker

<400> SEQUENCE: 46

Pro Arg Asn Ser Ile His Phe Leu His Pro Leu Leu Val Ala Pro Leu
1               5                   10                  15

Gly Ala

<210> SEQ ID NO 47
<211> LENGTH: 18
<212> TYPE: PRT
<213> ORGANISM: Artificial
<220> FEATURE:
<223> OTHER INFORMATION: Peptide linker

<400> SEQUENCE: 47

Met Pro Ser Leu Ser Gly Val Leu Gln Val Arg Tyr Leu Ser Pro Pro
1               5                   10                  15

Asp Leu

<210> SEQ ID NO 48
<211> LENGTH: 18
<212> TYPE: PRT
<213> ORGANISM: Artificial
<220> FEATURE:
<223> OTHER INFORMATION: Peptide linker

<400> SEQUENCE: 48

Ser Pro Gln Tyr Pro Ser Pro Leu Thr Leu Thr Leu Pro Pro His Pro
1               5                   10                  15

Ser Leu

<210> SEQ ID NO 49
<211> LENGTH: 18
<212> TYPE: PRT
<213> ORGANISM: Artificial
<220> FEATURE:
<223> OTHER INFORMATION: Peptide linker

<400> SEQUENCE: 49

Asn Pro Ser Leu Asn Pro Pro Ser Tyr Leu His Arg Ala Pro Ser Arg

```
                     1               5                  10                 15
Ile Ser

<210> SEQ ID NO 50
<211> LENGTH: 17
<212> TYPE: PRT
<213> ORGANISM: Artificial
<220> FEATURE:
<223> OTHER INFORMATION: Peptide linker

<400> SEQUENCE: 50

Leu Pro Trp Arg Thr Ser Leu Leu Pro Ser Leu Pro Leu Arg Arg
1               5                  10                 15

Pro

<210> SEQ ID NO 51
<211> LENGTH: 18
<212> TYPE: PRT
<213> ORGANISM: Artificial
<220> FEATURE:
<223> OTHER INFORMATION: Peptide linker

<400> SEQUENCE: 51

Pro Pro Leu Phe Ala Lys Gly Pro Val Gly Leu Leu Ser Arg Ser Phe
1               5                  10                 15

Pro Pro

<210> SEQ ID NO 52
<211> LENGTH: 18
<212> TYPE: PRT
<213> ORGANISM: Artificial
<220> FEATURE:
<223> OTHER INFORMATION: Peptide linker

<400> SEQUENCE: 52

Val Pro Pro Ala Pro Val Val Ser Leu Arg Ser Ala His Ala Arg Pro
1               5                  10                 15

Pro Tyr

<210> SEQ ID NO 53
<211> LENGTH: 17
<212> TYPE: PRT
<213> ORGANISM: Artificial
<220> FEATURE:
<223> OTHER INFORMATION: Peptide linker

<400> SEQUENCE: 53

Leu Arg Pro Thr Pro Pro Arg Val Arg Ser Tyr Thr Cys Cys Pro Thr
1               5                  10                 15

Pro

<210> SEQ ID NO 54
<211> LENGTH: 18
<212> TYPE: PRT
<213> ORGANISM: Artificial
<220> FEATURE:
<223> OTHER INFORMATION: Peptide linker

<400> SEQUENCE: 54

Pro Asn Val Ala His Val Leu Pro Leu Leu Thr Val Pro Trp Asp Asn
1               5                  10                 15

Leu Arg
```

<210> SEQ ID NO 55
<211> LENGTH: 18
<212> TYPE: PRT
<213> ORGANISM: Artificial
<220> FEATURE:
<223> OTHER INFORMATION: Peptide linker

<400> SEQUENCE: 55

Cys Asn Pro Leu Leu Pro Leu Cys Ala Arg Ser Pro Ala Val Arg Thr
1               5                   10                  15

Phe Pro

<210> SEQ ID NO 56
<211> LENGTH: 14
<212> TYPE: PRT
<213> ORGANISM: Artificial
<220> FEATURE:
<223> OTHER INFORMATION: Peptide linker

<400> SEQUENCE: 56

Leu Gly Thr Pro Thr Pro Thr Pro Thr Pro Thr Gly Glu Phe
1               5                   10

<210> SEQ ID NO 57
<211> LENGTH: 8
<212> TYPE: PRT
<213> ORGANISM: Artificial
<220> FEATURE:
<223> OTHER INFORMATION: Peptide linker

<400> SEQUENCE: 57

Glu Asp Phe Thr Arg Gly Lys Leu
1               5

<210> SEQ ID NO 58
<211> LENGTH: 21
<212> TYPE: PRT
<213> ORGANISM: Artificial
<220> FEATURE:
<223> OTHER INFORMATION: Peptide linker

<400> SEQUENCE: 58

Leu Glu Ala Ala Ala Arg Glu Ala Ala Ala Arg Glu Ala Ala Ala Arg
1               5                   10                  15

Glu Ala Ala Ala Arg
                20

<210> SEQ ID NO 59
<211> LENGTH: 16
<212> TYPE: PRT
<213> ORGANISM: Artificial
<220> FEATURE:
<223> OTHER INFORMATION: Peptide linker

<400> SEQUENCE: 59

Leu Glu Ala Ala Ala Arg Glu Ala Ala Ala Arg Glu Ala Ala Ala Arg
1               5                   10                  15

<210> SEQ ID NO 60
<211> LENGTH: 11
<212> TYPE: PRT
<213> ORGANISM: Artificial
<220> FEATURE:
<223> OTHER INFORMATION: Peptide linker

<400> SEQUENCE: 60

```
Leu Glu Ala Ala Ala Arg Glu Ala Ala Ala Arg
1               5                   10

<210> SEQ ID NO 61
<211> LENGTH: 6
<212> TYPE: PRT
<213> ORGANISM: Artificial
<220> FEATURE:
<223> OTHER INFORMATION: Peptide linker

<400> SEQUENCE: 61

Leu Glu Ala Ala Ala Arg
1               5

<210> SEQ ID NO 62
<211> LENGTH: 20
<212> TYPE: PRT
<213> ORGANISM: Artificial
<220> FEATURE:
<223> OTHER INFORMATION: Peptide linker

<400> SEQUENCE: 62

Glu Ala Ala Ala Arg Glu Ala Ala Ala Arg Glu Ala Ala Ala Arg Glu
1               5                   10                  15

Ala Ala Ala Arg
            20

<210> SEQ ID NO 63
<211> LENGTH: 15
<212> TYPE: PRT
<213> ORGANISM: Artificial
<220> FEATURE:
<223> OTHER INFORMATION: Peptide linker

<400> SEQUENCE: 63

Glu Ala Ala Ala Arg Glu Ala Ala Ala Arg Glu Ala Ala Ala Arg
1               5                   10                  15

<210> SEQ ID NO 64
<211> LENGTH: 10
<212> TYPE: PRT
<213> ORGANISM: Artificial
<220> FEATURE:
<223> OTHER INFORMATION: Peptide linker

<400> SEQUENCE: 64

Glu Ala Ala Ala Arg Glu Ala Ala Ala Arg
1               5                   10

<210> SEQ ID NO 65
<211> LENGTH: 5
<212> TYPE: PRT
<213> ORGANISM: Artificial
<220> FEATURE:
<223> OTHER INFORMATION: Peptide linker

<400> SEQUENCE: 65

Glu Ala Ala Ala Arg
1               5

<210> SEQ ID NO 66
<211> LENGTH: 10
<212> TYPE: PRT
<213> ORGANISM: Artificial
<220> FEATURE:
<223> OTHER INFORMATION: Peptide linker
```

```
<400> SEQUENCE: 66

Leu Thr Glu Glu Gln Gln Glu Gly Gly Gly
1               5                   10

<210> SEQ ID NO 67
<211> LENGTH: 9
<212> TYPE: PRT
<213> ORGANISM: Artificial
<220> FEATURE:
<223> OTHER INFORMATION: Peptide linker

<400> SEQUENCE: 67

Thr Glu Glu Gln Gln Glu Gly Gly Gly
1               5

<210> SEQ ID NO 68
<211> LENGTH: 19
<212> TYPE: PRT
<213> ORGANISM: Artificial
<220> FEATURE:
<223> OTHER INFORMATION: Peptide linker

<400> SEQUENCE: 68

Leu Ala Lys Leu Lys Gln Lys Thr Glu Gln Leu Gln Asp Arg Ile Ala
1               5                   10                  15

Gly Gly Gly

<210> SEQ ID NO 69
<211> LENGTH: 65
<212> TYPE: PRT
<213> ORGANISM: Artificial
<220> FEATURE:
<223> OTHER INFORMATION: Peptide linker

<400> SEQUENCE: 69

Leu Glu Leu Lys Thr Pro Leu Gly Asp Thr Thr His Thr Cys Pro Arg
1               5                   10                  15

Cys Pro Glu Pro Lys Ser Cys Asp Thr Pro Pro Pro Cys Pro Arg Cys
                20                  25                  30

Pro Glu Pro Lys Ser Cys Asp Thr Pro Pro Pro Cys Pro Arg Cys Pro
            35                  40                  45

Glu Pro Lys Ser Cys Asp Thr Pro Pro Cys Pro Arg Cys Pro Gly
        50                  55                  60

Gly
65

<210> SEQ ID NO 70
<211> LENGTH: 18
<212> TYPE: PRT
<213> ORGANISM: Artificial
<220> FEATURE:
<223> OTHER INFORMATION: Peptide linker

<400> SEQUENCE: 70

Leu Glu Pro Lys Ser Ser Asp Lys Thr His Thr Ser Pro Pro Ser Pro
1               5                   10                  15

Gly Gly

<210> SEQ ID NO 71
<211> LENGTH: 22
<212> TYPE: PRT
<213> ORGANISM: Homo sapiens
```

<400> SEQUENCE: 71

Ile Trp Ala Pro Leu Ala Gly Thr Cys Gly Val Leu Leu Ser Leu
1               5                   10                  15

Val Ile Thr Leu Tyr Cys
            20

<210> SEQ ID NO 72
<211> LENGTH: 72
<212> TYPE: DNA
<213> ORGANISM: Homo sapiens

<400> SEQUENCE: 72
atctacatct gggcgccctt ggccgggact tgtggggtcc ttctcctgtc actggttatc     60 acccttact gc                                                          72

<210> SEQ ID NO 73
<211> LENGTH: 135
<212> TYPE: DNA
<213> ORGANISM: Homo sapiens

<400> SEQUENCE: 73
accacgacgc cagcgccgcg accaccaaca ccggcgccca ccatcgcgtc gcagcccctg     60
tccctgcgcc agaggcgtg ccggccagcg gcggggggcg cagtgcacac gaggggggctg   120 gacttcgcct gtgat                                                    135

<210> SEQ ID NO 74
<211> LENGTH: 42
<212> TYPE: PRT
<213> ORGANISM: Homo sapiens

<400> SEQUENCE: 74

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 75
<211> LENGTH: 112
<212> TYPE: PRT
<213> ORGANISM: Homo sapiens

<400> SEQUENCE: 75

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg

```
<210> SEQ ID NO 76
<211> LENGTH: 126
<212> TYPE: DNA
<213> ORGANISM: Homo sapiens

<400> SEQUENCE: 76
aaacggggca gaaagaaact cctgtatata ttcaaacaac catttatgag accagtacaa      60
actactcaag aggaagatgg ctgtagctgc cgatttccag aagaagaaga aggaggatgt    120
gaactg                                                                126

<210> SEQ ID NO 77
<211> LENGTH: 240
<212> TYPE: DNA
<213> ORGANISM: Homo sapiens

<400> SEQUENCE: 77
agagtgaagt tcagcaggag cgcagacgcc cccgcgtaca agcagggcca gaaccagctc      60
tataacgagc tcaatctagg acgaagagag gagtacgatg ttttggacaa gagacgtggc    120
cgggaccctg agatgggggg aaagccgaga aggaagaacc ctcaggaagg cctgtacaat    180
gaactgcaga agataagat ggcggaggcc tacagtgaga ttgggatgaa aggcgagcgc     240

<210> SEQ ID NO 78
<211> LENGTH: 47
<212> TYPE: PRT
<213> ORGANISM: Homo sapiens

<400> SEQUENCE: 78

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45
```

What is claimed is:

1. A method of treating a cancer in a mammal, said method comprising:
first administering to said mammal a targeted interferon where said targeted interferon comprises an interferon attached to an antibody that binds to CD20 and
later administering to said mammal an adoptive T cell therapy targeted to said cancer, where said adoptive T cell therapy comprises administration of chimeric antigen receptor (CAR) T cells targeted to CD19;
wherein said targeted interferon improves recognition of tumor cells, and/or cytotoxicity, and/or activation and survival of said adoptive T cell therapy as compared to the use of said adoptive T cell therapy in the absence of said targeted interferon, wherein said cancer is selected from the group consisting of diffuse large B cell lymphoma (DLBCL), Burkitt lymphoma, primary mediastinal lymphoma, mantle cell lymphoma, small lymphocytic lymphoma, lymphoplasmacytoid lymphoma, marginal zone lymphoma, and primary CNS lymphoma.

2. The method of claim 1, wherein said targeted interferon increases cytokine production by effector T cells targeting said cancer compared to the use of said CAR T cells in the absence of said targeted interferon.

3. The method of claim 1, wherein said antibody is an antibody comprising said targeted interferon comprises an antibody selected from the group consisting of a single chain Fv (scFv), a FAB, a (Fab')$_2$, an (scFv)$_2$, and a full immunoglobulin.

4. The method of claim 1, wherein said interferon comprises an interferon selected from the group consisting of interferon alpha (IFNα), mutant interferon alpha, interferon beta (IFNβ), and interferon gamma (IFNγ).

5. The method of claim 4, wherein said interferon is an interferon alpha subtype selected from the group consisting of IFNα14, IFNα2, IFNα1, IFNα4, IFNα5, IFNα6, IFNα7, IFNα8, IFNα10, IFNα13, IFNα16, IFNα17, and IFNα21.

6. The method of claim 1, wherein said antibody is chemically coupled to said interferon, or said antibody is directly joined to said interferon.

7. The method of claim 1, wherein said antibody is joined to said interferon with a single amino acid or peptide linker.

8. The method of claim 7, wherein:
said peptide linker joins said interferon to the carboxyl terminus of the CH3 domain of said antibody; or
said peptide linker joins the amino terminus of said interferon to the carboxyl terminus of the CH3 domain of said antibody; or said peptide linker joins the carboxyl terminus of said interferon to the carboxyl terminus of the CH3 domain of said antibody.

9. The method of claim 7, wherein the amino acid sequence of said peptide linker is selected from the group consisting of

```
GGG, GGS, GGGGS,               (SEQ ID NO: 31)

SGGGGS,                         (SEQ ID NO: 32)

GGGGSGGGGS,                     (SEQ ID NO: 33)

A EAAAK A,                      (SEQ ID NO: 34)

A EAAAK EAAAK A,                (SEQ ID NO: 35)

A EAAAK EAAAK EAAAK A,          (SEQ ID NO: 36)

A EAAAK EAAAK EAAAK EAAAK A,    (SEQ ID NO: 37)

A EAAAK EAAAK EAAAK EAAAK EAAAK A,  (SEQ ID NO: 38)

AEAAAKEAAAKAG,                  (SEQ ID NO: 39)

AEAAAKEAAAKAGS,                 (SEQ ID NO: 40)

GGGGG,                          (SEQ ID NO: 41)

GGAGG,                          (SEQ ID NO: 42)

GGGGGGGG,                       (SEQ ID NO: 43)

GAGAGAGAGA,                     (SEQ ID NO: 44)

RPLSYRPPFPFGFPSVRP,             (SEQ ID NO: 45)

YPRSIYIRRRHPSPSLTT,             (SEQ ID NO: 46)

TPSHLSHILPSFGLPTFN,             (SEQ ID NO: 47)

RPVSPFTFPRLSNSWLPA,             (SEQ ID NO: 48)

SPAAHFPRSIPRPGPIRT,             (SEQ ID NO: 49)

APGPSAPSHRSLPSRAFG,             (SEQ ID NO: 50)

PRNSIHFLHPLLVAPLGA,             (SEQ ID NO: 51)

MPSLSGVLQVRYLSPPDL,             (SEQ ID NO: 52)

SPQYPSPLTLTLPPHPSL,             (SEQ ID NO: 53)

NPSLNPPSYLHRAPSRIS,             (SEQ ID NO: 54)

LPWRTSLLPSLPLRRRP,              (SEQ ID NO: 55)

PPLFAKGPVGLLSRSFPP,             (SEQ ID NO: 56)

VPPAPVVSLRSAHARPPY,             (SEQ ID NO: 57)

LRPTPPRVRSYTCCPTP,              (SEQ ID NO: 58)

PNVAHVLPLL TVPWDNLR,            (SEQ ID NO: 59)

CNPLLPLCARSPAVRTFP,             (SEQ ID NO: 60)

LGTPTPTPTPTGEF,                 (SEQ ID NO: 61)

EDFTRGKL,                       (SEQ ID NO: 62)

L EAAAR EAAAR EAAAR EAAAR,      (SEQ ID NO: 63)

L EAAAR EAAAR EAAAR,            (SEQ ID NO: 64)

L EAAAR EAAAR,                  (SEQ ID NO: 65)

L EAAAR,                        (SEQ ID NO: 66)

EAAAR EAAAR EAAAR EAAAR,        (SEQ ID NO: 67)

EAAAR EAAAR EAAAR,              (SEQ ID NO: 68)

EAAAR EAAAR,                    (SEQ ID NO: 69)

EAAAR,                          (SEQ ID NO: 70)

LTEEQQEGGG,                     (SEQ ID NO: 71)

TEEQQEGGG,                      (SEQ ID NO: 72)

LAKLKQKTEQLQDRIAGGG,            (SEQ ID NO: 73)

LELKTPLGDT THTCPRCPEP KSCDTPPPCP RCPEPKSCDT
PPPCPRCPEP KSCDTPPPCP RCPGG, and  (SEQ ID NO: 74)

LEPKSSDKTHTSPPSPGG.             (SEQ ID NO: 75)
```

10. The method of claim 1, wherein said targeted interferon comprises an interferon alpha 14 attached to an antibody comprising the variable region of rituximab.

11. The method of claim 10, wherein said antibody is an IgG.

12. The method of claim 10, wherein said antibody is attached to said interferon by an SGGGGS (SEQ ID NO:27) linker.

13. The method of claim 1, wherein said adoptive T cell therapy is administered 30 days or less after administration of said targeted interferon.

* * * * *